United States Patent
Kato et al.

(10) Patent No.: US 6,613,805 B2
(45) Date of Patent: *Sep. 2, 2003

(54) AMINE COMPOUNDS, THEIR PRODUCTION AND USE

(75) Inventors: Kaneyoshi Kato, Kawanishi (JP); Jun Terauchi, Ikeda (JP); Hiroaki Fukumoto, Suita (JP); Mitsuru Kakihana, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/931,140

(22) Filed: Aug. 16, 2001

(65) Prior Publication Data

US 2002/0032189 A1 Mar. 14, 2002

Related U.S. Application Data

(62) Division of application No. 09/331,460, filed as application No. PCT/JP98/00780 on Feb. 26, 1998, now Pat. No. 6,310,107.

(30) Foreign Application Priority Data

Feb. 27, 1997 (JP) .............................. 9-043940
Jul. 18, 1997 (JP) .............................. 9-193497

(51) Int. Cl.[7] ...................... A61K 31/137; C07C 217/60
(52) U.S. Cl. ...................... 514/654; 514/319; 546/206; 564/378
(58) Field of Search ................. 564/378; 514/654, 514/319; 546/206

(56) References Cited

U.S. PATENT DOCUMENTS

| 5,137,901 | A |   | 8/1992  | Junge et al. ............. 514/373 |
| 6,048,877 | A | * | 4/2000  | Ahmad et al. ............ 514/319 |
| 6,310,107 | B1 | * | 10/2001 | Kato et al. ............... 514/654 |

FOREIGN PATENT DOCUMENTS

| AU | A-31189/89    | 9/1989  |
| EP | A 332064      | 9/1989  |
| EP | A 754455      | 1/1997  |
| JP | A 63-77842    | 4/1988  |
| WO | WO-A 92/15558 | 9/1992  |
| WO | WO-A 95/32967 | 12/1995 |
| WO | WO 98/06691   | 2/1998  |

* cited by examiner

Primary Examiner—Richard L. Raymond
(74) Attorney, Agent, or Firm—Mark Chao; Elaine M. Ramesh

(57) ABSTRACT

A compound of the formula:

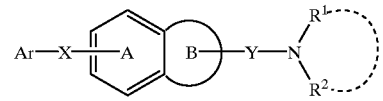

wherein Ar is an aromatic ring assembly group which may be substituted or a fused aromatic group which may be substituted; X is (i) a bond, (ii) —S—, —SO— or —$SO_2$—, (iii) $C_{1-6}$ alkylene, $C_{2-6}$ alkenylene or $C_{2-6}$ alkynylene, etc., (iv) —CO—O— or (v) —$(CH_2)$p-$X^1$—, —$(CH_2)$p-$X^1$-$(CH_2)$q-, —$(CH_2)$r-CO-$X^1$-, —$SO_2$—$NR^8$— or —$(CH_2)$r-$SO_2$—$NR^8$— wherein $X^1$ is O or $NR^8$, $R^8$ is H, a hydrocarbon group which may be substituted or an acyl, p is 0 to 5, q is 1 to 5, p+q is 1 to 5, and r is 1 to 4; Y is a divalent $C_{1-6}$ aliphatic hydrocarbon group optionally containing O or S, which may be substituted; $R^1$ and $R^2$ each is H or a lower alkyl which may be substituted, or $R^1$ and $R^2$ form a N-containing heterocyclic ring which may be substituted; Ring A is a benzene ring which may be further substituted; and Ring B is a 4- to 8-membered ring which may be further substituted, or a salt thereof has the effect of inhibiting amyloid-β protein production and/or secretion and is useful as a pharmaceutical composition for preventing and/or treating the neurodegenerative disease, etc.

33 Claims, No Drawings

AMINE COMPOUNDS, THEIR PRODUCTION AND USE

This application is a divisional of U.S. patent application Ser. No. 09/331,460, filed on Jun. 21, 1999, now U.S. Pat. No. 6,310,107, issued Oct. 30, 2001, which was the National Phase filing of International Patent Application No. PCT/JP98/00780, filed Feb. 26, 1998.

TECHNICAL FIELD

The present invention relates to an amine compound having an excellent effect of inhibiting production and/or secretion of amyloid-β protein, a production and use thereof. Especially, it is effective for preventing and/or treating, for example, neurodegenerative diseases, amyloid angiopathy, neurological disorders caused by cerebrovascular disorders, and so forth.

BACKGROUND ART

Alzheimer's disease is a neurodegenerative disease, which is characterized by the degeneration and loss of neuronal cells accompanied by the formation of senile plaques and neurofibrillary tangles. Senile plaque that is the most characteristic in Alzheimer's disease consist of essentially amyloid-β protein (hereinafter referred to as Aβ) [see Biochem. Biophys. Res. Commun., 122, 1311 (1984)] and other intracerebral components. It is known that Aβ comprised of 40 or 42 amino acids (hereinafter referred to as $Aβ_{1-40}$ and $Aβ_{1-42}$, respectively) is toxic to neurons and induces neurofibrillary changes.

Some patients with familial Alzheimer's disease are known to have APP (amyloid precursor protein) gene mutation, and it is well known that the cells transfected with such mutated gene produce and secrete an increased amount of Aβ [for example, see Nature, 360, 672 (1992); Science, 259, 514 (1993); Science, 264, 1336 (1994), etc.].

Based on the information, medicines which inhibit production and/or secretion are useful for preventing and/or treating diseases caused by Aβ (e.g., Alzheimer's disease, Down's syndrome, etc).

Alternatively, secreted form of amyloid precursor protein (sAPP) is reported to have neurotrophic factor like property (Neuron, 10, 243–254,1993). As neurotrophic factor like property, 1) survival and preserving effect to the neuronal cell; 2) stimulating the synapse formation; 3) protection of neuronal cell death; and 4) long term potentiation in hippocampus are given as examples. By the above-mentioned property, drugs which stimulate the sAPP secretion are also useful in preventing and treating 1) neurodegenerative diseases such as dementia (e.g., senile dementia, amnesia, etc.), Alzheimer's disease, Down's syndrome, Parkinson's disease, Creutzfeldt-Jacob disease, amyotrophic sclerosis on lateral fasciculus, Huntington's disease, multiple sclerosis, etc., 2) neurological disorders involved in cerebrovascular disorders (e.g., cerebral infarction, encephalorrhagia, etc.), a head injury or an injury of spinal cord, and so forth.

EP-A-652009 discloses peptide derivatives which is a protease inhibitor exhibiting an Aβ production inhibiting effect in in vitro experiments using cell lines.

On the other hand, the following bicyclic amine compounds are known.

1) JP-A-2-96552 (U.S. Pat. No. 5,137,901) discloses a compound of the formula:

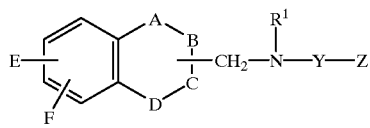

wherein Y represents a straight-chain or branched, substituted or unsubstituted alkylene chain having up to 6 carbon atoms; Z represents a group of the formula: $—NR^2R^3$, $—OR^4$, or the like; $R^2$ and $R^3$ are identical or different and represent hydrogen, alkyl, alkenyl or cycloalkyl, or represent aryl which may be substituted by halogen, etc.; $R^4$ represents hydrogen, alkyl, alkenyl, or the like; $R^1$ represents hydrogen, alkyl, aralkyl, heteroarylalkyl or a group of the formula: $—(Y^1—Z^1)$ in which $Y^1$ and $Z^1$ are identical or different and have the same meanings as Y and Z; A and D each represents a group of the formula:

$—CH_2$, O, S or $NR^{13}$, or the moiety of —CH or N of a double bond C═C or C═NH, with the proviso that either only A or only D represents oxygen, sulfur or $N—R^{13}$; $R^{13}$ represents hydrogen, alkyl, alkoxy, acyl, alkoxycarbonyl or alkylsulfonyl; B represents a group of the formula:

$—CH_2$ or

or the moiety of —CH or N of a double bond C═C or C═N; C represents a group of the formula:

or the moiety of C of a double bond C═C or C═N; E and F are identical or different and each represents hydrogen, alkyl, alkoxy, halogen, nitro, cyano, trifluoromethyl, trifluoromethoxy or a group of the formula:

$—CONR^2R^3$ in which $R^2$ and $R^3$ have the same meanings as above, or E and F together form a substituted or unsubstituted carbocycle having 6 carbon atoms, which is agonist, partial agonist and antagonist on the serotonin receptors and is suitable for the treatment of central nervous system disorders, etc.

2) JP-A-63-77842 discloses a compound of the formula:

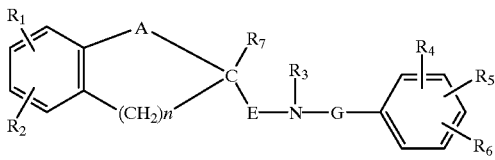

wherein n represents 1 or 2; A represents a carbonyl while $R_7$ is hydrogen, or A represents a group of the formula:

$—CHR_8—$ wherein $R_8$ represents hydrogen, alkanoyloxy or alkoxycarbonyl, while $R_7$ is hydrogen or $R_7$ and $R_8$ together form another bond; E represents a straight-chain alkylene which has 3 or 4 carbon atoms and may be substituted by an alkyl; G represents a straight-chain alkylene which has 2 to 5 carbon atoms and may be substituted by an alkyl; $R_1$ represents hydrogen, trifluoromethyl, nitro, amino, alkylamino, dialkylamino, alkyl, hydroxy, alkoxy or phenylalkoxy; $R_2$ represents hydrogen, halogen atoms, hydroxy, alkoxy, phenylalkoxy or alkyl; or $R_1$ and $R_2$ together form an alkylenedioxy having 1 or 2 carbon atoms; $R_3$ represents hydrogen, alkenyl or alkyl having 3 to 5 carbon atoms; $R_4$ represents hydrogen, halogen atoms, alkyl, or the like; $R_5$ represents hydrogen, halogen atoms, alkyl, or the like; and $R_6$ represents hydrogen, halogen atoms, alkyl, or the like, which is suitable for the treatment of sinus tachycardia and also for the prevention and treatment of ischemic heart disease because of its pharmacological action, decrease in the heart rate and oxygen demand of the heart.

3) WO 92/15558 discloses a compound of the formula:

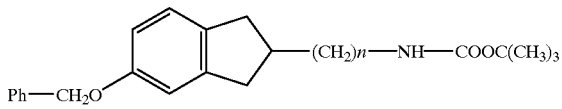

wherein n represents an integer of 1 to 4, which is an intermediate of a compound having a thromboxane $A_2$ antagonistic effect.

4) WO 95/32967 discloses amide derivatives of the formula:

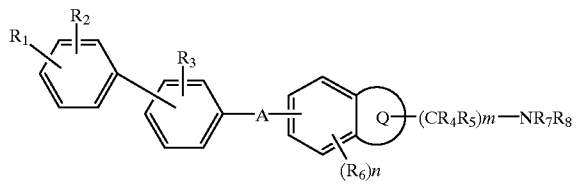

wherein A is CONR where R is hydrogen or $C_{1-6}$ alkyl; Q is an optionally substituted 5 to 7-membered heterocyclic ring containing 1 to 3 heteroatoms selected from oxygen, nitrogen or sulphur; $R_1$ is hydrogen, halogen, etc.; $R_2$ and $R_3$ are independently hydrogen, halogen, etc.; $R_4$ and $R_5$ are independently hydrogen or $C_{1-6}$ alkyl; $R_6$ is halogen, hydroxy, etc.; $R_7$ and $R_8$ are independently hydrogen, $C_{1-6}$ alkyl, aralkyl, or together with the nitrogen atom to which they are attached from an optionally substituted 5 to 7-membered heterocyclic ring containing one or two heteroatoms selected from oxygen, nitrogen or sulphur; m is 0 to 4; and n is 0, 1 or 2, which has $5HT_{1D}$ receptor antagonist activity and is useful for the treatment of various CNS disorders.

5) EP-A-754455 discloses a pharmaceutical compositions for the therapeutic application as neuroprotectors in Parkinson's and Alzheimer's diseases containing a compound of the formula:

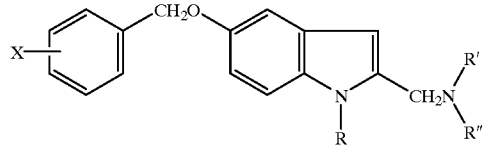

wherein X is H, halogen, alkoxy, alkyl, alkylthio, aryl, aryloxy; R is H, $CH_3$ or other aliphatic, alicyclic or aryl radicals; R' is H, $CH_3$ or other aliphatic or alicyclic $C_1$–$C_3$ radicals, or an aryl or arylalkyl, or a radical the same as those indicated for R"; and R" is H, $CH_3$ or other aliphatic or alicyclic $C_1$–$C_3$ radicals, or an aryl or arylalkyl, or an acetylene or allene group, being potent selective monoamine oxydase B inhibitors.

The conventional Aβ production inhibitors for the treatment of Alzheimer's disease are problematic in their oral absorbability, stability, etc. and are therefore unsatisfactory as medicines. It is desired to develop a compound which is different from the known compounds mentioned above in its chemical structure and which have an excellent inhibitory effect on Aβ production and/or secretion and is therefore satisfactorily used in medicines.

DISCLOSURE OF INVENTION

We, the present inventors have studied various compounds having an inhibitory effect on Aβ production and/or secretion and, as a result, have succeeded in, for the first time, the production of novel a compound of the formula:

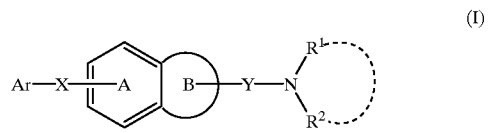

(I)

wherein Ar represents an aromatic ring assembly group which may be substituted or a fused aromatic group which may be substituted;

X represents (i) a bond, (ii) —S—, —SO— or —SO$_2$—, (iii) a $C_{1-6}$ alkylene, $C_{2-6}$ alkenylene or $C_{2-6}$ alkynylene group, each of which may be substituted by 1 to 3 substituents selected from the group consisting of oxo and $C_{1-6}$ alkyl, (iv) —CO—O— or (v) a group of the formula:

—(CH$_2$)p—X$^1$—, —(CH$_2$)p-X$^1$—(CH$_2$)q-, —(CH$_2$)r-CO—X$^1$—, —SO$_2$—NR$^8$— or

—(CH$_2$)r-SO$_2$—NR$^8$— wherein $X^1$ represents O (oxygen atom) or NR$^8$, R$^8$ represents a hydrogen atom, a hydrocarbon group which may be substituted or an acyl, p represents an integer of 0 to 5, q represents an integer of 1 to 5, p+q is an integer of 1 to 5, and r represents an integer of 1 to 4;

Y represents a divalent $C_{1-6}$ aliphatic hydrocarbon group which may contain an oxygen atom or a sulfur atom and may be substituted;

$R^1$ and $R^2$ each represents a hydrogen atom or a lower alkyl which may be substituted, or $R^1$ and $R^2$ form, taken together with the adjacent nitrogen atom, a nitrogen-containing heterocyclic ring which may be substituted;

Ring A represents a benzene ring which may be further substituted apart from the group of the formula:

wherein each symbol is as defined above; and

Ring B represents a 4- to 8-membered ring which may be further substituted apart from the group of the formula:

wherein each symbol is as defined above;

provided that, when the fused ring to be formed by Ring A and Ring B is an indole ring, the group of the formula:

wherein each symbol is as defined above is substituted on 4-, 6- or 7-position of the indole ring, or a salt thereof [hereinafter sometimes referred to as compound (I)], which is characterized by the chemical structure in that the benzene ring A of the skeleton of the formula:

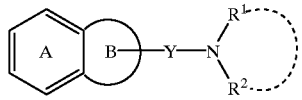

wherein the symbols have the same meanings as above, is substituted by the group of the formula:

wherein the symbols have the same meanings as above. We have found for the first time that compound (I), being based on its specific chemical structure, has an unexpected, excellent inhibitory effect on Aβ production and/or secretion, that a compound of the formula:

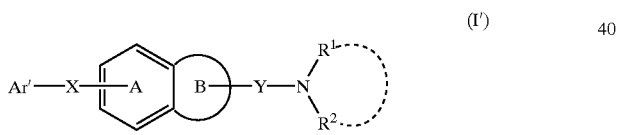

wherein Ar' represents an aromatic group which may be substituted, and the other symbols have the same meanings as above, or salt thereof [hereinafter sometimes referred to as compound (I')] also has an unexpected, excellent inhibitory effect on Aβ production and/or secretion, and that those compounds have low toxicity and are therefore satisfactory as medicines. Compound (I) is within the scope of compound (I'). On the basis of these findings, the inventors have completed the present invention.

Specifically, the present invention relates to:

(1) a compound of the formula:

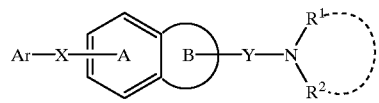

wherein Ar represents an aromatic ring assembly group which may be substituted or a fused aromatic group which may be substituted;

X represents a chemical bond or a spacer of which the number of atoms constituting the principal chain is 1 to 6;

Y represents a divalent $C_{1-6}$ aliphatic hydrocarbon group which may contain an oxygen atom or a sulfur atom and may be substituted;

$R^1$ and $R^2$ each represents a hydrogen atom or a lower alkyl which may be substituted, or $R^1$ and $R^2$ form, taken together with the adjacent nitrogen atom, a nitrogen-containing heterocyclic ring which may be substituted;

Ring A represents a benzene ring which may be further substituted apart from the group of the formula:

wherein each symbol is as defined above; and

Ring B represents a 4- to 8-membered ring which may be further substituted apart from the group of the formula:

wherein each symbol is as defined above;

provided that, when the fused ring to be formed by Ring A and Ring B is an indole ring, the group of the formula:

wherein each symbol is as defined above is substituted on 4-, 6- or 7-position of the indole ring, or a salt thereof;

(2) compound (I), wherein

Ar is (i) an aromatic ring assembly group which is composed of two or three rings selected from the class consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, which rings are directly bonded to each other via a single bond, and which assembly group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or (ii) a fused bi- or tri-cyclic $C_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy;

$R^8$ is (a) a hydrogen atom, (b) a $C_{1-6}$ alkyl, $C_{2-6}$ alkenyl, $C_{2-6}$ alkynyl, $C_{3-6}$ cycloalkyl being optionally condensed with one benzene ring, $C_{6-14}$ aryl or $C_{7-19}$ aralkyl group which may be substituted by 1 to 5 substituents selected form the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{3-6}$ cycloalkyl, (7) optionally halogenated $C_{1-6}$ alkoxy, (8) optionally halogenated $C_{1-6}$ alkylthio, (9) hydroxy, (10) amino, (11) mono-$C_{1-6}$ alkylamino, (12) di-$C_{1-6}$ alkylamino, (13) formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl, (14) formylamino, $C_{1-6}$ alkyl-carboxamido, $C_{6-10}$ aryl-carboxamido, $C_{1-6}$ alkoxy-carboxamido or $C_{1-6}$ alkylsulfonylamino, (15) $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy or nicotinoyloxy, (16) 5- to 7-membered saturated cyclic amino, (17) sulfo, (18) a phenyl or 5- or 6-membered aromatic heterocyclic group containing 1 to 4 hetero atoms selected from the group consisting of nitrogen, oxygen and sulfur atoms in addition to carbon atoms, each of which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (19) an aromatic ring assembly group which is composed of two or three rings selected from the class consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, are directly bonded to each other via a single bond, and which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-11}$ aryloxy-carbonyl, $C_{7-16}$ aralkyloxy-carbonyl, 5- or 6-membered heterocycle carbonyl, mono-$C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, and (20) a fused bi- or tri-cyclic $C_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or (c) formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl;

Y is a $C_{1-6}$ alkylene, a $C_{2-6}$ alkenylene, a $C_{2-6}$ alkynylene or a group of the formula:

$$-(CH_2)m-Y^1-(CH_2)n-$$

wherein $-Y^1-$ is $-O-$, $-S-$, $-SO-$ or $-SO_2-$, m is an integer of 0 to 4, n is an integer of 1 to 5, and m+n is an integer of 1 to 5;

$R^1$ and $R^2$ each is a hydrogen atom or a $C_{1-6}$ alkyl which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy, $C_{6-10}$ aryloxy and $C_{6-10}$ aryl or $R^1$ and $R^2$ form, taken together with the adjacent nitrogen atom, a 3- to 8-membered nitrogen-containing heterocyclic ring having one nitrogen atom and optionally having 1 to 3 hetero atoms selected from the group consisting of nitrogen, oxygen and sulfur atoms in addition to carbon atoms, which ring may be substituted by 1 to 5 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{3-6}$ cycloalkyl, (7) optionally halogenated $C_{1-6}$ alkoxy, (8) optionally halogenated $C_{1-6}$ alkylthio, (9) hydroxy, (10) amino, (11) mono-$C_{1-6}$ alkylamino, (12) di-$C_{1-6}$ alkylamino, (13) formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl, (14) formylamino, $C_{1-6}$ alkyl-carboxamido, $C_{6-10}$ aryl-carboxamido, $C_{1-6}$ alkoxy-carboxamido or $C_{1-6}$ alkylsulfonylamino, (15) $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy or nicotinoyloxy, (16) 5- to 7-membered saturated cyclic amino, (17) sulfo, (18) a phenyl or 5- or 6-membered aromatic heterocyclic group containing 1 to 4 hetero atoms selected from the group consisting of nitrogen, oxygen and sulfur atoms in addition to carbon atoms, each of which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (19) an aromatic ring assembly group which is composed of two or three rings selected from the class consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, are directly bonded to each other via a single bond, and which group may be substituted by 1 to 5 substituents selected from the group consisting of halogen atoms, $C_{1-3}$ alkylenedioxy, nitro, cyano, optionally halogenated $C_{1-6}$ alkyl, option-ally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (20) a fused bi- or tri-cyclic $C_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (21) an oxo and (22) $C_{7-19}$ aralkyl;

Ring A is a benzene ring which may be further substituted by 1 to 3 substituents selected from the group consisting of halogen atoms, optionally halogenated $C_{1-6}$ alkyl, optionally halogenated $C_{1-6}$ alkoxy, hydroxy and amino, apart from the group of the formula:

—X—Ar wherein each symbol is as defined above; and

Ring B is a 4- to 8-membered ring of the formula:

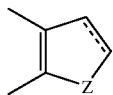

wherein - - - is a single bond or a double bond, and Z is (i) a bond, (ii) a $C_{1-4}$ alkylene, (iii) a $C_{2-4}$ alkenylene, (iv) —O—$CH_2$—, (v) —O—$CH_2$—$CH_2$— or (vi) a group of the formula:

—$NR^{8a}$—$CH_2$— or

—$NR^{8a}$—$CH_2$—$CH_2$— wherein $R^{8a}$ is (a) a hydrogen atom, (b) a $C_{1-6}$ alkyl, $C_{2-6}$ alkenyl, $C_{2-6}$ alkynyl, $C_{3-6}$ cycloalkyl being optionally condensed with one benzene ring, $C_{6-14}$ aryl or $C_{7-9}$ aralkyl group which may be substituted by 1 to 5 substituents selected form the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{3-6}$ cycloalkyl, (7) optionally halogenated $C_{1-6}$ alkoxy, (8) optionally halogenated $C_{1-6}$ alkylthio, (9) hydroxy, (10) amino, (11) mono-$C_{1-6}$ alkylamino, (12) di-$C_{1-6}$ alkylamino, (13) formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl, (14) formylamino, $C_{1-6}$ alkyl-carboxamido, $C_{6-10}$ aryl-carboxamido, $C_{1-6}$ alkoxy-carboxamido or $C_{1-6}$ alkylsulfonylamino, (15) $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy or nicotinoyloxy, (16) 5- to 7-membered saturated cyclic amino, (17) sulfo, (18) a phenyl or 5- or 6-membered aromatic heterocyclic group containing 1 to 4 hetero atoms selected from the group consisting of nitrogen, oxygen and sulfur atoms in addition to carbon atoms, each of which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (19) an aromatic ring assembly group which is composed of two or three rings selected from the class consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, are directly bonded to each other via a single bond, and which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, and (20) a fused bi- or tri-cyclic $C_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or (c) formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl, which ring may be further substituted by 1 to 3 substituents selected from the group consisting of oxo, $C_{1-6}$ alkyl and hydroxy, apart from the group of the formula:

—Y—$NR^1R^2$ wherein each symbol is as defined above;

(3) compound (I), wherein Ar is an aromatic ring assembly group which may be substituted;

(4) a compound of the above (3), wherein the aromatic rings of the aromatic ring assembly group are two or three aromatic rings selected from the group consisting of benzene, thiophene, pyridine, pyrimidine, 1,2,4-oxadiazole, 1,3,4-oxadiazole, naphthalene, and benzofuran;

(5) a compound of the above (3), wherein the aromatic ring assembly group is 2-, 3- or 4-biphenylyl;

(6) compound (I), wherein Ar is a 4-biphenylyl which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy;

(7) compound (I), wherein X is a divalent $C_{1-6}$ aliphatic hydrocarbon group which may contain an oxygen atom;

(8) compound (I), wherein X is a $C_{1-6}$ alkylene;

(9) compound (I), wherein X is a group of the formula:

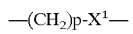
—(CH$_2$)p-X$^1$— wherein each symbol is as defined above;

(10) a compound of the above (9), wherein p is 1;

(11) a compound of the above (10), wherein $X^1$ is O;

(12) a compound of the above (10), wherein $X^1$ is $NR^{8b}$ wherein $R^{8b}$ is hydrogen or $C_{1-6}$ alkyl-carbonyl;

(13) compound (I), wherein $X^1$ is a group of the formula:

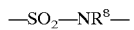
—SO$_2$—NR$^8$— wherein each symbol is as defined above;

(14) a compound of the above (13), wherein $R^8$ is hydrogen;

(15) compound (I), wherein Y is a divalent $C_{1-6}$ aliphatic hydrocarbon group;

(16) compound (I), wherein Y is $C_{1-6}$ alkylene;

(17) compound (I), wherein $R^1$ and $R^2$ each is $C_{1-6}$ alkyl;

(18) compound (I), wherein Ring A is a benzene ring substituted by the group of the formula:

—X—Ar wherein each symbol is as defined above;

(19) compound (I), wherein Ring B is a 4- to 8-membered ring of the formula:

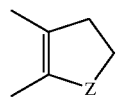

wherein Z is (i) a bond, (ii) a $C_{1-4}$ alkylene, (iii) a $C_{2-4}$ alkenylene, (iv) —O—CH$_2$—, (v) —O—CH$_2$—CH$_2$— or (vi) a group of the formula:

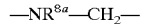
—NR$^{8a}$—CH$_2$— or

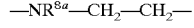
—NR$^{8a}$—CH$_2$—CH$_2$— wherein $R^{8a}$ is (a) a hydrogen atom, (b) a $C_{1-6}$ alkyl, $C_{2-6}$ alkenyl, $C_{2-6}$ alkynyl, $C_{3-6}$ cycloalkyl being optionally condensed with one benzene ring, $C_{6-14}$ aryl or $C_{7-19}$ aralkyl group which may be substituted by 1 to 5 substituents selected form the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{3-6}$ cycloalkyl, (7) optionally halogenated $C_{1-6}$ alkoxy, (8) optionally halogenated $C_{1-6}$ alkylthio, (9) hydroxy, (10) amino, (11) mono-$C_{1-6}$ alkylamino, (12) di-$C_{1-6}$ alkylamino, (13) formyl, carboxy, carbamoyl, $C_{3-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{3-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl, (14) formylamino, $C_{1-6}$ alkyl-carboxamido, $C_{6-10}$ aryl-carboxamido, $C_{1-6}$ alkoxy-carboxamido or $C_{1-6}$ alkylsulfonylamino, (15) $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy or nicotinoyloxy, (16) 5- to 7-membered saturated cyclic amino, (17) sulfo, (18) a phenyl or 5- or 6-membered aromatic heterocyclic group containing 1 to 4 hetero atoms selected from the group consisting of nitrogen, oxygen and sulfur atoms in addition to carbon atoms, each of which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (19) an aromatic ring assembly group which is composed of two or three rings selected from the class consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, are directly bonded to each other via a single bond, and which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, and (20) a fused bi- or tri-cyclic $C_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or (c) formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl, which ring may be further substituted by 1 to 3 substituents selected from the group consisting of oxo, $C_{1-6}$ alkyl and hydroxy, apart from the group of the formula:

wherein each symbol is as defined above;

(20) a compound of the above (19), wherein $R^{8a}$ is hydrogen, optionally halogenated $C_{1-6}$ alkyl, $C_{1-6}$ alkyl-carbonyl, $C_{1-6}$ alkoxy-carbonyl, $C_{6-10}$ ( aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl;

(21) compound (I), wherein Ring B is a 6-membered carbocyclic or heterocyclic ring substituted by a group of the formula:

wherein each symbol is as defined above;

(22) compound (I), wherein Ring B is a ring of the formula:

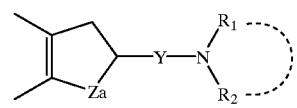

wherein Za is $C_{1-3}$ alkylene or a group of the formula:

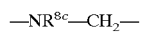

wherein $R^{8c}$ is hydrogen, optionally halogenated $C_{1-6}$ alkyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl;

(23) a compound of the above (22), wherein Za is ethylene;

(24) compound (I), wherein the fused ring to be formed by Ring A and Ring B is a ring of the formula:

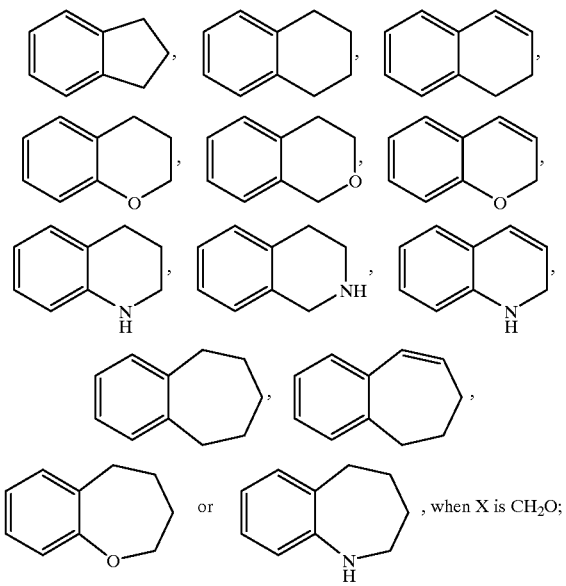

(25) compound (I), wherein Ar is 2-, 3- or 4-biphenylyl which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl and $C_{1-6}$ alkyl-carboxamido;

X is $C_{1-3}$ alkylene which may contain an oxygen atom;

Y is $C_{1-6}$ alkylene;

$R^1$ and $R^2$ each is $C_{1-6}$ alkyl;

Ring A is a benzene ring substituted by the group of the formula:

wherein each symbol is as defined above; and

Ring B is a 6-membered carbocyclic or heterocyclic ring substituted by the group of the formula:

wherein each symbol is as defined above;

(26) compound (I), which is a compound of the formula:

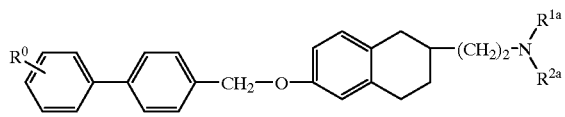

wherein $R^0$ is 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl and $C_{1-6}$ alkyl-carboxamido; and $R^{1a}$ and $R^{2a}$ each is $C_{1-6}$ alkyl, or a salt thereof;

(27) compound (I), which is a compound of the formula:

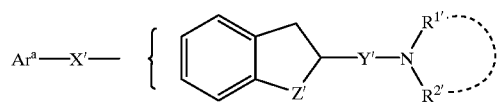

wherein $Ar^a$ is (i) 2, 3- or 4-biphenylyl which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, amino, formyl and $C_{1-6}$ alkyl-carboxamido, (ii) 4-(2-thienyl) phenyl or 4-(3-thienyl) phenyl, (iii) 4-(3-pyridyl)phenyl, (iv) 6-phenyl-3-pyridyl which may be substituted by a $C_{1-6}$ alkoxy, (v) 5-phenyl-1,3,4-oxadiazol-2-yl, (vi) 4-(2-naphthyl) phenyl, (vii) 4-(2-benzofuranyl)phenyl, (viii) 1- or 2-naphthyl, (ix) 2-quinolyl, (x) 2-benzothiazolyl or (xi) 2-benzofuranyl;

X' is —CH$_2$—O—, —SO$_2$—NH— or a group of the formula: —CH$_2$—NR$^{8'}$— wherein R$^{8'}$ is hydrogen or $C_{1-3}$ alkyl-carbonyl;

Y' is $C_{1-6}$ alkylene;

Z' is —CH$_2$—CH$_2$— or a group of the formula: —NR$^{8''}$—CH$_2$— wherein R$^{8''}$ is hydrogen, $C_{1-3}$ alkyl, $C_{1-3}$ alkyl-carbonyl or $C_{1-3}$ alkylsulfonyl; and R$^{1'}$ and R$^{2'}$ each is $C_{1-6}$ alkyl which may be substituted by 1 to 5 substituents selected from the group consisting of di-$C_{1-3}$ alkylamino, $C_{1-3}$ alkoxy-carbonyl and phenyl, or R$^{1'}$ and R$^{2'}$ form, taken together with the adjacent nitrogen atom, a pyrrolidin-1-yl, piperidino or piperazin-1-yl which may be substituted by 1 to 3 substituents selected from the group consisting of hydroxy, $C_{1-3}$ alkoxy-carbonyl, piperidino, phenyl and benzyl, or a salt thereof;

(28) compound (I) which is
6-(4-biphenylyl)methoxy-2-[2-(N,N-dimethylamino) ethyl] tetralin, 6-(4-biphenylyl)methoxy-2-(N,N-dimethylamino) methyltetralin, 2-(N,N-dimethylamino)methyl-6-(4'-methoxybiphenyl-4-yl) methoxytetralin, (+)-6-(4-biphenylyl)methoxy-2-[2-(N,N-dimethylamino) ethyl]tetralin, (+)-6-(4-biphenylyl)methoxy-2-[2-(N,N-diethylamino) ethyl]tetralin, (+)-2-[2-(N,N-dimethylamino)ethyl]-6-(4'-methylbiphenyl-4-yl) methoxytetralin, (+)-2-[2-(N,N-dimethylamino)ethyl]-6-(4'-methoxybiphenyl-4-yl) methoxytetralin, (+)-6-(2',4'-dimethoxybiphenyl-4-yl)methoxy-2-[2-(N,N-dimethylamino) ethyl]tetralin, (+)-6-[4-(1,3-benzodioxol-5-yl)phenyl]methoxy-2-[2-(N,N-dimethylamino) ethyl]tetralin, or (+)-6-(3',4'-dimethoxybiphenyl-4-yl)methoxy-2-[2-(N,N-dimethylamino) ethyl]tetralin, or a salt thereof;

(29) a process for producing of compound (I), which comprises;

i) subjecting a compound of the formula:

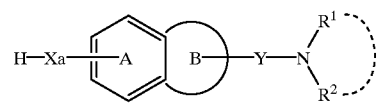

wherein Xa represents an oxygen atom, a sulfur atom which may be oxidized or a group of the formula:

NR$^8$ wherein R$^8$ represents a hydrogen atom, a hydrocarbon group which may be substituted or an acyl; and the other symbols have the same meanings as above, or a salt thereof, to alkylation or acylation and optionally followed by aryl-coupling of the resultant compound;

ii) subjecting a compound of the formula:

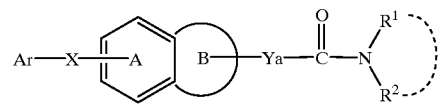

wherein Ya represents a group to be formed by removing a methylene from Y; and the other symbols have the same meanings as above, or a salt thereof, to reduction; or iii) subjecting a compound of the formula:

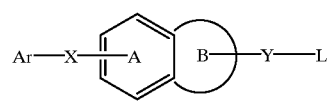

wherein L represents a leaving group; and the other symbols have the same meanings as above, to amination;

(30) an optical isomer of the compound of the formula:

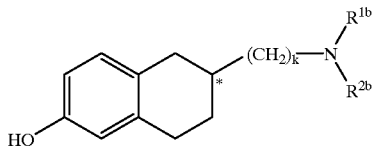

wherein $R^{1b}$ and $R^{2b}$ each represents methyl or ethyl, k represents 1 or 2, and * indicates the position of the asymmetric carbon, or a salt thereof;

(31) a pharmaceutical composition which comprises compound (I);

(32) a pharmaceutical composition of the above (31) which is an inhibitor for production and/or secretion of amyloid-β protein;

(33) a pharmaceutical composition of the above (31) which is for preventing and/or treating neurodegenerative diseases caused by amyloid-β protein;

(34) a pharmaceutical composition of the above (32), wherein the neurodegenerative disease caused by amyloid-β protein is Alzheimer's disease;

(35) a method of inhibiting production and/or secretion of amyloid-β protein in mammal, which comprises administering to said mammal an effective amount of compound (I) or a pharmaceutically acceptable salt thereof with a pharmaceutically acceptable excipient, carrier or diluent;

(36) a use of compound (I) for manufacturing a pharmaceutical composition for inhibiting production and/or secretion of amyloid-β protein;

(37) an inhibitor for production and/or secretion of amyloid-β protein, which comprises compound (I');

(38) a method of inhibiting production and/or secretion of amyloid-β protein in mammal, which comprises administering to said mammal an effective amount of compound (I') or a pharmaceutically acceptable salt thereof with a pharmaceutically acceptable excipient, carrier or diluent;

(39) a use of compound (I') for manufacturing a pharmaceutical composition for inhibiting production and/or secretion of amyloid-β protein, and so forth.

In the above-mentioned formulae, the "aromatic ring assembly group" of the "aromatic ring assembly group which may be substituted" for Ar is meant to indicate a group which is derived, by removing an optional hydrogen atom from an assembled aromatic ring in which two or more, preferably two or three aromatic rings are directly joined to each other by single bond(s) and the number of such direct ring junctions is one less than the number of the aromatic rings involved. The "aromatic ring" includes, for example, an aromatic hydrocarbon, an aromatic heterocyclic ring, etc.

The "aromatic hydrocarbon" includes, for example, a $C_{6-14}$ monocyclic or fused polycyclic (preferably, bi-or tri-cyclic) aromatic hydrocarbon compound (e.g., benzene, naphthalene, indene, anthracene, etc.) or a $C_{6-14}$ quinone (e.g., p-benzoquinone, 1,4-naphthoquinone, indan-4,7-dione, etc.), etc.

The "aromatic heterocyclic ring" includes, for example, 5- to 14-membered, preferably 5- to 10-membered aromatic heterocyclic rings containing one or more (e.g., 1 to 4) hetero atoms selected from the group consisting of nitrogen, sulfur and oxygen atoms in addition to carbon atoms, etc. Concretely mentioned is an aromatic heterocyclic ring, such as thiophene, benzothiophene, benzofuran, benzimidazole, benzoxazole, benzothiazole, benzisothiazole, naphtho[2,3-b]thiophene, furan, phenoxathlin, pyrrole, imidazole, pyrazole, oxadiazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc.; and a ring as formed through condensation of the above ring, preferably monocyclic ring, with one or more, preferably one or two aromatic rings (e.g., benzene ring, etc.), etc.

The assembly of those aromatic rings in which the rings are directly bonded to each other via a single bond includes, for example, those to be composed of two or three, preferably two aromatic rings selected from the group consisting of benzene ring, naphthalene ring and 5- to 10-membered (preferably 5- or 6-membered) aromatic heterocyclic ring. As specific examples of the assembly of such aromatic rings, mentioned are biphenyl, 2-phenylnaphthalene, p-terphenyl, o-terphenyl, m-terphenyl, 2-phenylpyridine, 3-phenylpyridine, 4-phenylpyridine, 2-phenylthiophene, 3-phenylthiophene, 2-phenylindole, 3-phenylindole, 5-phenyl-1,3,4-oxadiazole, etc. Among others, preferred is an assembly which is composed of two or three aromatic rings selected from the group consisting of benzene, thiophene, pyridine, pyrimidine, 1,2,4-oxadiazole, 1,3,4-oxadiazole, naphthalene and benzofuran.

Specific examples of the above "aromatic ring assembly group" are 2-biphenylyl, 3-biphenylyl, 4-biphenylyl, 4-(2-thienyl)phenyl, 4-(3-thienyl)phenyl, 3-(3-pyridyl)phenyl, 4-(3-pyridyl)phenyl, 6-phenyl-3-pyridyl, 5-phenyl-1,3,4-oxadiazol-2-yl, 4-(2-naphthyl) phenyl, 4-(2-benzofuranyl) phenyl, etc. Of those, preferred are 2-biphenylyl, 3-biphenylyl, 4-biphenylyl, etc. , especially preferred is 4-biphenylyl.

The "substituent" for the "aromatic ring assembly group which may be substituted" includes, for example, halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), 5- to 7-membered saturated cyclic amino, acyl, acylamino, acyloxy, $C_{6-10}$ aryloxy (e.g., phenyloxy, naphthyloxy, etc.), and so forth.

The "aromatic ring assembly group" may have 1 to 5, preferably 1 to 3 substituents as mentioned above at possible positions of the aromatic ring assembly group, and when the number of substituents is two or more, those substituents may be the same as or different from one another.

The above-mentioned "optionally halogenated $C_{1-6}$ alkyl" includes, for example, $C_{1-6}$ alkyl (e.g., methyl, ethyl, propyl, isopropyl, butyl, isobutyl, sec-butyl, tert-butyl, pentyl, hexyl, etc.) optionally having 1 to 5, preferably 1 to 3 halogen atoms (e.g., fluoro, chloro, bromo, iodo, etc.). Thus, for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. can be mentioned.

The above-mentioned "optionally halogenated $C_{3-6}$ cycloalkyl" includes, for example, $C_{3-6}$ cycloalkyl (e.g., cyclopropyl, cyclobutyl, cyclopentyl, cyclohexyl, etc.) optionally having 1 to 5, preferably 1 to 3 halogen atoms (e.g., fluoro, chloro, bromo, iodo, etc.). Thus, for example, cyclopropyl, cyclobutyl, cyclopentyl, cyclohexyl, 4,4-dichlorocyclohexyl, 2,2,3,3-tetrafluorocyclopentyl, 4-chlorocyclohexyl, etc. can be mentioned.

The above-mentioned "optionally halogenated $C_{1-6}$ alkoxy" includes, for example, $C_{1-6}$ alkoxy (e.g., methoxy, ethoxy, propoxy, butoxy, pentyloxy, etc.) optionally having 1 to 5, preferably 1 to 3 halogen atoms (e.g., fluoro, chloro, bromo, iodo, etc.). Thus, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. can be mentioned.

The above-mentioned "optionally halogenated $C_{1-6}$ alkylthio" includes, for example, $C_{1-6}$ alkylthio (e.g., methylthio, ethylthio, propylthio, isopropylthio, butylthio, sec-butylthio, tert-butylthio, etc.) optionally having 1 to 5, preferably 1 to 3 halogen atoms (e.g., fluoro, chloro, bromo, iodo, etc.). Thus, for example, methylthio, difluoromethylthio, trifluoromethylthio, ethylthio, propylthio, isopropylthio, butylthio, 4,4,4-trifluorobutylthio, pentylthio, hexylthio, etc. can be mentioned.

The above-mentioned "5- to 7-membered saturated cyclic amino" includes, for example, morpholino, thiomorpholino, piperazin-1-yl, 4-substituted piperazin-1-yl, piperidino, pyrrolidin-1-yl, hexamethyleneimin-1-yl, etc.

The "substituent" for the "4-substituted piperazin-1-yl" includes, for example, $C_{1-6}$ alkyl, $C_{6-14}$ aryl which may be substituted, $C_{7-19}$ aralkyl which may be substituted, 5- to 10-membered aromatic heterocyclic group which may be substituted, acyl, and so forth.

The "$C_{6-14}$ aryl" of the "$C_{6-14}$ aryl which may be substituted" includes, for example, phenyl, 1-naphthyl, 2-naphthyl, 2-indenyl, 2-anthryl, etc. Preferred is phenyl.

The "$C_{7-19}$ aralkyl" of the "$C_{7-19}$ aralkyl which may be substituted" includes, for example, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc. Preferred is benzyl, etc.

The "5- to 10-membered aromatic heterocyclic group" of the "5- to 10-membered aromatic heterocyclic group which may be substituted" includes, for example, 2-, 3- or 4-pyridyl, 1-, 2- or 3-indolyl, 2- or 3-thienyl, etc. Preferred is 2-, 3- or 4-pyridyl, etc.

The "substituent" which those "$C_{6-14}$ aryl which may be substituted", "$C_{7-19}$ aralkyl which may be substituted" and "5- to 10-membered aromatic heterocyclic group which may be substituted" respectively may have, includes, for example, 1 to 5 substituents selected from the group consisting of halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), carboxy, and so forth.

The "optionally halogenated $C_{1-6}$ alkyl", "optionally halogenated $C_{3-6}$ cycloalkyl", "optionally halogenated $C_{1-6}$ alkoxy" and "optionally halogenated $C_{1-6}$ alkylthio" include those described above, respectively.

The "acyl" of (i) "acyl" exemplified as substituents for the above "4-substituted piperazin-1-yl", (ii) "acyl" exemplified as substituents for the above "aromatic ring assembly group which may be substituted", (iii) the above "acylamino" and (iv) the above "acyloxy" includes, for example, an acyl represented by the formula:

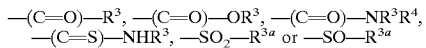

$-(C=O)-R^3, -(C=O)-OR^3, -(C=O)-NR^3R^4,$
$-(C=S)-NHR^3, -SO_2-R^{3a}$ or $-SO-R^{3a}$ wherein $R^3$ represents hydrogen, a hydrocarbon group which may be substituted or a heterocyclic group which may be substituted, $R^{3a}$ represents a hydrocarbon group which may be substituted or a heterocyclic group which may be substituted, $R^4$ represents hydrogen or $C_{1-6}$ alkyl, or $R^3$ and $R^4$ may, together with the adjacent nitrogen atom, form a nitrogen-containing heterocyclic ring.

The "hydrocarbon group" of the "hydrocarbon group which may be substituted" for $R^3$ or $R^{3a}$ means a group formed by removing an optional hydrogen atom from a hydrocarbon compound, as exemplified by acyclic or cyclic hydrocarbon group such as alkyl, alkenyl, alkynyl, cycloalkyl, aryl and aralkyl. Among them, the following $C_{1-16}$ acyclic or cyclic hydrocarbon group is preferable:
a) $C_{1-6}$ alkyl (e.g., methyl, ethyl, propyl, isopropyl, butyl, isobutyl, sec-butyl, tert-butyl, pentyl, hexyl, etc.),
b) $C_{2-6}$ alkenyl (e.g., vinyl, allyl, isopropenyl, butenyl, isobutenyl, sec-butenyl, etc.),
c) $C_{2-6}$ alkynyl (e.g., ethynyl, propargyl, butynyl, 1-hexynyl, etc.),
d) $C_{3-6}$ cycloalkyl (e.g., cyclopropyl, cyclobutyl, cyclopentyl, cyclohexyl, etc.), and the $C_{3-6}$ cycloalkyl being optionally condensed with one benzene ring,
e) $C_{6-14}$ aryl (e.g., phenyl, 1-naphthyl, 2-naphthyl, 2-indenyl, 2-anthryl, etc.), preferably phenyl,
f) $C_{7-19}$ aralkyl (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.), preferably benzyl.

Among others, $C_{1-6}$ alkyl, $C_{6-14}$ aryl and $C_{7-19}$ aralkyl are preferable.

Examples of the "substituent" for the "hydrocarbon group which may be substituted" include halogen atoms (e.g., fluoro, chloro, bromo, iodo, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, etc.), di-$C_{1-6}$ alkylamino (e.g., dimethylamino, diethylamino, ethylmethylamino, etc.), acyl, acylamino, acyloxy, 5- to 7-membered saturated cyclic amino, sulfo, aromatic group which may be substituted, and so forth.

The "hydrocarbon group" may have 1 to 5, preferably 1 to 3 substituents as mentioned above at possible positions of the hydrocarbon group and, when the number of substituents is two or more, those substituents may be the same as or different from one another.

The above-mentioned "aromatic group which may be substituted" includes "aromatic group which may be substituted" for Ar' described hereinafter.

The "optionally halogenated $C_{1-6}$ alkyl", "optionally halogenated $C_{3-6}$ cycloalkyl", "optionally halogenated $C_{1-6}$ alkoxy", "optionally halogenated $C_{1-6}$ alkylthio", "5- to 7-membered saturated cyclic amino", "acyl", "acylamino" and "acyloxy" mentioned above include, for example, those described in detail in the foregoing referring to the "substituents" for the "hydrocarbon group which may be substituted".

Of these, preferred "acyl" for "acyl", "acylamino" and "acyloxy" mentioned above is a group of the formula:

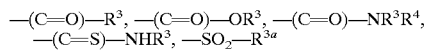

or

where $R^3$ is (i) hydrogen,
(ii) a hydrocarbon group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and sulfo, or
(iii) a heterocyclic group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and $C_{6-10}$ aryloxy; and $R^{3a}$ is
(i) a hydrocarbon group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and sulfo, or
(ii) a heterocyclic group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and $C_{6-10}$ aryloxy.

The "heterocyclic group" of the "heterocyclic group which may be substituted" for $R^3$ or $R^{3a}$ includes, for example, a monovalent group formed by removing an optional hydrogen atom from a 5- to 14-membered (monocyclic, bicyclic or tricyclic) heterocyclic ring containing 1 to 4 hetero atoms of 1 or 2 species selected from the group consisting of nitrogen, oxygen and sulfur atoms in addition to carbon atoms, preferably, (i) a 5- to 14-membered, preferably 5- to 10-membered aromatic heterocyclic ring, (ii) a 5- to 10-membered non-aromatic heterocyclic ring or (iii) a 7- to 10-membered bridged heterocyclic ring.

The above-mentioned "5- to 14-membered, preferably 5- to 10-membered aromatic heterocyclic ring" includes, for example, an aromatic heterocyclic ring such as thiophene, benzothiophene, benzofuran, benzimidazole, benzoxazole, benzothiazole, benzisothiazole, naphtho[2,3-b]thiophene, furan, phenoxathiine, pyrrole, imidazole, pyrazole, oxadiazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc.; and a ring as formed through condensation of those rings, preferably a monocyclic ring, with one or more, preferably one or two aromatic rings (e.g., benzene ring, etc.), etc.

The above-mentioned "5- to 10-membered non-aromatic heterocyclic ring" includes, for example, pyrrolidine, imidazoline, pyrazolidine, pyrazoline, piperidine, piperazine, morpholine, thiomorpholine, etc.

The above-mentioned "7- to 10-membered bridged heterocyclic ring" includes, for example, quinuclidine, 7-azabicyclo[2,2,1]heptane, etc.

Preferable examples of the "heterocyclic group" include, for example, a 5- to 10-membered (monocyclic or bicyclic) heterocyclic group containing 1 to 4 hetero atoms of 1 or 2 species selected from the group consisting of nitrogen, oxygen and sulfur atoms in addition to carbon atoms. Concretely mentioned are an aromatic heterocyclic group such as 2- or 3-thienyl, 2-, 3- or 4-pyridyl, 2- or 3-furyl, 2-, 3-, 4-, 5- or 8-quinolyl, 4-isoquinolyl, pyrazinyl, 2- or 4-pyrimidinyl, 3-pyrrolyl, 2-imidazolyl, 3-pyridazinyl, 3-isothiazolyl, 3-isoxazolyl, 1-indolyl, 2-indolyl, 2-isoindolylnyl, etc; and a non-aromatic heterocyclic group such as 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc.

Among these groups, a 5- or 6-membered heterocyclic group containing 1 to 3 hetero atoms selected from the group consisting of nitrogen, oxygen and sulfur atoms in addition to carbon atoms. Concretely mentioned are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholino, etc.

The "heterocyclic group which may be substituted" may have 1 to 5, preferably 1 to 3 substituents which the "aromatic ring assembly group which may be substituted" mentioned above may have. When the number of substituents is two or more, those substituents may be the same as or different from one another.

In the case that the "substituent" for the above "heterocyclic group which may be substituted" is "acyl", "acylamino" or "acyloxy", preferred "acyl" for these "acyl", "acylamino" or "acyloxy" is a group of the formula:

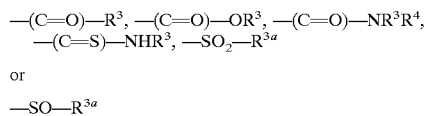

or

—SO—$R^{3a}$ where $R^3$ is
(i) hydrogen,
(ii) a hydrocarbon group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and sulfo, or
(iii) a heterocyclic group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and $C_{6-10}$ aryloxy; and $R^{3a}$ is
(i) a hydrocarbon group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and sulfo, or (ii) a heterocyclic group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and $C_{6-10}$ aryloxy.

The "$C_{1-6}$ alkyl" for $R^4$ includes, for example, methyl, ethyl, propyl, isopropyl, butyl, isobutyl, sec-butyl, tert-butyl, pentyl, hexyl, etc.

The "nitrogen-containing heterocyclic ring" formed by, taken together with the adjacent nitrogen atom, $R^3$ and $R^4$ includes, for example, a 5- to 7-membered nitrogen-containing heterocyclic ring having one nitrogen atom and optionally having 1 to 3 hetero atoms selected from the group consisting of nitrogen, oxygen and sulfur atoms in addition to carbon atoms. Such examples include piperidine, morpholine, thiomorpholine, piperazine, pyrrolidine, etc.

Preferably, the above "acyl" is, for example, formyl, carboxy, carbamoyl, $C_{1-6}$ alkyl-carbonyl (e.g., acetyl, propionyl, etc.), $C_{1-6}$ alkoxy-carbonyl (e.g., methoxycarbonyl, ethoxycarbonyl, propoxycarbonyl, tert-butoxycarbonyl, etc.), $C_{6-10}$ aryl-carbonyl (e.g., benzoyl, 1-naphthoyl, 2-naphthoyl, etc.), $C_{6-10}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocycle carbonyl (e.g., nicotinoyl, isonicotinoyl, 2-thenoyl, 3-thenoyl, 2-furoyl, 3-furoyl, morpholinocarbonyl, piperidinocarbonyl, 1-pyrrolidinylcarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-10}$ aryl-carbamoyl (e.g., phenylcarbamoyl, 1-naphthylcarbamoyl, 2-naphthylcarbamoyl, etc.), 5- or 6-membered heterocycle carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-10}$ arylsulfonyl (e.g., benzenesulfonyl, 1-naphthalenesulfonyl, 2-naphthalenesulfonyl, etc.), etc.

The above-mentioned "acylamino" includes, for example, an amino substituted by 1 or 2 "acyl" described in detail in the foregoing referring to the "substituents" for the "aromatic ring assembly group which may be substituted". Preferred is an acylamino of the formula:

—$NR^5COR^6$, —$NR^5COOR^{6a}$ or —$NR^5SO_2R^{6a}$ wherein $R^5$ represents hydrogen or $C_{1-6}$ alkyl, $R^6$ represents hydrogen, a hydrocarbon group which may be substituted or a heterocyclic group which may be substituted, and $R^{6a}$ represents a hydrocarbon group which may be substituted or a heterocyclic group which may be substituted.

The "$C_{1-6}$ alkyl" for $R^5$ includes the "$C_{1-6}$ alkyl" shown by $R^4$ above.

The "hydrocarbon group which may be substituted" and the "heterocyclic group which may be substituted" for $R^6$ or $R^{6a}$ include the "hydrocarbon group which may be substituted" and the "heterocyclic group which may be substituted" shown by $R^3$, respectively.

Preferred examples of the "acylamino" are formylamino, $C_{1-6}$ alkyl-carboxamido (e.g., acetamido, etc.), $C_{6-10}$ aryl-carboxamido (e.g., phenylcarboxamido, naphthylcarboxamido, etc.), $C_{1-6}$ alkoxy-carboxamido (e.g., methoxycarboxamido, ethoxycarboxamido, propoxycarboxamido, butoxycarboxamido, etc.), $C_{1-6}$ alkyl-sulfonylamino (e.g., methylsulfonylamino, ethylsulfonylamino, etc.), etc.

The above-mentioned "acyloxy" includes, for example, an oxy substituted by one "acyl" described in detail in the foregoing referring to the "substituents" for the "aromatic ring assembly group which may be substituted". Preferred is an acyloxy of the formula:

—O—$COR^7$, —O—$COOR^7$ or

—O—$CONHR^7$ wherein $R^7$ represents a hydrocarbon group which may be substituted or a heterocyclic group which may be substituted.

The "hydrocarbon group which may be substituted" and the "heterocyclic group which may be substituted" for $R^7$ include the "hydrocarbon group which may be substituted" and the "heterocyclic group which may be substituted" shown by $R^3$, respectively.

Preferred examples of the "acyloxy" are $C_{1-6}$ alkyl-carbonyloxy (e.g., acetoxy, propanoyloxy, etc.), $C_{6-10}$ aryl-carbonyloxy (e.g., benzoyloxy, 1-naphthoyloxy, 2-naphthoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-10}$ aryl-carbamoyloxy (e.g., phenylcarbamoyloxy, naphthylcarbamoyloxy, etc.), nicotinoyloxy, etc.

The "substituent" for the "aromatic ring assembly group which may be substituted" for Ar preferably includes halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino and formyl.

The "fused aromatic group" of the "fused aromatic group which may be substituted" for Ar is meant to indicate a monovalent group by removing an optional hydrogen atom from a fused polycyclic (preferably bi-cyclic to tetra-cyclic, more preferably bi-cyclic or tri-cyclic) aromatic ring. The "fused polycyclic aromatic ring" includes a fused polycyclic aromatic hydrocarbon group, a fused polycyclic aromatic heterocyclic ring, etc.

The "fused polycyclic aromatic hydrocarbon group" includes, for example, a fused polycyclic (preferably bi-cyclic or tri-cyclic) $C_{10-14}$ aromatic hydrocarbon group (e.g., naphthalene, indene, anthracene, etc.).

The "fused polycyclic aromatic heterocyclic ring" includes, for example, a 9- to 14-membered, preferably 9- or 10-membered fused polycyclic aromatic heterocyclic ring containing one or more (e.g., 1 to 4) hetero atoms selected from the group consisting of nitrogen, oxygen and sulfur atoms in addition to carbon atoms. Concretely mentioned is an aromatic heterocyclic ring such as benzofuran, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalimide, etc.

As specific examples of the "fused aromatic group", mentioned are 1-naphthyl, 2-naphthyl, 2-quinolyl, 3-quinolyl, 4-quinolyl, 2-benzofuranyl, 2-benzothiazolyl, 2-benzimidazolyl, 1-indolyl, 2-indolyl, 3-indolyl, etc. Preferred are 1-naphthyl and 2-naphthyl, etc.

For the "substituents" for the "fused aromatic group which may be substituted" and their number, referred to are the same as those mentioned above for the "aromatic ring assembly group which may be substituted" for Ar.

Ar is preferably an aromatic ring assembly group which may be substituted. Among others, the aromatic ring assembly group is preferably composed of two or three aromatic rings selected from the group consisting of benzene, thiophene, pyridine, pyrimidine, 1,2,4-oxadiazole, 1,3,4-oxadiazole, naphthalene and benzofuran. More preferred is 2-, 3- or 4-biphenylyl.

Preferred examples of Ar are aromatic ring assembly groups which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy. More preferred is a 2-, 3- or 4-biphenylyl (but even more preferably, 4-biphenylyl) which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy.

The "aromatic group" of the "aromatic group which may be substituted" for Ar' includes, for example, a monocyclic aromatic group, an aromatic ring assembly group, a fused aromatic group, etc. The "aromatic ring assembly group" and the "fused aromatic groups" are the same as those mentioned in detail hereinabove for the "aromatic ring assembly group" and the "fused aromatic groups" for Ar.

The "monocyclic aromatic group" includes, for example, a monovalent group by removing an optional hydrogen atom from a benzene ring or a 5- or 6-membered aromatic heterocyclic ring.

The "5- or 6-membered aromatic heterocyclic ring" includes, for example, a 5- or 6-membered aromatic heterocyclic ring containing one or more (e.g., 1 to 3) hetero atoms selected from the group consisting of nitrogen, oxygen and sulfur atoms in addition to carbon atoms. Concretely mentioned are thiophene, furan, pyrrole, imidazole, pyrazole, pyridine, pyrazine, pyrimidine, pyridazine, etc.

Specific examples of the "monocyclic aromatic group" are phenyl, 2- or 3-thienyl, 2- or 3-furyl, 1-, 2- or 3-pyrrolyl, 2- or 4-imidazolyl, 3- or 4-pyrazolyl, 2-, 3- or 4-pyridyl, 2-pyrazinyl, 2-, 4- or 5-pyrimidinyl, 3- or 4-pyridazinyl, etc.

The "substituents" for the "aromatic group which may be substituted" and their number are the same as those mentioned above for the "aromatic ring assembly group which may be substituted" for Ar.

Ar' is preferably an aromatic ring assembly group which may be substituted, or a fused aromatic group which may be substituted. More preferred is an aromatic ring assembly group which may be substituted.

The "$C_{1-6}$ alkylene" of the "$C_{1-6}$ alkylene which may be substituted by 1 to 3 substituents selected from the group consisting of oxo and $C_{1-6}$ alkyl" for X includes, for example, —CH$_2$—, —(CH$_2$)$_2$—, —(CH$_2$)$_3$—, —(CH$_2$)$_4$—, —(CH$_2$)$_5$—, —(CH$_2$)$_6$—, etc.

The "$C_{2-6}$ alkenylene" of the "$C_{2-6}$ alkenylene which may be substituted by 1 to 3 substituents selected from the group consisting of oxo and $C_{1-6}$ alkyl" for X includes, for example, —CH=CH—, —CH$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—, —CH$_2$—CH$_2$—CH$_2$—CH$_2$—CH=CH—, etc.

The "$C_{2-6}$ alkynylene" of the "$C_{2-6}$ alkynylene which may be substituted by 1 to 3 substituents selected from the group consisting of oxo and $C_{1-6}$ alkyl" for X includes, for example, —C≡C—, —CH$_2$—C≡C—, —CH$_2$—C≡C—CH$_2$—CH$_2$—, etc.

The above oxo and $C_{1-6}$ alkyl (e.g., methyl, ethyl, propyl, isopropyl, butyl, isobutyl, sec-butyl, tert-butyl, pentyl, hexyl, etc.) may be substituted at the substitutable positions. When the number of the substituents is two or more, those substituents may be the same as or different from one another.

The "hydrocarbon group which may be substituted" and the "acyl" for $R^8$ are the same as those mentioned in detail above. $R^8$ is preferably hydrogen, optionally halogenated $C_{1-6}$ alkyl, $C_{1-6}$ alkyl-carbonyl, etc.

X is preferably a $C_{1-6}$ alkylene (e.g., —CH$_2$—, —(CH$_2$)$_2$—, —(CH$_2$)$_3$—, —(CH$_2$)$_4$—, —(CH$_2$)$_5$—, —(CH$_2$)$_6$—, etc.); a group of the formula:

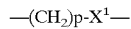

or

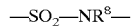

wherein each symbol is as defined above; etc. Of those, more preferably, $X^1$ is O or $NR^8$ (more preferably O); and $R^8$ is hydrogen or a $C_{1-3}$ alkyl-carbonyl (e.g., acetyl, etc.).

X is preferably a divalent $C_{1-6}$ aliphatic hydrocarbon group (e.g., $C_{1-6}$ alkylene, $C_{2-6}$ alkenylene, $C_{2-6}$ alkynylene, etc.) which may contain an oxygen atom, more preferably a $C_{1-3}$ alkylene, —CH$_2$—O—, etc.

The "divalent $C_{1-6}$ aliphatic hydrocarbon group which may contain an oxygen atom or a sulfur atom" of the "divalent $C_{1-6}$ aliphatic hydrocarbon group which may have an oxygen atom or a sulfur atom and may be substituted" for Y includes, for example, a saturated or unsaturated divalent $C_{1-6}$ aliphatic hydrocarbon group which may contain one or two, preferably one oxygen or sulfur atom at any position between carbon atoms or at the terminal. Concretely mentioned are a $C_{1-6}$ alkylene, a $C_{2-6}$ alkenylene, a $C_{2-6}$ alkynylene, a group of the formula:

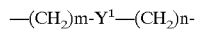

wherein —$Y^1$— represents —O—, —S—, —SO— or —SO$_2$—; m represents an integer of 0 to 4; n represents an integer of 1 to 5; and m+n is an integer of 1 to 5, etc. Preferred is a divalent $C_{1-6}$ aliphatic hydrocarbon group.

The above "$C_{1-6}$ alkylene", "$C_{2-6}$ alkenylene" and "$C_{2-6}$ alkynylene" are the same as those mentioned in detail above for the "$C_{1-6}$ alkylene", "$C_{2-6}$ alkenylene" and "$C_{2-6}$ alkynylene" for X.

The "substituent" for the "divalent $C_{1-6}$ aliphatic hydrocarbon group which may contain an oxygen atom or a sulfur atom and may be substituted" includes, for example, $C_{1-6}$ alkyl (e.g., methyl, ethyl, propyl, isopropyl, butyl, isobutyl, sec-butyl, tert-butyl, pentyl, hexyl, etc.), etc. One to three such substituents may be substituted at the substitutable positions of the divalent $C_{1-6}$ aliphatic hydrocarbon group. When the number of the substituents is two or more, those substituents may be the same as or different from one another.

Y is preferably a divalent $C_{1-6}$ aliphatic hydrocarbon group, more preferably a $C_{1-6}$ alkylene.

The "lower alkyl" of the "lower alkyl which may be substituted" for $R^1$ or $R^2$ includes, for example, $C_{1-6}$ alkyl (e.g., methyl, ethyl, propyl, isopropyl, butyl, isobutyl, sec-butyl, tert-butyl, pentyl, hexyl, etc.), etc. Preferred is methyl, ethyl and propyl.

The "lower alkyl group which may be substituted" may have 1 to 5, preferably 1 to 3 substituents, such as (1) those which the "aromatic ring assembly group which may be substituted" may have or (2) $C_{6-10}$ aryl. When the number of the substituents is two or more, those substituents may be the same as or different from one another.

The "nitrogen-containing heterocyclic ring" of the "nitrogen-containing heterocyclic ring which may be substituted" to be formed by $R^1$ and $R^2$ along with the adjacent nitrogen atom includes, for example, a 3- to 8-membered nitrogen-containing heterocyclic ring having one nitrogen atom and optionally having 1 to 3 hetero atoms selected from the group consisting of nitrogen, oxygen and sulfur atoms in addition to carbon atoms. Concretely mentioned are aziridine, azetidine, morpholine, thiomorpholine, piperidine, piperazine, pyrrolidine, hexamethyleneimine, heptamethyleneimine, as well as unsaturated cyclic amines corresponding to those rings (e.g., 1,2,5,6-tetrahydropyridine, etc.), etc. Of those, preferred are morpholine, piperidine, piperazine, pyrrolidine, etc.

The "nitrogen-containing heterocyclic ring which may be substituted" may have 1 to 3 substituents selected from the group consisting of (1) "substituents" for the "hydrocarbon group which may be substituted", (2) oxo and (3) $C_{7-19}$ aralkyl. Preferred examples of the substituents are $C_{1-6}$ alkyl (e.g., methyl, ethyl, propyl, isopropyl, butyl, etc.), hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), 5- to 7-membered cyclic amino (e.g., morpholino, piperazin-1-yl, piperidino, pyrrolidin-1-yl, hexamethylenimin-1-yl, etc.), $C_{1-6}$ alkyl-carboxamido (e.g., acetamido, etc.), $C_{1-6}$ alkoxy-carboxamido (e.g., methoxycarboxamido, ethoxycarboxamido, etc.), aromatic group which may be substituted (e.g., a $C_{6-10}$ aryl (preferably, phenyl or 1- or 2-naphthyl) or 5- or 6-membered aromatic heterocyclic group (preferably, 2-, 3- or 4-pyridyl), each of which group may be substituted by 1 to 3 substituents selected from the group consisting of halogen atoms, cyano, $C_{1-6}$ alkyl and $C_{1-6}$ alkoxy, etc.), oxo, etc.

$R^1$ and $R^2$ each is preferably $C_{1-6}$ alkyl.
The "group of the formula:

—X—Ar"

is substituted at the substitutable position of Ring A. The "substituent" for the "benzene ring which may be further substituted apart from the group of the formula:

—X—Ar wherein each symbol is as defined above" for Ring A includes, for example, halogen atoms (e.g., fluoro, chloro, bromo, iodo, etc.), optionally halogenated $C_{1-6}$ alkyl, optionally halogenated $C_{1-6}$ alkoxy, hydroxy, amino, etc. The "optionally halogenated $C_{1-6}$ alkyl" and the "optionally halogenated $C_{1-6}$ alkoxy" are the same as those mentioned in detail above for the "optionally halogenated $C_{1-6}$ alkyl" and the "optionally halogenated $C_{1-6}$ alkoxy" for Ar.

One to three such substituents may be substituted at the substitutable positions of Ring A. When the number of the substituents is two or more, those substituents may be the same as or different from one another.

Ring A is preferable a benzene ring substituted by the group of the formula:

—X—Ar wherein each symbol is as defined above.
The "group of the formula:

—Y—$NR^1R^2$"

is substituted at the substitutable position of Ring B. The "4- to 8-membered ring" of the "4- to 8-membered ring which may be further substituted apart from the group of the formula:

—Y—$NR^1R^2$ wherein each symbol is as defined above" for Ring B may have one double bond apart from the part at which Ring B is condensed with Ring A, and includes a 4- to 8-membered carbocyclic or heterocyclic ring which may contain 1 to 3 hetero atoms selected from the group consisting of nitrogen, oxygen and sulfur atoms in addition to carbon atoms. Specific examples of those rings, mentioned is a ring of the formula:

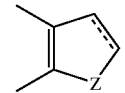

wherein ----- represents a single bond or a double bond; and Z represents (i) a bond, (ii) a $C_{1-4}$ alkylene, (iii) a $C_{2-4}$ alkenylene, (iv) —O—$CH_2$—, (v) —O—$CH_2$—$CH_2$— or (vi) a group of the formula:

—$NR^{8a}$—$CH_2$— or

—$NR^{8a}$—$CH_2$—$CH_2$— wherein $R^{8a}$ has the same meaning as $R^8$.

$R^{8a}$ is preferably hydrogen, optionally halogenated $C_{1-6}$ alkyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, etc. More preferred is hydrogen, optionally halogenated $C_{1-6}$ alkyl, $C_{1-6}$ alkyl-carbonyl, $C_{1-3}$ alkylsulfonyl, etc.

Z is preferably $C_{1-3}$ alkylene, —$NR^{8a}$—$CH_2$—, etc. More preferably, it is ethylene.

The "4- to 8-membered ring" is preferably a 4- to 8-membered ring of the formula:

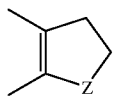

wherein Z has the same meanings as above. More preferred is a 6-membered carbocyclic or heterocyclic ring which does not have any double bond apart from the part at which it is condensed with Ring A, and which may have one oxygen atom or imino in addition to carbon atoms.

The "substituent" for the "4- to 8-membered ring which may be further substituted apart from the group of the formula:

wherein each symbol is as defined above" includes, for example, oxo, $C_{1-6}$ alkyl (e.g., methyl, ethyl, propyl, isopropyl, butyl, isobutyl, sec-butyl, tert-butyl, pentyl, hexyl, etc.), etc. One to three such substituents may be substituted at the substitutable positions of the ring. When the number of the substituents is two or more, those substituents may be the same as or different from one another.

Ring B is preferably a 6-membered carbocyclic or heterocyclic ring substituted by the group of the formula:

wherein each symbol is as defined above. More preferably Ring B is a ring of the formula:

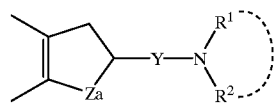

wherein Za represents $C_{1-3}$ alkylene or a group of the formula:

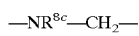

wherein $R^{8c}$ is hydrogen, optionally halogenated $C_{1-6}$ alkyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl; and the other symbols have the same meanings as above. Of those, Za is preferably ethylene.

The fused ring to be formed by Ring A and Ring B is preferably a ring of the formula:

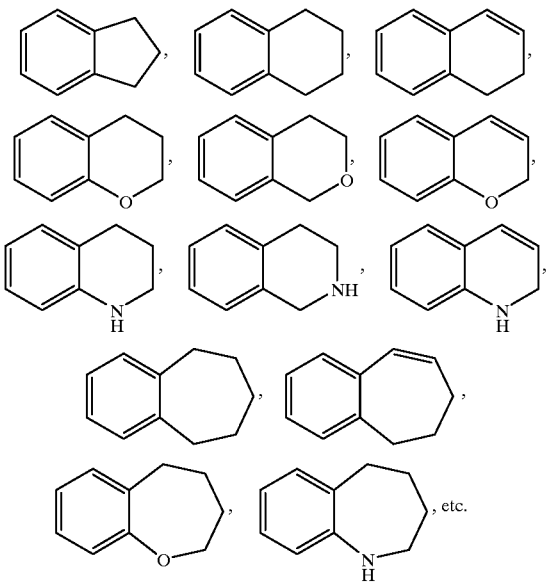

In compounds (I) and (I'), preferred is a compound wherein Ar and Ar' each is an aromatic ring assembly group (preferably 2-, 3- or 4-biphenylyl) which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl and $C_{1-6}$ alkyl-carboxamido;

X is $C_{1-3}$ alkylene which may contain an oxygen atom;

Y is $C_{1-6}$ alkylene;

$R^1$ and $R^2$ each is $C_{1-6}$ alkyl;

Ring A is a benzene ring substituted by the group of the formula:

wherein each symbol is as defined above; and

Ring B is a 6-membered carbocyclic or heterocyclic ring substituted by the group of the formula:

wherein each symbol is as defined above.

More preferred is a compound of the formula:

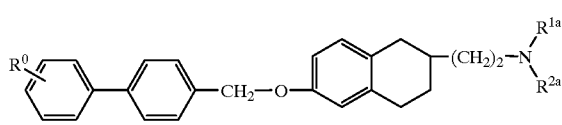

wherein $R^0$ is 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl and $C_{1-6}$ alkyl-carboxamido; and $R^{1a}$ and $R^{2a}$ each is $C_{1-6}$ alkyl.

Also preferred is a compound of the formula:

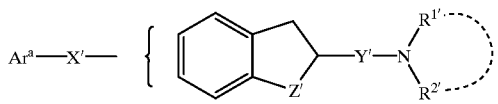

wherein $Ar^a$ is (i) 2, 3- or 4-biphenylyl which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, amino, formyl and $C_{1-6}$ alkyl-carboxamido, (ii) 4-(2-thienyl) phenyl or 4-(3-thienyl) phenyl, (iii) 4-(3-pyridyl)phenyl, (iv) 6-phenyl-3-pyridyl which may be substituted by a $C_{1-6}$ alkoxy, (v) 5-phenyl-1,3,4-oxadiazol-2-yl, (vi) 4-(2-naphthyl) phenyl, (vii) 4-(2-benzofuranyl)phenyl, (viii) 1- or 2-naphthyl, (ix) 2-quinolyl, (x) 2-benzothiazolyl or (xi) 2-benzofuranyl;

X' is —CH$_2$—O—, —SO$_2$—NH— or a group of the formula:

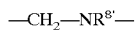

wherein $R^{8'}$ is hydrogen or $C_{1-3}$ alkyl-carbonyl;
Y' is $C_{1-6}$ alkylene;
Z' is —CH$_2$—CH$_2$— or a group of the formula:

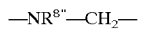

wherein $R^{8''}$ is hydrogen, $C_{1-3}$ alkyl, $C_{1-3}$ alkyl-carbonyl or $C_{1-3}$ alkylsulfonyl; and
$R^{1'}$ and $R^{2'}$ each is $C_{1-6}$ alkyl which may be substituted by 1 to 5 substituents selected from the group consisting of di-$C_{1-3}$ alkylamino, $C_{1-3}$ alkoxy-carbonyl and phenyl, or
$R^{1'}$ and $R^{2'}$ form, taken together with the adjacent nitrogen atom, a pyrrolidin-1-yl, piperidino or piperazin-1-yl which may be substituted by 1 to 3 substituents selected from the group consisting of hydroxy, $C_{1-3}$ alkoxy-carbonyl, piperidino, phenyl and benzyl.

Especially preferred are 6-(4-biphenylyl)methoxy-2-[2-(N,N-dimethylamino) ethyl]tetralin,
6-(4-biphenylyl)methoxy-2-(N,N-dimethylamino) methyltetralin,
2-(N,N-dimethylamino)methyl-6-(4'-methoxybiphenyl-4-yl) methoxytetralin,
(+)-6-(4-biphenylyl)methoxy-2-[2-(N,N-dimethylamino) ethyl]tetralin,
(+)-6-(4-biphenylyl)methoxy-2-[2-(N,N-diethylamino) ethyl]tetralin,
(+)-2-[2-(N,N-dimethylamino)ethyl]-6-(4'-methylbiphenyl-4-yl) methoxytetralin,
(+)-2-[2-(N,N-dimethylamino)ethyl]-6-(4'-methoxybiphenyl-4-yl) methoxytetralin,
(+)-6-(2',4'-dimethoxybiphenyl-4-yl)methoxy-2-[2-(N,N-dimethylamino) ethyl]tetralin,
(+)-6-[4-(1,3-benzodioxol-5-yl)phenyl]methoxy-2-[2-(N,N-dimethylamino) ethyl]tetralin,
(+)-6-(3',4'-dimethoxybiphenyl-4-yl)methoxy-2-[2-(N,N-dimethylamino) ethyl]tetralin and salts thereof.

As the salts of compound (I) and compound (I'), for example, inorganic salts, ammonium salts, salts with organic bases, salts with inorganic acids, salts with organic acids and salts with basic or acidic amino acids can be mentioned. Preferable examples of inorganic salts include alkali metal salts such as sodium salt and potassium salt; alkaline earth metal salts such as calcium salts, magnesium salts and barium salts; aluminum salts, etc. Preferred salts with organic bases are exemplified by salts with trimethylamine, triethylamine, pyridine, picoline, ethanolamine, diethanolamine, triethanolamine, dicyclohexylamine, N,N'-dibenzylethylenediamine, etc. Preferred salts with inorganic acids are exemplified by salts with hydrochloric acid, hydrobromic acid, nitric acid, sulfuric acid, phosphoric acid, etc. Preferred salts with organic acids are exemplified by salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferred salts with basic amino acids are exemplified by salts with arginine, lysine, ornithine, etc. Preferred salts with acidic amino acids are exemplified by salts with aspartic acid, glutamic acid, etc.

Among others, pharmaceutically acceptable salts are preferable. Preferable examples include, for example, when compound (I) or (i') has a acidic functional group, alkali metal salts (e.g., sodium salt, potassium salt, etc.), alkaline earth metal salts (e.g., calcium salt, magnesium salt, barium salt, etc.), and ammonium salts; and when compound (I) or (I') has a basic functional group, inorganic salts such as hydrochloride, sulfate, phosphate and hydrobromide, or, organic salts such as acetate, maleate, fumarate, succinate, methanesulfonate, p-toluenesulfonate, citrate and tartrate.

Process for producing compound (I) is mentioned below.

Compound (I) can be produced by any per se known means, for example, by the following processes 1 to 4, etc. Compound (I') can be produced in accordance with the production of compound (I).

Compounds described in the following processes 1 to 4 include their salts. For their salts, for example, referred to are the same as the salts of compound (I).

"Room temperature" is meant to indicate a temperature falling between 0° C. and 30° C.

For example, compound (I) wherein X contains an oxygen atom, a sulfur atom which may be oxidized (S, SO or SO$_2$) or a group of the formula:

wherein $R^{8a}$ has the same meanings as above, is produced according to the methods mentioned below. Other compound (I) wherein X contains none of an oxygen atom, a sulfur atom which may be oxidized and a group of the formula:

wherein $R^{8a}$ has the same meanings as above, can also be produced in the same manner.

Unless otherwise specifically indicated, the symbols in the chemical structures in the schemes mentioned below have the same meanings as above.

Process 1

Scheme 1

HXa—A—B—Y—N(R¹)(R²)  (II)

Step 1: Ar—Xb—L

Ar—Xb—Xa—A—B—Y—N(R¹)(R²)  (Ia)

In those formulae, Xa represents an oxygen atom, a sulfur atom which may be oxidized or a group of the formula:

NR$^{8a}$ wherein R$^{8a}$ has the same meanings as above.

Step 1

Compound (II) is subjected to alkylation or acylation to obtain compound (Ia).

The "alkylation" and "acylation" may be effected in any per se known manner, for example, according to the methods described in Organic Functional Group Preparations, 2nd Ed., Academic Press Inc., 1989.

Concretely, compound (II) is reacted with a compound of the formula:

Ar—Xb-L wherein Xb represents a group formed by removing Xa from X, and L represents a leaving group or a hydroxy, to obtain compound (Ia).

The "leaving group" for L includes, for example, halogen atoms (e.g., chloro, bromo, iodo, etc.), optionally halogenated $C_{1-6}$ alkylsulfonyloxy (e.g., methanesulfonyloxy, ethanesulfonyloxy, trifluoromethanesulfonyloxy, etc.), $C_{6-10}$ arylsulfonyloxy which may be substituted, etc. The "substituent" for the "$C_{6-10}$ arylsulfonyloxy which may be substituted" includes, for example, 1 to 3 substituents selected from the group consisting of halogen atoms, optionally halogenated $C_{1-6}$ alkyl and optionally halogenated $C_{1-6}$ alkoxy. Specific examples of the "$C_{6-10}$ arylsulfonyloxy which may be substituted" are benzenesulfonyloxy, p-toluenesulfonyloxy, 1-naphthalenesulfonyloxy, 2-naphthalenesulfonyloxy, etc.

Compound (II) can be produced in any per se known manner, for example, according to the methods of the following schemes 2 to 4 or analogous methods thereto.

In the case that L is a leaving group, for example, compound (II) is reacted with an equivalent amount or an excessive amount of a compound of the formula:

Ar—Xb-L wherein each symbol is as defined above, in an inert solvent. If desired, a base is added to the reaction system. Where Xa is a group of the formula:

NR$^{8a}$ wherein R$^{8a}$ has the same meanings as above, the addition of the base is not always indispensable.

The reaction temperature falls between −20° C. and 100° C., preferably between room temperature (0° C. to 30° C.) and 80° C. The reaction time falls between 0.5 hours and 1 day.

The inert solvent includes, for example, alcohols, ethers, halogenated hydrocarbons, aromatic solvents, nitrites, amides, ketones, sulfoxides, water, etc., which may be used either singly or as a suitable mixture of two or more species. Of those, preferred are acetonitrile, N,N-dimethylformamide (DMF), acetone, ethanol, pyridine, etc.

The "base" includes, for example;

(1) strong bases such as alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium diisopropylamide, lithium dicyclohexylamide, lithium hexamethylsilazide, sodium hexamethylsilazide, potassium hexamethylsilazide, etc.), alkali metal or alkaline earth metal lower-alkoxides (e.g., sodium methoxide, sodium ethoxide, potassium tert-butoxide, etc.), etc.;

(2) inorganic bases such as alkali metal or alkaline earth metal hydroxides (e.g., sodium hydroxide, potassium hydroxide, lithium hydroxide, barium hydroxide, etc.), alkali metal or alkaline earth metal carbonates (e.g., sodium carbonate, potassium carbonate, cesium carbonate, etc.), alkali metal or alkaline earth metal hydrogencarbonates (e.g., sodium hydrogencarbonate, potassium hydrogencarbonate, etc.), etc.; or (3) organic bases such as amines e.g., triethylamine, diisopropylethylamine, N-methylmorpholine, dimethylaminopyridine, DBU (1,8-diazabicyclo[5.4.0]-7-undecene), DBN (1,5-diazabicyclo[4.3.0]non-5-ene), etc., basic heterocyclic compounds, e.g., pyridine, imidazole, 2,6-lutidine, etc.

Preferably, the alkylation is effected by stirring compound (II) with 1 to 2 equivalents of a compound of the formula:

Ar—Xb-L wherein each symbol is as defined above, and 1 to 5 equivalents of a base (e.g., potassium carbonate, sodium hydride, sodium hydroxide, etc.), in acetonitrile or DMF, for 1 to 20 hours. The preferred reaction temperature varies, depending on the base used. For example, when sodium hydride is used, the reaction temperature is preferably room temperature; and when potassium carbonate is used, the preferred reaction temperature falls between room temperature and 80° C.

The acylation is preferably effected by stirring compound (II) with 1 to 1.5 equivalents of a compound of the formula:

Ar—Xb-L wherein each symbol is as defined above, and 1 to 5 equivalents of a base (e.g., sodium hydride, sodium hydroxide, potassium carbonate, sodium hydrogencarbonate, triethylamine, etc.), in an inert solvent (e.g., single or mixed solvent of water, ethyl acetate, DMF, acetonitrile and/or pyridine), at room temperature for 1 to 6 hours.

In the case that L is a hydroxy group, compound (II) is subjected to Mitsunobu reaction.

The Mitsunobu reaction may be attained, for example, by stirring compound (II) with 1 to 3 equivalents, preferably from 1.1 to 2 equivalents of a compound of the formula:

Ar—Xb-L wherein each symbol is as defined above, in the presence of 1 to 2 equivalents of a triarylphosphine (e.g., triphenylphosphine, etc.) and 1 to 2 equivalents of DEAE (diethyl azodicarboxylate) in an inert solvent, for 1 to 24 hours.

The inert solvent includes, for example, ethers, etc. Preferred is tetrahydrofuran (THF).

Scheme 2

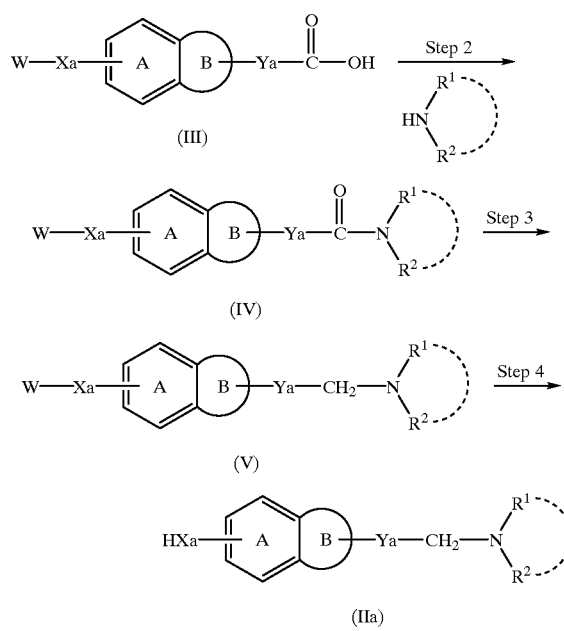

In those formulae, W represents a hydrogen atom or a protective group; and Ya represents a group formed by removing a methylene from Y.

For the "protective group" for W, referred to are the same as those for the "protective group for hydroxy group" which will be mentioned hereinafter. W is preferably a $C_{1-6}$ alkyl or a benzyl which may be substituted.

Step 2

Compound (III) is subjected to amidation to obtain compound (IV).

Compound (III) is an easily-available known compound. Examples for the production of compound (II) are disclosed in JP-A-2-96552, JP-A-6-206851, J. Med. Chem., 1326 (1989), etc.

The production of some specific examples of compound (III) wherein Xa is-an oxygen atom and W is a methyl, is disclosed in other references. For example, (1) methods for producing 1,2,3,4-tetrahydro-6-methoxynaphthalene-2-acetic acid are disclosed in Synthetic Communications 11, 803–809 (1981), etc.; and (2) methods for producing 1,2,3,4-tetrahydro-6-methoxynaphthalene-2-carboxylic acid and 1,2,3,4-tetrahydro-6-methoxynaphthalene-2-butyric acid are disclosed in J. Chem. Soc. Perkin Trans. I, 1889–1893 (1976), etc.

The production or some other examples of compound (III) wherein Xa is an imino and W is hydrogen, 6-amino-1,2,3,4-tetrahydronaphthalene-2-carboxylic acid and its ethyl ester is disclosed in Zhur. Obshch. Khim., p. 1446 (1952), etc.

In other case that compound (III) which is 7-methoxy-2-oxo-1,2,3,4-tetrahydroquinoline-3-acetic acid or 8-methoxy-2-oxo-2,3,4,5-tetrahydro-1H-1-benzazepine-3-carboxylic acid, it can be produced according to the methods described in J. Am. Chem. Soc., 77, 5932–5933 (1955) or analogous methods thereto. Compound (III) which is 7-methoxy-2-oxo-1,2,3,4-tetrahydroquinoline-3-carboxylic acid can be produced according to the methods described in JP-A-7-126267.

The "amidation" may be effected in any per se known methods, for example, (1) by reacting compound (III) with a compound of the formula:

$$HNR^1R^2$$

in the presence of a dehydrating condensing agent, or (2) by reacting a reactive derivative of compound (III) with a compound of the formula:

$$HNR^1R^2.$$

In the above reaction (1), compound (III) is reacted with 1 to 5 equivalents of a compound of the formula:

$$HNR^1R^2$$

in the presence of 1 to 2 equivalents of a dehydrating condensing agent, in an inert solvent, at room temperature, for 10 to 24 hours. If desired, 1 to 1.5 equivalents of 1-hydroxybenzotriazole (HOBT) and/or 1 to 5 equivalents of a base (e.g., triethylamine, etc.) may be added to the reaction system.

The "dehydrating condensing agent" includes, for example, dicyclohexylcarbodiimide (DCC), 1-ethyl-3-(3-dimethylaminopropyl)carbodiimide hydrochloride (WSC), etc. Of those, preferred is WSC.

The inert solvent includes, for example, nitriles (preferably, acetonitrile), amides (preferably, DMF), halogenated hydrocarbons (preferably, dichloromethane), ethers (preferably, THF), etc., which may be used either singly or as a suitable mixture of two or more species.

In the above reaction (2), a reactive derivative of compound (III) is reacted with 1 to 5 equivalents, preferably 1 to 3 equivalents of a compound of the formula:

$$HNR^1R^2,$$

in an inert solvent, at −20 to 50° C., preferably at room temperature, for 5 minutes to 40 hours, preferably 1 to 18 hours. If desired, 1 to 10 equivalents, preferably 1 to 3 equivalents of a base may be in the reaction system.

The "reactive derivative" of compound (III) includes, for example, its acid halides (e.g., acid chlorides, acid bromides, etc.), mixed acid anhydrides (e.g., acid anhydrides with $C_{1-6}$ alkyl-carboxylic acids, $C_{6-10}$ aryl-carboxylic acids or $C_{1-6}$ alkyl-carbonic acids, etc.), and active esters (e.g., esters with phenol which may be substituted, 1-hydroxybenzotriazole or N-hydroxysuccinimide, etc.). The "substituent" for the "phenol which may be substituted" includes, for example, 1 to 5 substituents selected from the group consisting of halogen atoms, nitro, optionally halogenated $C_{1-6}$ alkyl and optionally halogenated $C_{1-6}$ alkoxy. Specific examples of the "phenol which may be substituted" are phenol, pentachlorophenol, pentafluorophenol, p-nitrophenyl, etc. The reactive derivatives are preferably acid halides.

The "base" is the same as those mentioned in detail hereinabove for the step 1. Preferred are potassium carbonate, sodium carbonate, sodium hydroxide, potassium hydroxide, sodium hydrogencarbonate, potassium hydrogencarbonate, triethylamine, pyridine, etc. The inert solvent includes, for example, ethers, halogenated hydrocarbons, aromatic solvents, nitriles, amides, ketones, sulfoxides, water, etc., which may be used either singly or as a suitable mixture of two or more species. Of those, preferred are acetonitrile, dichloromethane, chloroform, etc.

Step 3

Compound (IV) is subjected to reduction to obtain compound (V).

The reduction may be effected in any per se known manner, for example, according to the methods described in Organic Functional Group Preparations, 2nd Ed., Academic Press Inc., 1989, etc. Concretely, for example, (1) compound (IV) is reacted with a metal hydride; (2) compound (IV) is reacted with a metal; or (3) compound (IV) is subjected to catalytic reduction.

In the reaction (1), compound (IV) is reacted with 1 to 20 equivalents, preferably 1 to 6 equivalents of a metal hydride in an inert solvent.

The "metal hydride" includes, for example, aluminum hydride, lithium aluminum hydride, sodium borohydride, lithium borohydride, sodium borohydride cyanide, lithium borohydride cyanide, borane complexes (e.g., borane-THF complex, catechol-borane, etc.), dibutyl aluminum hydride, as well as mixtures of those metal hydrides and Lewis acids (e.g., aluminum chloride, titanium tetrachloride, cobalt chloride, etc.) or phosphorus oxychloride, etc. Preferred metal hydrides are lithium aluminum hydride and aluminum hydride.

The inert solvent includes, for example, ethers.

The reaction temperature varies, depending on the metal hydride used, but generally falls between −70 and 100° C. Where lithium aluminum hydride is used, the reaction temperature may be between room temperature and 80° C. Where borane complex is used, the reaction temperature may be between room temperature and 100° C., preferably between room temperature and 60° C.

The reaction time falls between 1 and 48 hours.

In the reaction (2), compound (IV) is reacted with 1 to 20 equivalents, preferably 2 to 6 equivalents of a metal in an inert solvent.

The "metal" includes, for example, zinc, iron, sodium, potassium, etc.

The inert solvent includes, for example, organic acids (e.g., acetic acid, propionic acid, methanesulfonic acid, etc.), ethers, aromatic solvents, hydrocarbons, etc., which may be used either singly or as a suitable mixture of two or more species. Preferred are ethers.

The reaction temperature varies, depending on the metal used, but generally falls between −70 and 100° C. Where zinc is used, the reaction temperature may fall between room temperature and 80° C.

The reaction time falls between 1 and 10 hours.

In the reaction (3), compound (IV) is reacted with a catalytic amount to 10 equivalents of a metal catalyst (e.g., Raney nickel, etc.) and a phosphorus sulfide compound (e.g., phosphorus pentasulfide, phosphorus trisulfide, etc.), in an inert solvent (e.g., alcohols, etc.), at room temperature to 100° C. under a hydrogen pressure of 1 to 100 atmospheres, for 1 to 48 hours.

In the above step 3, by selecting the reaction condition for the reduction, a carbonyl group and a lactam which are functional groups in the molecule (IV), are reduced to give a hydroxy and a cyclic amino, respectively.

In the case that the fused ring formed by Ring A and Ring B is, for example, 2-oxo-1,2,3,4-tetrahydroquinoline or 2-oxo-2,3,4,5-tetrahydro-1H-1-benzazepine, 1,2,3,4-tetrahydroquinoline and 2,3,4,5-tetrahydro-1H-1-benzazepine are obtained, respectively by using the above borane complexes. Concretely, compound (IV) is reacted with one equivalent to an excessive amount, preferably 1 to 5 equivalents of borane complexes in an ethers, at room temperature to 100° C., preferably at room temperature to 60° C., for 0.1 to 48 hours, preferably 1 to 5 hours.

Step 4

Compound (V) is subjected to deprotection to obtain compound (IIa).

Briefly, compound (V) wherein W is a protective group is subjected to deprotection in per se known manner.

The deprotection may be effected, for example, according to the methods described in Organic Functional Group Preparations mentioned above, etc. Concretely, the deprotection includes, for example, deprotection by acid, catalytic reduction, hydrolysis, nucleophilic substitution, etc., which may be suitably selected in accordance with the protective group W.

In the case that W is $C_{1-6}$ alkyl, preferably methyl, for example, compound (V) is reacted with 1 to 100 equivalents of an acid in the absence or presence of an insert solvent, at −78 to 200° C., for 5 minutes to 24 hours.

The acid includes, for example, mineral acids (e.g., hydrochloric acid, hydrobromic acid, hydroiodic acid, etc.), Lewis acids (e.g., aluminum chloride, boron tribromide, etc.), and halogenated silane reagents (e.g., iodotrimethylsilane, bromotrimethylsilane, etc.).

The inert solvent includes, for example, water, halogenated hydrocarbons, acetic acid, etc., which may be used either singly or as a suitable mixture of two or more species.

Preferably, compound (V) is reacted with 5 to 100 equivalents of hydrobromic acid in water or acetic acid, at 100 to 130° C., for 1 to 5 hours.

In the case that W is a benzyl which may be substituted, for example, compound (V) is subjected to catalytic reduction in general.

Briefly, compound (V) is reacted with a catalytic amount of a metal catalyst (e.g., Raney nickel, platinum hydroxide, palladium metal, palladium-carbon, etc.), in an inert solvent (e.g., alcohols, etc.), at room temperature to 100° C., under a hydrogen pressure of 1 to 100 atmospheres, for 1 to 48 hours. Preferably, compound (V) is reacted with a catalytic amount of palladium-carbon, in alcohols (e.g., ethanol, etc.), under a hydrogen pressure of 1 to 10 atmospheres, at room temperature to 50° C., for 1 to 10 hours.

In the case that W is C16 alkyl-carbonyl, a benzoyl or a $C_{7-10}$ aralkyl-carbonyl, for example, compound (V) is subjected to hydrolysis.

Briefly, compound (V) is reacted with 2 to 100 equivalents, preferably 5 to 10 equivalents of an alkali in an inert solvent, at room temperature to 120° C., preferably at room temperature to 60° C., for 5 minutes to 100 hours, preferably for 1 to 20 hours.

The alkali includes, for example, hydroxides of inorganic bases such as lithium hydroxide, sodium hydroxide, potassium hydroxide, barium hydroxide, etc. Of those, preferred is sodium hydroxide.

The inert solvent includes, for example, water, alcohols, ethers, etc., which may be used either singly or as a suitable mixture of two or more species. Of those, preferred is a mixed solvent of water-methanol.

Preferably, the solvent is a mixed solvent of water-methanol, the reaction temperature falls between room temperature and 60° C., and the reaction time falls between 5 and 10 hours.

Scheme 3

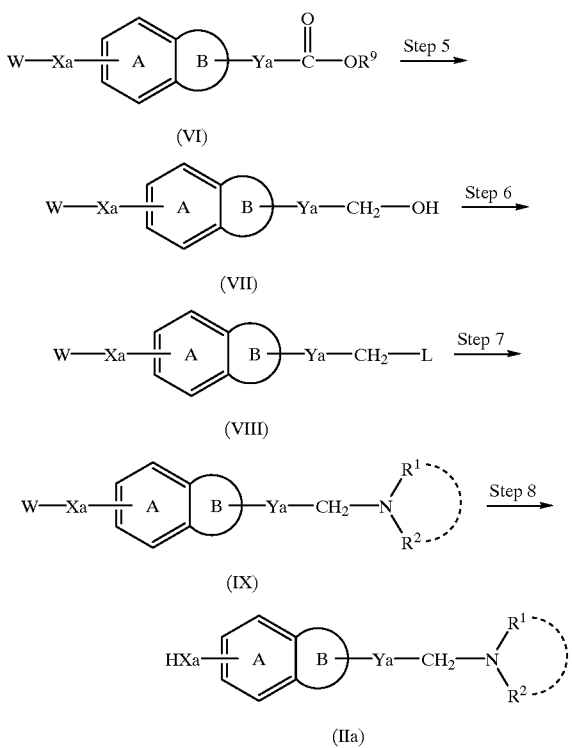

In those formulae, $R^9$ represents a protective group for carboxy; and L represents a leaving group.

The "protective group for carboxy" for $R^9$ are the same as those for the "protective group for carboxy" which will be mentioned hereinafter. $R^9$ is preferably a $C_{1-6}$ alkyl.

The "leaving group" for L are the same as those mentioned above for L.

Step 5

Compound (VI) is subjected to reduction to obtain compound (VII).

Compound (VI) is easily available, and can be obtained, for example, by subjecting compound (III) to esterification in per se known manner.

The reduction may be effected in any per se known manner, for example, according to the methods described in Organic Functional Group Preparations mentioned above, etc. For the reaction condition for the reduction, referred to is the same as that for the step 3. Preferably employed are metal hydrides.

Concretely, for example, compound (VI) is reacted with 1 to 20 equivalents, preferably 1 to 6 equivalents of a metal hydride (preferably, lithium aluminum hydride) in an inert solvent.

The inert solvent includes, for example, ethers, alcohols, aromatic solvents, etc., which may be used either singly or as a suitable mixture of two or more species.

The reaction temperature varies, depending on the metal hydride used, but, in general, falls between −70 and 100° C. Where lithium aluminum hydride is used, the reaction temperature is preferably between room temperature and 50° C.

Step 6

A leaving group is introduced into compound (VII) to obtain compound (VIII).

In the case that L is a halogen in compound (VIII), compound (VII) is reacted with a halogenating reagent.

For example, where a commercially-available halogenating reagent (e.g., hydrobromic acid, phosphorus tribromide, phosphorus pentabromide, thionyl chloride, etc.) is used as a halogenating reagent, the halogenation may be effected in any per se known manner. For example, where hydrobromic acid is used as a halogenating reagent, compound (VII) may be reacted with 1.5 to 5 equivalents of the hydrobromic acid at 80 to 130° C. for 1 to 18 hours.

Where the halogenating reagent is prepared, 1 to 1.5 equivalents of bromine or iodine is mixed with the same amount of triphenylphosphine in an inert solvent (e.g., nitrites, ethers, etc.) at room temperature to give a halogenating reagent. The thus-prepared halogenating reagent is reacted with compound (VII) in the same solvent at room temperature for 0.5 to 18 hours, preferably from 0.5 to 3 hours.

In the case that L is a sulfonyloxy (e.g., methanesulfonyloxy, p-toluenesulfonyloxy, benzenesulfonyloxy, etc.) in compound (VIII), compound (VII) is stirred with one equivalent or an excessive amount, preferably 1 to 1.5 equivalents of a sulfonating reagent (e.g., methanesulfonyl chloride, p-toluenesulfonyl chloride, benzenesulfonyl chloride, etc.) along with a base in an inert solvent at −50 to 50° C., preferably at room temperature, for 1 to 24 hours.

The "base" is the same as those mentioned in detail above for the step 1. Especially preferred are amines such as triethylamine, diisopropylethylamine, N-methylmorpholine, dimethylaminopyridine, etc.; and basic heterocyclic compounds such as pyridine, imidazole, 2,6-lutidine, etc. The amount of the base to be used is 1 to 8 equivalents relative to the sulfonating reagent used.

The inert solvent includes, for example, halogenated hydrocarbons, nitrites, esters, etc., which may be used either singly or as a suitable mixture of two or more species.

The sulfonyloxy group in the resultant compound (VIII) may be subjected to iodation. For this, for example, compound (VIII) is reacted with 1 to 10 equivalents, preferably 1 to 3 equivalents of sodium iodide or potassium iodide in an inert solvent (e.g., ketones, ethers, etc.) at room temperature to 100° C., preferably at 30 to 60° C., for 1 to 24 hours.

Step 7

Compound (VIII) is subjected to amination to obtain compound (IX).

The amination may be effected in any per se known method, for example, according to the methods described in Organic Functional Group Preparations mentioned above, etc. Concretely, for example, compound (VIII) is stirred with 1 to 5 equivalents, preferably 1 to 2 equivalents of a compound of the formula:

$HNR^1R^2$ in an inert solvent at room temperature to 100° C., preferably at room temperature to 50° C., for 0.5 hours to one day. In general, 1 to 5 equivalents, preferably 1 to 3 equivalents of a base is added to the reaction system.

The "base" is the same as those mentioned in detail hereinabove for the step 1. Especially preferred are tertiary amines such as triethylamine, etc.; and alkali metal or alkaline earth metal carbonates, etc.

The inert solvent includes, for example, water, alcohols, ethers, halogenated hydrocarbons, aromatic solvents, nitrites, amides, ketones, sulfoxides, etc., which may be used either singly or as a suitable mixture of two or more species. Of those, preferred are acetonitrile, N,N-dimethylformamide (DMF), acetone, ethanol, etc.

Preferably, compound (VIII) is stirred with 1 to 2 equivalents of a compound of the formula:

HNR$^1$R$^2$, along with 1 to 3 equivalents of a base (e.g., potassium carbonate, triethylamine, etc.) in an inert solvent (e.g., acetonitrile, DMF, etc.), at room temperature to 50° C., for 10 hours to one day.

Step 8

Compound (IX) is subjected to deprotection to obtain compound (IIa).

The deprotection may be effected under the same reaction condition as that for the step 4.

Compound (II) wherein Y is a methylene may be obtained according to the following scheme 4.

Scheme 4

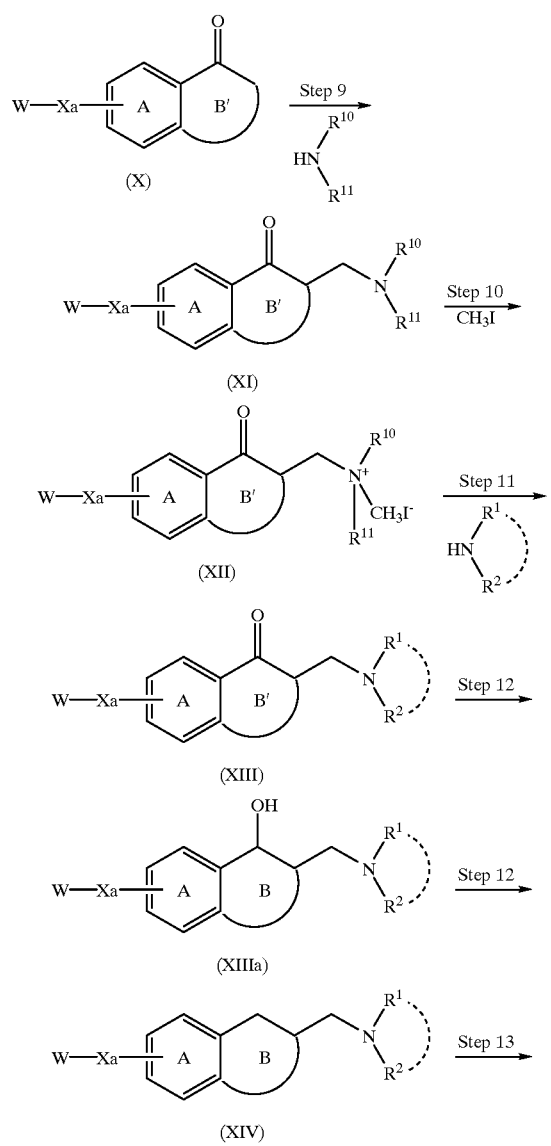

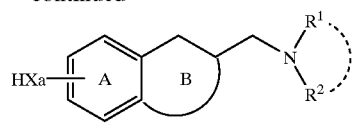

(IIb)

In those formulae, Ring B' corresponds to Ring B having an oxo; and R$^{10}$ and R$^{11}$ each represents a C$_{1-6}$ alkyl or a benzyl which may be substituted by 1 to 3 substituents selected from the group consisting of halogen and nitro.

Step 9

Compound (X) is subjected to Mannich reaction to obtain compound (XI).

Compound (X) is easily available, and can be produced by any per se known methods.

The Mannich reaction may be effected in any per se known manner, for example, according to the methods described in WO 92/05143, etc. Concretely, for example, compound (X) is reacted with an excessive amount of formaldehyde or paraformaldehyde and 1 to 5 equivalents, preferably 1 to 2 equivalents of a secondary amine (e.g., a compound of the formula:

HNR$^{10}$R$^{11}$, etc.) or 1 to 10 equivalents, preferably 1 to 5 equivalents of a dimethylmethylene-ammonium salt (e.g., chloride, iodide, etc.), in an inert solvent, at room temperature to 80° C., for 1 to 48 hours. If desired, an equivalent amount to an excessive amount of an acid (e.g., mineral acids such as hydrochloric acid, etc.) may be added to the reaction system.

The inert solvent includes, for example, ethers, alcohols, nitriles, water, etc., which may be used either singly or as a suitable mixture of two or more species.

In the case that R$^{10}$ and R$^{11}$ each is C$_{1-6}$ alkyl in the compound of the formula:

HNR$^{10}$R$^{11}$, thus obtained compound (XI) is directly subjected to the reaction of step 12 without being subjected to the reaction of the next step 10.

Step 10

Compound (XI) is converted into its quaternary amine salt, compound (XII).

After the previous step 9, the obtained compound (XI) is then reacted with 1 to 3 equivalents, preferably 1.1 to 1.5 equivalents of a C$_{1-6}$ alkyl halide (e.g., methyl iodide, etc.) in an inert solvent (e.g., ketones, alcohols, etc.), at room temperature to a temperature for reflux, for 0.1 to 24 hours, preferably for 0.5 to 2 hours.

Step 11

Compound (XII) is subjected to amination to obtain compound (XIII).

The amination may be effected under the same reaction condition as that for the step 7. Concretely, for example, compound (XII) is stirred with 1 to 5 equivalents, preferably 1 to 3 equivalents of a compound of the formula:

HNR$^1$R$^2$, in an inert solvent, at room temperature to 100° C., preferably at room temperature to 50° C., for 0.5 hours to one day. In general, 1 to 3 equivalents, preferably 1 to 2 equivalents of a base is added to the reaction system.

The "base" is the same as those mentioned in detail hereinabove for the step 1. Especially preferred are tertiary amines such as triethylamine, etc.; and alkali metal or alkaline earth metal carbonates, etc.

The inert solvent includes, for example, water, alcohols, ethers, halogenated hydrocarbons, aromatic solvents, nitriles, amides, ketones, sulfoxides, etc., which may be used either singly or as a suitable mixture of two or more species. Of those, preferred are acetonitrile, DMF, acetone, ethanol, etc.

Preferably, compound (XII) is stirred with 1 to 2 equivalents of a compound of the formula:

$HNR^1R^2$, and 1 to 3 equivalents of a base (e.g., potassium carbonate, triethylamine, etc.), in an inert solvent (e.g., acetonitrile, DMF, etc.), at room temperature to 50° C., for 10 hours to one day.

Step 12

Compound (XIII) is subjected to reduction to obtain compound (XIV) via compound (XIIIa).

The reduction may be effected in any per se known manner, for example, according to the methods described in Organic Functional Group Preparations mentioned above, etc. Concretely, for example, (1) compound (XIII) is reacted with a metal hydride, (2) compound (XIII) is reacted with a metal, or (3) compound (XIII) is subjected to catalytic reduction.

In the above reaction (1), compound (XIII) is reacted with 1 to 20 equivalents, preferably 2 to 6 equivalents of a metal hydride in an inert solvent.

The "metal hydride" includes, for example, lithium aluminum hydride, sodium borohydride, lithium borohydride, sodium borohydride cyanide, diborane, dibutyl aluminum hydride, etc.

The inert solvent is preferably ethers when lithium aluminum hydride is used, but is preferably alcohols when sodium borohydride is used.

The reaction temperature varies, depending on the metal hydride used, but, in general, may fall between −70 and 100° C., preferably between 0 and 80° C.

The reaction time falls between 0.1 and 24 hours, preferably between 0.5 and 12 hours.

In the above reaction (2), compound (XIII) is reacted with an excessive amount, preferably 1 to 100 equivalents of a metal (e.g., zinc powder) in an inert solvent at room temperature to 100° C. for 1 to 24 hours. In the reaction (2), as the case may be, the reduction may be further promoted to directly give compound (XIV).

The inert solvent includes, for example, organic acids (e.g., acetic acid, etc.), ethers, etc., which may be used either singly or as a suitable mixture of two or more species.

In the above reaction (3), compound (XIII) is reacted with a catalytic amount of a metal catalyst (e.g., Raney nickel, platinum oxide, palladium metal, palladium-carbon, etc.) in an inert solvent (e.g., alcohols, etc.), at room temperature to 100° C., under a hydrogen pressure of 1 to 100 atmospheres, for 1 to 48 hours. If desired, a catalytic amount to an excessive amount of an organic acid (e.g., acetic acid, etc.) or a mineral acid (e.g., perchloric acid, hydrochloric acid, etc.) may be added to the reaction system. In the reaction (3), as the case may be, the reduction may be further promoted to directly give compound (XIV).

The compound (XIIIa) obtained herein is subjected to reductive dehydration to give compound (XIV).

The reductive dehydration may be effected in any per se known manner, for example, through catalytic reduction or using an organic silyl reagent.

For the catalytic reduction, for example, it is preferred that compound (XIIIa) is reacted with a catalytic amount of a metal catalyst (e.g., Raney nickel, platinum oxide, palladium metal, palladium-carbon, etc.) in an inert solvent (e.g., alcohols, etc.) under a hydrogen pressure of 1 to 100 atmospheres, at room temperature to 100° C., for 1 to 48 hours. If desired, a catalytic amount to an excessive amount of an organic acid (e.g., acetic acid, etc.) or a mineral acid (e.g., perchloric acid, hydrochloric acid, etc.) may be added to the reaction system.

In the method of using an alkylsilane reagent, for example, compound (XIIIa) is reacted with an alkylsilane reagent (e.g., triethylsilane, phenyldimethylsilane, etc.) and an acid (e.g., organic acids such as trifluoroacetic acid, etc.), in the absence or presence of an inert solvent (e.g., halogenated hydrocarbons), at 0 to 100° C., preferably at 0 to 30° C., for 10 minutes to 24 hours.

The amount of the alkylsilane reagent to be used is 1 to 10 equivalents, preferably 1 to 5 equivalents, relative to the compound (XIIIa).

The amount of the acid to be used is a catalytic amount to an excessive amount, preferably 1 to 5 equivalents, relative to the compound (XIIIa).

Step 13

In the case that W is a protective group in compound (XIV), compound (XIV) is subjected to deprotection to obtain compound (IIb).

The deprotection may be effected under the same reaction condition as that for the step 4.

Process 2

Scheme 5

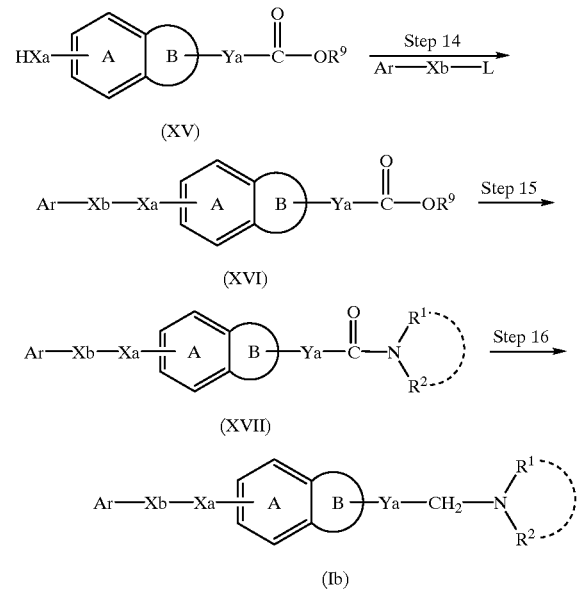

Step 14

Compound (XV) is subjected to alkylation or acylation to obtain compound (XVI).

Compound (XV) can be obtained by subjecting compound (III) wherein W is a hydrogen to esterification in any per se known manner.

The alkylation and the acylation may be effected in the same manner as in the step 1.

Step 15

Compound (XVI) is subjected to hydrolysis in any per se known manner, and then amidation to obtain compound (XVII).

The amidation may be effected in the same manner as in the step 2.

Step 16

Compound (XVII) is subjected to reduction to obtain compound (Ib).

The reduction may be effected in the same manner as in the step 3.

Process 3

Scheme 6

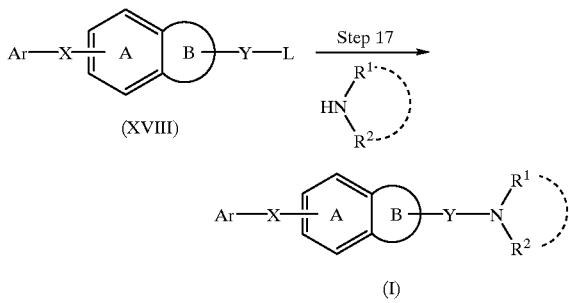

(I)

In the formula, L represents a leaving group.

The "leaving group" for L are the same as those mentioned hereinabove.

Step 17

Compound (XVIII) is subjected to amination to obtain compound (I).

Compound (XVIII) can be produced with ease according to any known methods, for example, a method of scheme 7 mentioned below.

The amination may be effected in the same manner as in the step 7.

Scheme 7

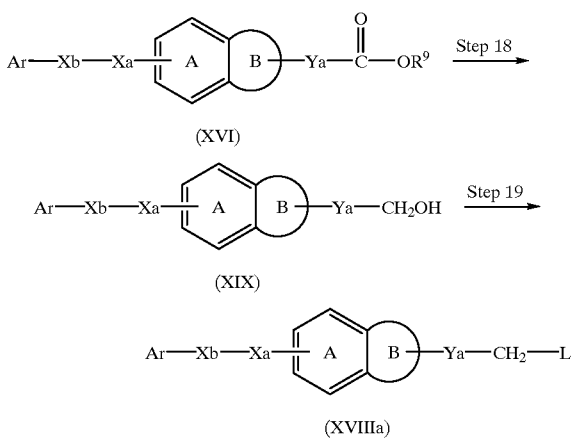

Step 18

Compound (XVI) is subjected to reduction to obtain compound (XIX).

The reduction may be effected in the same manner as in the step 5.

Step 19

A leaving group is introduced into compound (XIX) to obtain compound (XVIIIa).

The introduction of the leaving group may be effected in the same manner as in the step 6.

Process 4

Scheme 8

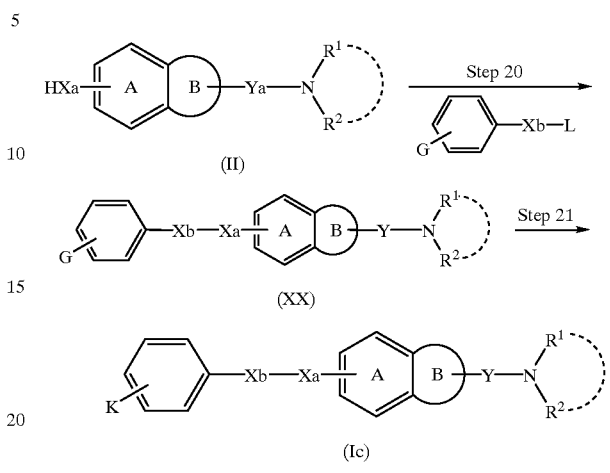

In the formula, K represents an aromatic group which may be substituted; and G represents a halogen atom (e.g., bromo, iodo), or a trifluoromethanesulfonyloxy.

For the "aromatic group which may be substituted" for K, referred to is the same as those mentioned hereinabove for the "aromatic group which may be substituted" for Ar'.

Step 20

Compound (II) is subjected to the same reaction as in the step 1 to obtain compound (XX).

Step 21

Compound (XX) is subjected to aryl-coupling reaction to obtain compound (Ic).

The aryl-coupling reaction may be effected in any per se known manner, for example, according to the methods described in Acta. Chemica Scandinavia, 221–230 (1993), etc. Concretely, for example, compound (XX) is reacted with 1 to 2 equivalents of an aryl metal compound and 1 to 10 equivalents of a base, in the presence of 0.01 to 1 equivalent, preferably 0.01 to 0.5 equivalents of a transition metal catalyst, in an inert solvent, at room temperature to 150° C., preferably at 80 to 150° C., for 1 to 48 hours.

The "aryl metal compound" includes, for example, arylboric acid derivatives, aryl-zinc derivatives, etc.

The "base" includes, for example, an aqueous solution of sodium carbonate, sodium hydrogencarbonate or the like.

The "transition metal catalyst" includes, for example, palladium catalysts, nickel catalysts, etc. The "palladium catalysts" include, for example, tetrakis(triphenylphosphine)palladium(0), palladium acetate, bis(triphenylphosphine)palladium(II) chloride, palladium-carbon, etc. The "nickel catalysts" include, for example, tetrakis(triphenylphosphine)nickel(0), etc.

The inert solvent includes, for example, water, alcohols, aromatic solvents, etc., which may be used either singly or as a suitable mixture of two or more species. Preferred are water, ethanol, toluene, etc., which are used either singly or as a suitable mixture of two or more species.

Where the intermediates produced in those Processes 1 to 4 include optical isomers, any known methods of obtaining such "optical isomers of those intermediates" are employable herein. For example, the optical isomers may be derived from optically-active compounds, or racemates may be subjected to optical resolution or asymmetric synthesis.

For the "optical resolution", referred to is the same as the optical resolution to be mentioned hereinafter.

The "asymmetric synthesis" may be effected in any per se known manner, including, for example, asymmetric reduction, asymmetric oxidation, asymmetric alkylation, etc. These reactions may be attained, for example, according to the methods described in Shin-Jikken Kagaku Koza, 26 (1992), edited by the Chemical Society of Japan and published by Maruzen Co., etc. Of those, preferred is asymmetric reduction.

The "asymmetric reduction" includes, for example, reduction using asymmetric metal hydrides, asymmetric hydrogenation, etc. Preferred is asymmetric hydrogenation. The "asymmetric hydrogenation" includes, for example, a reaction using asymmetric metal catalysts. One embodiment of the asymmetric hydrogenation is effected in the presence of transition metal/optically-active phosphine complexes.

For example, compounds (III), (IV), (V), (VI), (VII), (XVI) and (XVII) produced in any of Processes 1 to 4, wherein each Ring B is a ring of the formula:

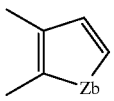

wherein Zb has the same meaning as Z, are subjected to asymmetric hydrogenation to obtain the corresponding optical isomers, respectively.

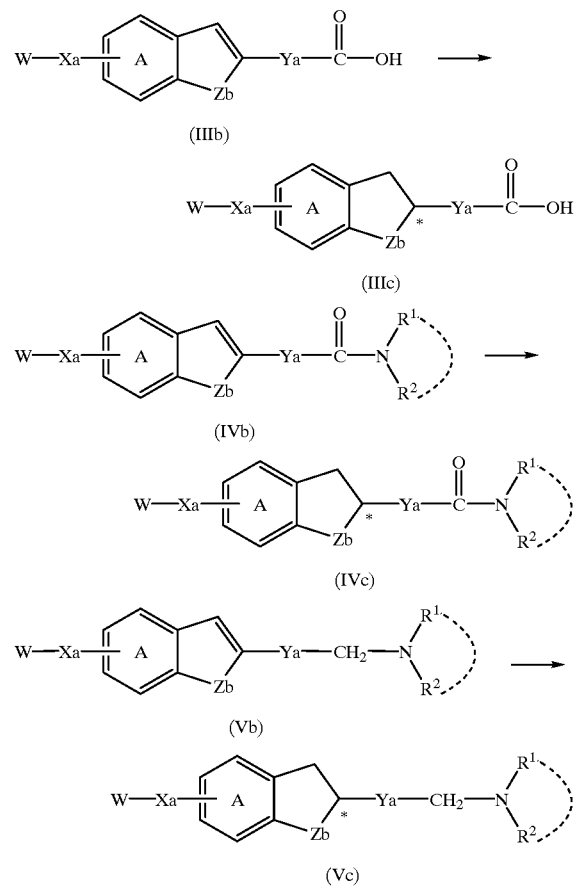

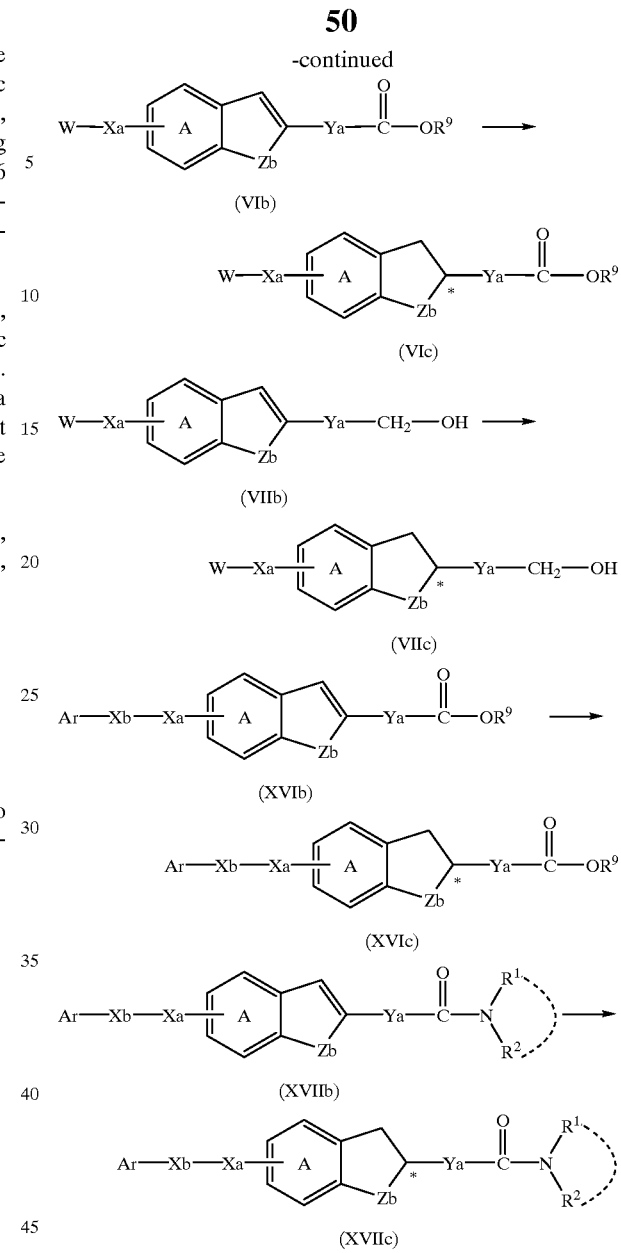

In those formulae, * indicates the position of the asymmetric carbon, and the other symbols have the same meanings as above.

As one example of the "asymmetric hydrogenation", mentioned is a method of reacting compound (IIIb), (IVb), (Vb), (VIb), (VIIb), (XVIb) or (XVIIb) with approximately 0.00001 to 1 equivalent, preferably approximately 0.001 to 0.1 equivalents of a transition metal/optically-active phosphine complex, in an inert solvent, at room temperature to 100° C., preferably at about 50 to 80° C., under a hydrogen pressure of 5 to 100 kg/cm$^2$, preferably from 50 to 100 kg/cm$^2$, for 1 to 48 hours, preferably for 1 to 6 hours, to obtain compound (IIIc), (IVc), (Vc), (VIc), (VIIc), (XVIc) or (XVIIc), respectively.

The concentration of the compound (IIIb), (IVb), (Vb), (VIb), (VIIb), (XVIb) or (XVIIb) in the reaction system is 1 to 1000 mg/ml, preferably 50 to 300 mg/ml.

If desired, a suitable amount of a Lewis acid (e.g., boron trifluoride-ether complex, aluminum chloride, titanium tetrachloride, cobalt chloride, etc.) or a mineral acid (e.g., hydrochloric acid, hydrobromic acid, hydroiodic acid, etc.) may be added to the reaction system.

The "transition metal" of the "transition metal/optically-active phosphine complex" includes, for example, ruthenium, rhodium, iridium, palladium, nickel, etc. Of those, preferred is ruthenium.

The optically-active phosphine of the "transition metal/optically-active phosphine complex" includes two optical isomers of (R) configuration and (S) configuration. Either one of the two optical isomers of (R) configuration and (S) configuration is used for the asymmetric reduction to selectively obtain the intended optical isomer product.

Examples of the "optically-active phosphine" are (R)-2,2'-bis(diphenylphosphino)-1,1'-binaphthyl [(R)-(BINAP)], (S)-2,2'-bis(diphenylphosphino)-1,1'-binaphthyl [(S)-(BINAP)], (R)-2,2'-bis(di-p-tolylphosphino)-1,1'-binaphthyl [(R)-(p-tolyl-BINAP)], (S)-2,2'-bis(di-p-tolylphosphino)-1,1'-binaphthyl [(S)-(p-tolyl-BINAP)] (see JP-A-61-63690); (R)-2,2'-bis[di-(3,5-dimethylphenyl)phosphino]-1,1'-binaphthyl [(R)-(3,5-xylyl-BINAP)], (S)-2,2'-bis[di-(3,5-dimethylphenyl) phosphino]-1,1'-binaphthyl [(S)-(3,5-xylyl-BINAP)] (see JP-A-3-255090); (R)-2,2'-bis(diphenylphosphino)-5,5',6,6',7,7',8,8'-octahydro-1,1'-binaphthyl [(R)-(H$_8$-BINAP)], (S)-2,2'-bis(diphenylphosphino)-5,5',6,6',7,7',8,8'-octahydro-1,1'-binaphthyl [(S)-(H$_8$-BINAP)] (see JP-A-4-139140), etc.

The above "(R)" and "(S)" each indicates the absolute configuration in that optically-active phosphine.

The "transition metal/optically-active phosphine complex" may additionally have, as ligands, a halogen (e.g., chloro, etc.), an amine (e.g., triethylamine, etc.), an organic acid (e.g., acetic acid, etc.), a $C_{6-10}$ aryl (e.g., benzene, etc.), etc.

After having been prepared, the "transition metal/optically-active phosphine complex" may be directly used in the reaction without being isolated or purified.

"Ruthenium/optically-active phosphine complexes" which are preferred examples of the "transition metal/optically-active phosphine complex" each are composed of ruthenium and either one, optically-active (R)— or (S)— phosphine compound, and include, for example, the following:

Bis[[(R)— or (S)-[2,2'-bis(diphenylphosphino)-1,1'-binaphthyl]]dichlororuthenium]triethylamine (referred to as [RuCl$_2$[(R)— or (S)-(BINAP)]]$_2$NEt$_3$);

Bis[[(R)— or (S)-[2,2'-bis(di-p-tolylphosphino)-1,1'-binaphthyl]]dichlororuthenium]triethylamine (referred to as [RuCl$_2$[(R)— or (S)-(p-tolyl-BINAP)]]$_2$NEt$_3$);

Bis[[(R)— or (S)-[2,2'-bis(di-(3,5-dimethylphenyl)phosphino)-1,1'-binaphthyl]]dichlororuthenium]triethylamine (referred to as [RuCl$_2$[(R)— or (S)-(3,5-xylyl-BINAP)]]$_2$NEt$_3$);

Bis[[(R)— or (S)-[2,2'-bis(diphenylphosphino)-5,5',6,6',7,7',8,8'-octahydro-1,1'-binaphthyl]]dichlororuthenium]triethylamine (referred to as [RuCl$_2$[(R)— or (S)—(H$_8$-BINAP)]]$_2$NEt$_3$);

[(R)— or (S)-[2,2'-bis(diphenylphosphino)-1,1'-binaphthyl]]ruthenium diacetate (referred to as Ru(CH$_3$CO$_2$)$_2$[(R)— or (S)—(BINAP)]);

[(R)— or (S)-[2,2'-bis(di-p-tolylphosphino)-1,1'-binaphthyl]]ruthenium diacetate (referred to as Ru(CH$_3$CO$_2$)$_2$[(R)— or (S)-(p-tolyl-BINAP)]);

[(R)— or (S)-[2,2'-bis(di-(3,5-dimethylphenyl)phosphino)-1,1'-binaphthyl]]ruthenium diacetate (referred to as Ru(CH$_3$CO$_2$)$_2$[(R)— or (S)-(3,5-xylyl-BINAP)]);

[(R)— or (S)-[2,2'-bis(diphenylphosphino)-5,5', 6,6',7,7',8,8'-octahydro-1,1'-binaphthyl]]ruthenium diacetate (referred to as Ru(CH$_3$CO$_2$)$_2$[(R)— or (S)—(H$_8$-BINAP)]).

The inert solvent includes, for example, hydrocarbons, amides, aromatic solvents, ethers, halogenated hydrocarbons, alcohols, ketones, sulfoxides, nitrites, etc., which may be used either singly or as a suitable mixture of two or more species. Preferred are alcohols, and more preferred is ethanol.

The above "alcohols" includes, for example, methanol, ethanol, isopropanol, tert-butanol, etc.

The above "ethers" includes, for example, ethyl ether, tetrahydrofuran (THF), dioxane, 1,2-dimethoxyethane, etc.

The above "halogenated hydrocarbons" includes, for example, dichloromethane, chloroform, 1,2-dichloroethane, carbon tetrachloride, etc.

The above "aromatic solvents" includes, for example, benzene, toluene, xylene, pyridine, etc.

The above "hydrocarbons" includes, for example, hexane, pentane, cyclohexane, etc.

The above "amides" includes, for example, N,N'-dimethylformamide (DMF), N,N'-dimethylacetamide, N-methylpyrrolidone, etc.

The above "ketones" includes, for example, acetone, methyl ethyl ketone, etc.

The above "sulfoxides" includes, for example, dimethylsulfoxide (DMSO), etc.

The above "nitriles" includes, for example, acetonitrile, propionitrile, etc.

The above "esters" includes, for example, ethyl acetate, etc.

In the above-mentioned reactions where the starting compounds are substituted by any of amino, carboxy, hydroxy or carbonyl, those groups may be protected by ordinary protective groups which are generally used in peptide chemistry. The protective groups may be removed after the reaction to give the intended products.

The amino-protecting group includes, for example, formyl, $C_{1-6}$ alkyl-carbonyl (e.g., acetyl, propionyl, etc.), $C_{1-6}$ alkyloxy-carbonyl (e.g., methoxycarbonyl, ethoxycarbonyl, t-butoxycarbonyl, etc.), benzoyl, $C_{7-10}$ aralkyl-carbonyl (e.g., benzylcarbonyl, etc.), $C_{7-14}$ aralkyloxy-carbonyl (e.g., benzyloxycarbonyl, 9-fluorenylmethoxycarbonyl, etc.), trityl, phthaloyl, N,N-dimethylaminomethylene, silyl (e.g., trimethylsilyl, triethylsilyl, dimethylphenylsilyl, dimethyl-t-butylsilyl, diethyl-t-butylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkoxy (e.g., methoxy, ethoxy, propoxy, etc.) or nitro, etc.

The carboxy-protecting group includes, for example, $C_{1-6}$ alkyl (e.g., methyl, ethyl, propyl, isopropyl, butyl, tert-butyl, etc.), $C_{7-11}$ aralkyl (e.g., benzyl, etc.), phenyl, trityl, silyl (e.g., trimethylsilyl, triethylsilyl, dimethylphenylsilyl, dimethyl-t-butylsilyl, diethyl-t-butylsilyl, etc.), a $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkoxy (e.g., methoxy, ethoxy, propoxy, etc.) or nitro, etc.

The hydroxy-protecting group includes, for example, $C_{1-6}$ alkyl (e.g., methyl, ethyl, propyl, isopropyl, butyl, tert-butyl, etc.), phenyl, trityl, $C_{7-10}$ aralkyl (e.g., benzyl, etc.), formyl, $C_{1-6}$ alkyl-carbonyl (e.g., acetyl, propionyl, etc.), benzoyl, $C_{7-10}$ aralkyl-carbonyl (e.g., benzylcarbonyl, etc.), 2-tetrahydropyranyl, 2-tetrahydrofuranyl, silyl (e.g., trimethylsilyl, triethylsilyl, dimethylphenylsilyl, dimethyl-t-butylsilyl, diethyl-t-butylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkyl (e.g., methyl, ethyl, propyl, etc.), $C_{1-6}$ alkoxy (e.g., methoxy, ethoxy, propoxy, etc.) or nitro, etc.

The carbonyl-protecting group includes, for example, cyclic acetals (e.g., 1,3-dioxorane, etc.), acyclic acetals (e.g., di-$C_{1-6}$ alkylacetals, etc.), etc.

Those protective groups may be removed by any per se known methods, for example, the methods described in Protective Groups in Organic Synthesis, published by John Wiley and Sons, 1980, etc. For example, the method of removing these protective groups, includes the methods using acids, bases, ultraviolet ray, hydrazine, phenylhydrazine, sodium N-methyldithiocarbamate, tetrabutylammonium fluoride, palladium acetate, etc.; and reduction, etc.

Compound (I) can be isolated and purified by any known procedures, for example, through solvent extraction, ph adjustment, redistribution, crystallization, recrystallization, chromatography, etc. The starting compounds and intermediates and their salts for compound (I) can also be isolated and purified according to the same known procedures as above, but without any isolation procedure, they may be used in the next step while they are in reaction mixtures.

Compound (I) may also be in the form of hydrates or non-hydrates thereof.

Where compound (I) includes optical isomers, stereoisomers, regio isomers and rotational isomers, those are within the scope of compound (I), and can be isolated as their single compound through per se known synthesis or separation. For example, where optical isomers of compound (I) exist, those resolved from their mixtures through optical resolution are within the scope of compound (I).

The optical isomers can be produced in any per se known manner. Concretely, optically active synthetic intermediates or mixtures of racemate of the final product are subjected to ordinary optical resolution to give the corresponding optical isomers.

For the optical resolution, employable are any per se known methods, such as a fractional recrystallization method, a chiral column method, a diastereomer method, etc.

1) Fractional Recrystallization

The method which comprises allowing a racemate to react with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) to give a salt, which is then isolated through fractional recrystallization, followed by, when desired, subjecting the isolated compound to neutralization to obtain free optical isomers.

2) Chiral Column Method

The method of separating a racemate or a salt thereof, which comprises utilizing a column for fractionating optical isomers (chiral column). In the case of liquid column chromatography, for example, a mixture of optical isomers is applied to a chiral column, such as ENANTIO-OVM (manufactured by Tosoh Corp.), CHIRAL SERIES (manufactured by Daicel Co.), etc., which is then eluted with water, various buffers (e.g., phosphate buffer) and organic solvents (e.g., ethanol, methanol, isopropanol, acetonitrile, trifluoroacetic acid, diethylamine, etc.), singly or a suitable mixture of them, to isolate the individual optical isomers. In case of gas chromatography, for example, a chiral column such as CP-Chirasil-DeX CB (manufactured by GL Science Co.), etc. is used for the fractionation.

3) Diastereomer Method

A racemic mixture is chemically reacted with an optically-active reagent to give a mixture of diastereomer, which is subjected to ordinary separation (e.g., fractional recrystallization, chromatography, etc.) to give single compounds. The thus-isolated single compounds are then chemically processed, for example, through hydrolysis to thereby remove the optically-active reagent site from the compounds to obtain optical isomers. For example, where compound (I) has a hydroxy group or a primary or secondary amino group in the molecule, it is condensed with an optically-active organic acid (e.g., MPTA [α-methoxy-α-(trifluoromethyl)phenyl-acetic acid], (−)-menthoxyacetic acid, etc.) or the like to give the corresponding ester-type or amide-type diastereomer. On the other hand, where compound (I) has a carboxylic acid group, it is condensed with an optically-active amine or alcohol reagent to give the corresponding amide-type or ester-type diastereomer. The thus-isolated diastereomer is then subjected to acidic or basic hydrolysis, through which it is converted into the optical isomer of the original compound.

In the above-mentioned reactions, an optical isomer of the compound of the formula:

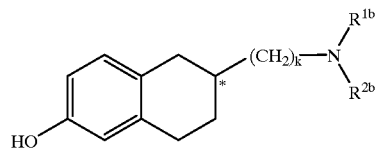

wherein $R^{1b}$ and $R^{2b}$ each represents methyl or ethyl, k represents 1 or 2, and * indicates the position of the asymmetric carbon, or a salt thereof is a novel compound.

Compound (I) of the present invention has both an excellent inhibitory effect on amyloid-β protein production and/or secretion and an excellent stimulating effect on secreted form of amyloid precursor protein (sAPP) secretion, and thus is effective in preventing and/or treating neurodegenerative disorders, amyloid angiopathy, neurological disorders caused by cerebrovascular disorders (e.g., cerebral infarction, encephalorrhagia, etc.), a head injury or an injury of spinal cord, etc. Compound (I') also has the inhibitory effect on amyloid-β protein production and/or secretion and stimulating effect on sAPP secretion.

In addition, compounds (I) and (I') have low toxicity. For example, in the experiment of acute toxicity, no mouse was dead by the oral administration of the compound obtained in Example 12 mentioned below a dose of more than 1000 mg/kg. Moreover, compounds (I) and (I') easily penetrate into the brain following the oral administration.

Therefor, compounds (I) and (I') are useful as safe medicines for preventing and/or treating neurodegenerative disorders, amyloid angiopathy, neurological disorders caused by cerebrovascular disorders (e.g., cerebral infarction, encephalorrhagia, etc.), a head injury or an injury of spinal cord, in mammals including human beings. They are also useful in ameliorating derangements (for example, depression, anxiety, compulsive neurosis, sleep disorders, etc.) caused by neurodegenerative disorders or neurological disorders. Of those, compounds (I) and (I') are preferably effective for neurodegenerative disorders such as Alzheimer's disease, Down's syndrome, senile dementia, Parkinson's disease, Creutzfeldt-Jacob disease, amyotrophic sclerosis on lateral fasciculus of spinal, diabetic neuropathy, Huntington's disease, multiple sclerosis, etc. Among others, preferred is neurodegenerative disorders to be coursed by amyloid-β protein (e.g., Alzheimer's disease, Down's syndrome, etc.), more preferred is Alzheimer's disease.

Compounds (I) and (I') may be used in combination with anti-dementia drugs (e.g., acetylcholinesterase inhibitor, etc.), and so forth.

Compounds (I) and (I') can be formulated into pharmaceutical compositions by any per se known means. Directly or after having been formulated into pharmaceutical compositions along with suitable amounts of any pharmaceutically acceptable carriers, compounds (I) and (I') can be safely administered to mammals including human beings. For example, compound (I) or (I') can be mixed with suitable amounts of any desired, pharmaceutically-acceptable carriers in any per se known formulation processes to give tablets (including sugar-coated tablets, film-coated tablets), powders, granules, capsules (including soft capsules), liquids, injections, suppositories, sustained release preparations, etc., which may be safely administered to mammals including human beings, either orally or non-orally (for example, topically, rectally, intravenously, etc.).

In the pharmaceutical composition of the present invention, the amount of compound (I) or (I') is 0.1 to 100% by weight of the total weight of the composition. The dose of the composition varies depending on the subject to which the composition is administered, the administration route employed, the disorder of the subject, etc. For example, for the peroral composition for treating Alzheimer's disease, its dose may be about 0.1 to 500 mg/adult (weighing about 60 kg) or so, preferably about 1 to 100 mg/adult or so, more preferably 5 to 100 mg/adult or so, in terms of the active ingredient [compound (I) or (I')], and this may be administered once or several times a day.

Any ordinary organic and inorganic carrier substances that are generally used in formulating medicines are usable as the carriers for formulating the pharmaceutical compositions of the present invention. For example, employable are ordinary excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, etc.

BEST MODE FOR CARRYING OUT THE INVENTION

The invention will be described in more detail hereinunder, with reference to Reference Examples, Examples, and Test Examples, which, however, are to concretely demonstrate the invention but not to restrict the scope of the invention. Various changes and modifications can be made within the range that does not deviate the scope of the invention.

"Room temperature" as referred to in the following Reference Examples and Examples is meant to indicate a temperature falling between 0° C. and 30° C. For removing water from the organic solution used therein, employed were anhydrous magnesium sulfate or anhydrous sodium sulfate. Unless otherwise specifically indicated, "%" is by weight.

The IR absorption spectra mentioned below were measured in a diffused reflection method using a Fourier transform infrared spectrophotometer.

The meanings of the abbreviations used hereinunder are as follows:

s: singlet d: doublet t: triplet q: quartet m: multiplet br: broad

J: coupling constant

Hz: Hertz $CDCl_3$: deuterated chloroform

THF: tetrahydrofuran

DMF: N,N-dimethylformamide

DMSO: dimethylsulfoxide

WSC: 1-ethyl-3-(3-dimethylaminopropyl)carbodiimide hydrochloride $^1$H NMR: proton nuclear magnetic resonance spectrum (generally measured as the free form of each sample in $CDCl_3$)

IR: infrared absorption spectrum

Reference Example 1

6-Methoxy-2-piperidinomethyl-1-tetralone hydrochloride

N-(6-Methoxy-1-oxo-2-tetralinyl)methyl-N,N,N-trimethylammonium iodide (1.137 g), piperidine (0.36 ml) and triethylamine (0.55 ml) were added to acetonitrile (300 ml). The reaction mixture was stirred at room temperature for 2 hours, and then concentrated. Water was added to this, which was then extracted with ethyl acetate. The organic layer was washed with a saturated aqueous sodium chloride solution, then dried, and concentrated. The residue was purified by alumina column chromatography (eluent:ethyl acetate/hexane=1/2), and then processed with a solution of 4 N hydrochloric acid-ethyl acetate. The resulting hydrochloride was recrystallized from methanol-ethyl acetate to obtain the entitled compound (0.586 g).

m.p.: 182–183° C.

Compounds of the following Reference Examples 2 and 3 were obtained in the same manner as in Reference Example 1

Reference Example 2

2-(N-Benzylamino)methyl-6-methoxy-1-tetralone hydrochloride m.p.: 166–169° C.

Solvent for recrystallization: methanol-ethyl acetate

Reference Example 3

2-(N,N-Dibenzylamino)methyl-6-methoxy-1-tetralone m.p.: 91–92° C.

Solvent for recrystallization: ethyl acetate-diisopropyl ether

Reference Example 4

2-(N,N-Dimethylamino)methyl-7-methoxytetralin hydrochloride

1 N Sodium hydroxide was added to 2-(N,N-dimethylamino) methyl-7-methoxy-1-tetralone hydrochloride (8.46 g) to convert it into a free compound, which was extracted with ethyl acetate. The extract was dried, and then concentrated. Sodium borohydride (2.32 g) was added to a methanol solution (150 ml) of the resulting residue, with cooling with ice, which was then stirred at room temperature for 12 hours. Water was added to the reaction mixture, which was concentrated under reduced pressure, and then extracted with ethyl acetate. The organic layer was washed with a saturated aqueous sodium chloride solution, then dried, and concentrated. Concentrated hydrochloric acid (6.4 g) and 10% palladium-carbon (0.7 g) were added to an ethanol solution (100 ml) of the resulting residue, which was thus catalytically reduced under a hydrogen pressure of 5 atmospheres at 60° C. for 8 hours. The catalyst was removed from the reaction mixture through filtration, and the filtrate was concentrated. The residue was recrystallized from methanol-ethyl acetate to obtain the entitled compound (6.53 g).

m.p.: 212–213° C.

Compounds of the following Reference Examples 5 to 7 were obtained in the same manner as in Reference Example 4.

Reference Example 5

2-(N,N-Dimethylamino)methyl-6-methoxytetralin hydrochloride m.p.: 197–199° C.

Solvent for recrystallization: methanol-ethyl acetate

Reference Example 6

2-(N-Benzylamino)methyl-6-methoxytetralin hydrochloride m.p.: 174–177° C.

Solvent for recrystallization: methanol-diethyl ether

Reference Example 7

6-Methoxy-2-piperidinomethyltetralin hydrochloride m.p.: 215–216° C.

Solvent for recrystallization: methanol-diethyl ether

Reference Example 8

2-Iodomethyl-6-methoxytetralin p-Toluenesulfonyl chloride (2.06 g) was added to an acetonitrile solution (20 ml) of 2-hydroxymethyl-6-methoxytetralin (1.888 g; described in J. Med. Chem., Vol. 37, p. 526, 1994) and pyridine (4.0 ml), with cooling with ice. The reaction mixture was stirred at room temperature for 24 hours, and 1 N hydrochloric acid was added thereto, which was then extracted with ethyl acetate. The organic layer was washed with water and a saturated aqueous sodium chloride solution, then dried, and concentrated. Sodium iodide (2.20 g) was added to an acetone solution (30 ml) of the resulting residue. The reaction mixture was heated under reflux for 16 hours, and then concentrated. Water was added to the residue, which was then extracted with ethyl acetate. The organic layer was washed with an aqueous solution of sodium thiosulfate and a saturated aqueous sodium chloride solution, then dried, and concentrated. The residue was purified by silica gel column chromatography (eluent: ethyl acetate/hexane=1/2) to obtain the entitled compound (2.506 g).

$^1$H NMR δ: 1.38–1.60(1H,m), 1.80–2.11(2H,m), 2.45 (1H,dd,J=16 Hz,8 Hz), 2.76–3.00(3H,m), 3,26(2H,d,J=6 Hz), 3.77(3H,s), 6.60–6.74(2H,m), 7.00(1H,d,J=8 Hz).

Reference Example 9

2-(N,N-dipropylamino)methyl-6-methoxytetralin hydrochloride

2-Iodomethyl-6-methoxytetralin (0.918 g; obtained in Reference Example 8), dipropylamine (0.83 ml) and potassium carbonate (0.90 g) were added to DMF (15 ml). The reaction mixture was stirred at room temperature for 20 hours. Water was added to this, which was then extracted with ethyl acetate. The organic layer was washed with water and a saturated aqueous sodium chloride solution, then dried, and concentrated. The residue was purified by silica gel column chromatography (eluent: ethyl acetate/hexane= 1/1), and then processed with a solution of 4 N hydrochloric acid-ethyl acetate to obtain its hydrochloride. This was recrystallized from ethyl acetate-diisopropyl ether to obtain the entitled compound (0.409 g).

m.p.: 135–137° C.

Reference Example 10

6-Methoxy-2-(N-methylamino)methyltetralin hydrochloride

An acetonitrile (400 ml) solution of N-(6-methoxy-1-oxo-2-tetralinyl) methyl-N,N,N-trimethylammonium iodide (44.5 g), N-benzyl-N-methylamine (14.4 g) and triethylamine (18 ml) was heated under reflux for 16 hours. The reaction mixture was concentrated, then water (200 ml) was added to the resulting residue, and an aqueous solution of 1 N sodium hydroxide was added to this to make it have pH of 9, which was then extracted with ethyl acetate (200 ml). The organic layer was washed with water, dried, and then concentrated. The residue was dissolved in methanol, and sodium borohydride (7.1 g) was added thereto, with cooling with ice, and then stirred at room temperature for 16 hours. The reaction mixture was concentrated, then water (200 ml) was added to the resulting residue, and an aqueous solution of 1 N sodium hydroxide was added to this to make it have pH of 9, which was then extracted with ethyl acetate (200 ml). The organic layer was washed with water, dried and then concentrated. The residue was purified by alumina column chromatography (eluent: ethyl acetate/hexane=1/1). Concentrated hydrochloric acid (26 ml) and 10% palladium-carbon (3 g) were added to an ethanol solution (200 ml) of the effective fraction obtained through the chromatography. The reaction mixture was catalytically reduced under atmospheric hydrogen pressure for 48 hours. The catalyst was removed from the mixture through filtration, and the resulting filtrate was concentrated. The crystals formed were washed with acetone to obtain the entitled compound (8.17 g).

m.p.: 192–193° C.

Reference Example 11

2-Aminomethyl-6-methoxytetralin hydrochloride

The entitled compound was obtained in the same manner as in Reference Example 10.

m.p. 217–218° C.

Solvent for recrystallization: ethanol-diisopropyl ether

Reference Example 12

N-(6-Methoxy-2-tetralinyl)methylacetamide

Acetyl chloride (0.67 g) was added to a pyridine solution (15 ml) of 2-aminomethyl-6-methoxytetralin hydrochloride (1.5 g; obtained in Reference Example 11), and the reaction mixture was stirred at room temperature for 16 hours, to which was added ethyl acetate. The organic layer was washed with 1 N hydrochloric acid and a saturated aqueous sodium bicarbonate solution, then dried, and concentrated. The resulting crude crystals were recrystallized from ethyl acetate-diisopropyl ether to obtain the entitled compound (960 mg).

m.p.: 96–97° C.

Reference Example 13

N,N-Dimethyl-(6-methoxy-2-tetralin)acetamide (6-Methoxy-2-tetralin)acetic acid (1.491 g), dimethylamine hydrochloride (0.846 g), WSC (1.726 g), 1-hydroxybenzotriazole (1.069 g) and triethylamine (2.8 ml) were added to acetonitrile (30 ml). The reaction mixture was stirred at room temperature for 20 hours, and 1 N hydrochloric acid was added thereto, which was then extracted with ethyl acetate. The organic layer was separated, washed with water, a saturated aqueous sodium bicarbonate solution and a saturated aqueous sodium chloride solution, then dried, and concentrated. The residue was purified by silica gel column chromatography (eluent: ethyl acetate/hexane=1/1) to obtain the entitled compound (1.667 g).

$^1$H NMR δ: 1.34–1.57(1H,m), 1.91–2.08(1H,m), 2.22–2.51(2H,m), 2.36(2H,s), 2.77–2.94(3H,m),2.98(3H,s), 3.02(3H,s), 3.77(3H,s), 6.59–6.72(2H,m), 6.96(1H,d,J=8 Hz).

Reference Example 14

2-[2-(N,N-dimethylamino)ethyl]-6-methoxytetralin hydrochloride

Lithium aluminum hydride (0.25 g) was added to a THF solution (20 ml) of N,N-dimethyl-(6-methoxy-2-tetralin) acetamide (1.613 g; obtained in Reference Example 13). The reaction mixture was stirred at room temperature for 6 hours, to which was added water. Insoluble substances were removed from the reaction mixture through filtration, and the filtrate was concentrated. The residue was processed with a solution of 4 N hydrochloric acid-ethyl acetate to obtain its hydrochloride, which was then recrystallized from methanol-ethyl acetate to obtain the entitled compound (1.247 g).

m.p.: 183–185° C.

Reference Example 15

2-[N-Benzyl-N-(3,3-diphenylpropyl)aminolmethyl-6-methoxytetralin 2-(N-benzylamino)methyl-6-methoxytetralin hydrochloride (0.602 g; obtained in Reference Example 6), 3,3-diphenylpropyl iodide (0.803 g) and potassium carbonate (0.800 g) were added to DMF (20 ml). The reaction mixture was stirred at room temperature for 24 hours, and water was added thereto, which was then extracted with ethyl acetate. The organic layer was washed with water and a saturated aqueous sodium chloride solution, then dried, and concentrated. The residue was purified by silica gel column chromatography (eluent: ethyl acetate/hexane=1/1) to obtain the entitled compound (0.335 g).

$^1$H NMR δ: 1.11–1.40(1H,m), 1.70–2.05(2H,m), 2.13–2.48(7H,m), 2.62–2.88(3H,m), 3.54(2H,s), 3.76(3H,s), 3.98(1H,t,J=8 Hz), 6.55–6.70(2H,m), 6.95(1H,d,J=8 Hz), 7.04–7.38(15H,m).

Reference Example 16

2-(N,N-Dimethylamino)methyl-6-hydroxytetralin hydrochloride 2-(N,N-Dimethylamino)methyl-6-methoxytetralin hydrochloride (0.365 g; obtained in Reference Example 5) was added to 48% hydrobromic acid (10 ml), and the reaction mixture was heated under reflux for 3 hours, and then left cooled. This was neutralized with an aqueous solution of 1 N sodium hydroxide, and a solution of 10% potassium carbonate was added thereto, which was then extracted with ethyl acetate. The organic layer was washed with a saturated aqueous sodium chloride solution, then dried, and concentrated. The residue was purified by alumina column chromatography (eluent: ethyl acetate/hexane=1/2), and then processed with a solution of 4 N hydrochloric acid-ethyl acetate to obtain its hydrochloride. This was washed with ethyl acetate to obtain the entitled compound (0.211 g).

m.p.: 221–224° C.

Compounds of the following Reference Examples 17 to 22 were obtained in the same manner as in Reference Example 16.

Reference Example 17

2-(N,N-Dipropylamino)methyl-6-hydroxytetralin hydrochloride m.p.: 173–175° C.

Solvent for recrystallization: methanol-diisopropyl ether

Reference Example 18

2-[N-Benzyl-N-(3,3-diphenylpropyl)amino]methyl-6-hydroxytetralin $^1$H NMR δ: 1.10–1.34(1H,m), 1.68–2.02(2H,m), 2.12–2.48(7H,m), 2.57–2.87(3H,m), 3.55(2H,d,J=2 Hz), 3.98(1H,t,J=8 Hz), 6.48–6.60(2H,m), 6.89(1H,d,J=8 Hz), 7.04–7.34(15H,m).

Reference Example 19

6-Hydroxy-2-piperidinomethyltetralin hydrochloride m.p.: 216–218° C.
Solvent for recrystallization: methanol-diethyl ether

Reference Example 20

2-[2-(N,N-Dimethylamino)ethyl]-6-hydroxytetralin m.p.: 114–116° C.
Solvent for recrystallization: ethyl acetate-hexane

Reference Example 21

2-(N,N-Dimethylamino)methyl-7-hydroxytetralin hydrochloride m.p.: 197–198° C.
Solvent for recrystallization: methanol-ethyl acetate

Reference Example 22

6-Hydroxy-2-(N-methylamino)methyltetralin hydrochloride m.p.: 229–230° C.
Solvent for recrystallization: methanol-ethyl acetate

Reference Example 23

N-[6-(4-Biphenylyl)methoxy-2-tetralinyl] methylacetamide

Boron tribromide (1.57 g) was added to a methylene chloride (15 ml) solution of N-(6-methoxy-2-tetralinyl) methylacetamide (730 mg; obtained in Reference Example 12), at 0° C. The reaction mixture was warmed to room temperature, and stirred for 1 hour. Water was added to this, which was then extracted with ethyl acetate. The organic layer was washed with a saturated aqueous potassium carbonate solution, then dried, and concentrated. The residue was dissolved in DMF (20 ml), to which were added 4-(iodomethyl)biphenyl (1.35 g) and potassium carbonate (1.36 g). The reaction mixture was stirred at room temperature for 16 hours. Water was added to this, which was then extracted with ethyl acetate. The organic layer was washed with 1 N hydrochloric acid, a saturated aqueous sodium bicarbonate solution and a saturated aqueous sodium chloride solution, then dried, and concentrated. The residue was purified by silica gel column chromatography (eluent: ethyl acetate/hexane=1/1). The resulting crude crystals were recrystallized from ethyl acetate-diisopropyl ether to obtain the entitled compound (750 mg).

m.p.: 144–145° C.

Reference Example 24

Methyl (6-hydroxy-2-tetralin)acetate (6-Methoxy-2-tetralin)acetic acid (15.22 g) was added to 48% hydrobromic acid (100 ml), and the reaction mixture was heated under reflux for 3 hours. After this was cooled, water was added thereto, which was then extracted with ethyl acetate. The organic layer was washed with water and a saturated aqueous sodium chloride solution, then dried, and concentrated. The resulting residue was dissolved in methanol (200 ml), to which was dropwise added thionyl chloride (6.0 ml) at 0° C. The reaction mixture was stirred at room temperature for 2 hours, and then concentrated. Water was added to the residue, which was then extracted with ethyl acetate. The organic layer was washed with water and a saturated aqueous sodium chloride solution, then dried, and concentrated. The resulting crude crystals were recrystallized from ethyl acetate-hexane to obtain the entitled compound (9.566 g).

$^1$H NMR δ: 1.32–1.55(1H,m), 1.84–2.00(1H,m), 2.10–2.48(4H,m), 2.70–2.89(3H,m), 3.71(3H,s), 4.80(1H,s), 6.52–6.64(2H,m), 6.91(1H,d,J=8 Hz).

Reference Example 25

Methyl [6-(2-naphthyl)methoxy-2-tetralin]acetate

Methyl (6-hydroxy-2-tetralin)acetate (0.608 g; obtained in Reference Example 24), 2-naphthylmethyl bromide (0.737 g) and potassium carbonate (0.59 g) were added to DMF (20 ml). The reaction mixture was stirred at room temperature for 5 hours, and water was added thereto, which was then extracted with ethyl acetate. The organic layer was washed with water and a saturated aqueous sodium chloride solution, then dried, and concentrated. The residue was purified by silica gel column chromatography (eluent: ethyl acetate/hexane=1/4), and then recrystallized from ethyl acetate-hexane to obtain the entitled compound (0.624 g).

m.p.: 73–75° C.

Reference Example 26

2-(2-Hydroxyethyl)-6-(2-naphthyl)methoxytetralin

Lithium aluminum hydride (75 mg) was added to a THF solution (10 ml) of methyl [6-(2-naphthyl)methoxy-2-tetralin]acetate (0.712 g; obtained in Reference Example 25). The reaction mixture was stirred at room temperature for 2 hours, and then water was added thereto. Insoluble substances were removed from the reaction mixture through filtration, and the filtrate was concentrated. The resulting crystals were recrystallized from ethyl acetate-hexane to obtain the entitled compound (0.451 g).

m.p.: 90–91° C.

Reference Example 27

2-(2-Iodoethyl)-6-(2-naphthyl)methoxytetralin

P-Toluenesulfonyl chloride (0.301 g) was added to a dichloromethane solution (15 ml) of 2-(2-hydroxyethyl)-6-(2-naphthyl) methoxytetralin (0.712 g; obtained in Reference Example 26) and pyridine (0.19 ml), at 0° C. The reaction mixture was stirred at room temperature for 24 hours, and 1 N hydrochloric acid was added thereto, which was then extracted with dichloromethane. The organic layer was washed with water, a saturated aqueous sodium bicarbonate solution and a saturated aqueous sodium chloride solution, then dried, and concentrated. The residue was dissolved in acetone (10 ml), to which was added sodium iodide (0.371 g). The reaction mixture was heated under reflux for 4 hours, and then concentrated. A saturated aqueous sodium bicarbonate solution and an aqueous sodium thiosulfate solution were added to this, which was then extracted with ethyl acetate. The organic layer was washed with a saturated aqueous sodium chloride solution, then dried, and concentrated. The residue was purified by silica gel column chromatography (eluent: ethyl acetate/hexane=1/10) to obtain the entitled compound (0.451 g).

$^1$H NMR δ: 1.30–1.60(1H,m), 1.75–2.02(4H,m), 2.26–2.46(1H,m), 2.72–2.89(3H,m), 3.30(2H,t,J=7 Hz), 5.19(2H,s), 6.72–6.83(2H,m), 6.98(1H,d,J=8 Hz), 7.42–7.57 (3H,m), 7.78–7.91(4H,m).

Reference Example 28

Methyl [6-(4-biphenylyl)methoxy-2-tetralin]acetate

60% oily sodium hydride (1.034 g) was added to a DMF solution (100 ml) of methyl (6-hydroxy-2-tetralin) acetate (4.407 g; obtained in Reference Example 24), at 0° C. The reaction mixture was stirred at 40° C. for 1 hour, and then again cooled to 0° C., to which was then added 4-(chloromethyl)biphenyl (4.466 g). The reaction mixture was stirred at room temperature for 14 hours, and water was added thereto, which was then extracted with ethyl acetate. The organic layer was washed with water and a saturated aqueous sodium chloride solution, then dried, and concentrated. The resulting crude crystals were washed with diisopropyl ether to obtain the entitled compound (3.995 g).

m.p.: 65–70° C.

Reference Example 29

[6-(4-Biphenylyl)methoxy-2-tetralin]acetic acid

Methyl [6-(4-biphenylyl)methoxy-2-tetralin]acetate (3.480 g; obtained in Reference Example 28) was dissolved in THF (80 ml) and methanol (40 ml), to which was added an aqueous solution of 1 N sodium hydroxide (20 ml). The reaction mixture was stirred at room temperature for 7 hours, and then concentrated. 1 N hydrochloric acid was added to the residue until the resulting mixture became acidic, and this was then extracted with a mixed solvent of ethyl acetate and THF. The organic layer was washed with a saturated aqueous sodium chloride solution, then dried, and concentrated. The resulting crude crystals were recrystallized from THF-diisopropyl ether to obtain the entitled compound (2.956 g).

m.p.: 167–169° C.

Reference Example 30

6-[(4-Biphenylyl)methoxy-2-tetralin]-N,N-dimethylacetamide

[6-(4-Biphenylyl)methoxy-2-tetralin]acetic acid (1.866 g; obtained in Reference Example 29), dimethylamine hydrochloride (0.553 g), WSC (1.512 g), 1-hydroxybenzotriazole (0.764 g) and triethylamine (2.1 ml) were added to a mixture of acetonitrile (50 ml) and THF (50 ml). The reaction mixture was stirred at room temperature for 20 hours, and 1 N hydrochloric acid was added thereto, which was then extracted with ethyl acetate. The organic layer was washed with water, a saturated aqueous sodium bicarbonate solution and a saturated aqueous sodium chloride solution, then dried, and concentrated. The resulting crude crystals were recrystallized from ethyl acetate-hexane to obtain the entitled compound (1.497 g).

m.p.: 114–119° C.

Reference Example 31

6-Acetylamino-2-(N,N-dimethylamino)methyltetralin

A THF solution (40 ml) of 6-acetylamino-1-tetralone (1.692 g) was added to an acetonitrile solution (40 ml) of N,N-dimethylmethylene ammonium chloride (2.04 g), then stirred at room temperature for 24 hours, and concentrated. An aqueous solution of 10% potassium carbonate was added to the residue, which was then extracted with ethyl acetate. The organic layer was washed with a saturated aqueous sodium chloride solution, then dried, and concentrated. The residue was dissolved in methanol (50 ml), to which was added sodium borohydride (0.86 g). The reaction mixture was stirred at room temperature for 1 hour, and water was added thereto, which was then extracted with ethyl acetate. The organic layer was washed with a saturated aqueous sodium chloride solution, then dried, and concentrated. The residue was dissolved in methanol (50 ml), to which were added 10% palladium-carbon (0.4 g) and 1 N hydrochloric acid (20 ml). Then, this was catalytically reduced under a hydrogen pressure of 1 atmosphere, for 12 hours. The palladium-carbon was removed from the reaction mixture through filtration, the filtrate was concentrated, and an aqueous solution of 10% potassium carbonate was added thereto to form a free form compound. Then, this was extracted with ethyl acetate. The organic layer was washed with a saturated aqueous sodium chloride solution, then dried, and concentrated. The resulting crude crystals were recrystallized from ethyl acetate-hexane to obtain the entitled compound (1.862 g).

m.p.: 104–107° C.

Reference Example 32

6-Amino-2-(N,N-dimethylamino)methyltetralin

6-Acetylamino-2-(N,N-dimethylamino)methyltetralin hydrochloride (0.879 g; obtained in Reference Example 31) was added to 2 N hydrochloric acid. The reaction mixture was heated under reflux for 90 minutes, and then an aqueous solution of 1 N sodium hydroxide was added thereto to thereby make the resulting mixture have pH of 9. Then, this was extracted with ethyl acetate. The organic layer was washed with water and a saturated aqueous sodium chloride solution, then dried, and concentrated. The residue was purified by alumina column chromatography (eluent: ethyl acetate/hexane=1/1) to obtain the entitled compound (0.231 g).

$^1$H NMR δ: 1.24–1.47(1H,m), 1.60–2.00(3H,m), 2.13–2.40(2H,m), 2.24(6H,s), 2.66–2.89(3H,m), 3.23–2.73(2H,br), 6.42–6.52(2H,m), 6.89(1H,d,J=8 Hz).

Reference Example 33

6-(4-Bromobenzyl)oxy-2-(N,N-dimethylamino)methyltetralin 2-(N,N-Dimethylamino)methyl-6-hydroxytetralin (5.0 g; obtained in Reference Example 16) was dissolved in DMF (130 ml), to which was added 60% oily sodium hydride (1.46 g) at 0° C. The reaction mixture was warmed to room temperature, and stirred for 1 hour. This was again cooled to 0° C., to which was added a DMF solution (20 ml) of 4-bromobenzyl bromide (10.0 g). The reaction mixture was stirred at room temperature for 2 hours, and water was added thereto, which was then extracted with ethyl acetate. The organic layer was washed with water and a saturated aqueous sodium chloride solution, then dried, and concentrated. The residue was purified by alumina column chromatography (eluent: ethyl acetate/hexane=1/10) to obtain the entitled compound (3.4 g).

$^1$H NMR δ: 1.2–1.5(1H,m), 1.7–2.1(2H,m), 2.1–2.5(3H, m), 2.24(6H,s), 2.7–3.0(3H,m), 4.97(2H,s), 6.6–6.8(2H,m), 7.00(1H,d,J=8 Hz), 7.28(2H,d,J=8 Hz), 7.50(2H,d,J=8 Hz).

Compounds of the following Reference Examples 34 to 40 were obtained in the same manner as in Reference Example 33.

Reference Example 34

6-(3-Bromobenzyl)oxy-2-(N,N-dimethylamino) methyltetralin $^1$H NMR δ: 1.2–1.5(1H,m), 1.7–2.1(2H,m), 2.1–2.5(3H, m), 2.24(6H,s), 2.7–3.0(3H,m), 4.99(2H,s), 6.6–6.8(2H,m), 7.01(1H,d,J=8 Hz), 7.1–7.5(3H,m), 7.59(1H,s).

Reference Example 35

6-(2-Bromobenzyl)oxy-2-(N,N-dimethylamino) methyltetralin $^1$H NMR δ: 1.2–1.5(1H,m), 1.7–2.1(2H,m), 2.1–2.5(3H, m), 2.24(6H,s), 2.7–3.0(3H,m), 5.09(2H,s), 6.7–6.8(2H,m), 7.02(1H,d,J=8 Hz), 7.17(1H,td,J=7 Hz,2 Hz), 7.32(1H,td, J=7 Hz,2 Hz), 7.5–7.6(2H,m).

Reference Example 36

6-Benzyloxy-2-(N,N-dimethylamino)methyltetralin hydrochloride m.p.: 196–198° C.

Solvent for recrystallization: methanol-ethyl acetate

Reference Example 37

6-(2-Chlorobenzyl)oxy-2-(N,N-dimethylamino) methyltetralin hydrochloride m.p.: 203–207° C.

Solvent for recrystallization: methanol-diethyl ether

Reference Example 38

6-(2,4-Dichlorobenzyl)oxy-2-(N,N-dimethylamino) methyltetralin hydrochloride m.p.: 217–218° C.

Solvent for recrystallization: methylene chloride-diethyl ether

Reference Example 39

6-(4-Benzyloxybenzyl)oxy-2-(N,N-dimethylamino) methyltetralin hydrochloride m.p.: 208–209° C.

Solvent for recrystallization: ethanol-ethyl acetate

Reference Example 40

2-[N-Benzyl-N-(3,3-diphenylpropyl)amino]methyl-6-(2,4-dichlorobenzyl) oxytetralin hydrochloride This was amorphous powder.

$^1$H NMR δ: 1.12–1.35(1H,m), 1.72–2.06(2H,m), 2.14–2.48(7H,m), 2.54–2.88(3H,m), 3.55(2H,d,J=2 Hz), 3.98(1H,t,J=7 Hz), 5.07(2H,s), 6.63–6.74(2H,m), 6.96(1H, d,J=8 Hz), 7.06–7.34(15H,m), 7.37–7.53(3H,m).

IR (KBr): 3058, 3028, 2925, 2572, 1592, 1500, 1234, 747, 701 cm$^{-1}$.

Reference Example 41

Methyl [6-(4-bromobenzyl)oxy-2-tetralin]acetate

Methyl (6-hydroxy-2-tetralin)acetate (17.5 g), 4-bromobenzyl bromide (24.0 g) and potassium carbonate (30.6 g) were added to DMF (160 ml). The reaction mixture was stirred at room temperature for 12 hours, and water was added thereto, which was then extracted with ethyl acetate. The organic layer was washed with water and a saturated aqueous sodium chloride solution, then dried, and concentrated. The resulting crude crystals were recrystallized from toluene-diisopropyl ether to obtain the entitled compound (31.0 g).

m.p.: 78–79° C.

Reference Example 42

[6-(4-Bromobenzyl)oxy-2-tetralin]acetic acid

Methyl [6-(4-bromobenzyl)oxy-2-tetralin]acetate (31.0 g) was dissolved in methanol (200 ml), to which was added an aqueous solution of 1 N sodium hydroxide (200 ml). The reaction mixture was stirred at 80° C. for 4 hours, and then concentrated. 1 N hydrochloric acid was added to the residue until the resulting mixture became acidic, and this was then extracted with ethyl acetate. The organic layer was washed with a saturated aqueous sodium chloride solution, then dried, and concentrated. The resulting crude crystals were recrystallized from ethyl acetate-hexane to obtain the entitled compound (29.4 g).

m.p.: 145–146° C.

Reference Example 43

Methyl 3-(6-methoxy-2-methoxycarbonyl-1-oxo-2-tetralin) propionate

A 28% sodium methoxide-methanol solution (17.3 g) was added to a methanol solution (100 ml) of methyl (6-methoxy-1-oxo-2-tetralin)carboxylate (21 g; described in J. Am. Chem. Soc., Vol. 78, p. 461, 1951). To the reaction mixture was added a methanol solution (100 ml) of methyl acrylate (9.7 ml), and stirred at room temperature for 3 hours. The reaction mixture was poured into an aqueous solution of 10% citric acid, which was then extracted with ethyl acetate. The organic layer was washed with water and a saturated aqueous sodium chloride solution, then dried, and concentrated. The resulting crude crystals were recrystallized from ethyl acetate-diisopropyl ether to obtain the entitled compound (19.7 g).

m.p.: 66–67° C.

Reference Example 44

3-(6-Methoxy-1-oxo-2-tetralin)propionic acid

6 N Hydrochloric acid (150 ml) was added to an acetic acid solution (30 ml) of methyl 3-(6-methoxy-2-methoxycarbonyl-1-oxo-2-tetralin) propionate (17.7g), and heated under reflux for 2 hours. Water (200 ml) was added to the reaction mixture, and the crystals formed were taken out through filtration to obtain the entitled compound (13.3 g).

m.p.: 129–130° C.

Reference Example 45

4-(6-Methoxy-1-oxo-2-tetralin)butyric acid

Methyl 3-(6-methoxy-1-oxo-2-tetralin)carboxylate (20 g), ethyl 4-bromocrotonate (26.4 g) and potassium carbonate (23.6 g) were added to DMF (300 ml). The reaction mixture was stirred at 80° C. for 12 hours, and water was added thereto, which was then extracted with ethyl acetate. The organic layer was washed with water and a saturated aqueous sodium chloride solution, then dried, and concentrated. 10% palladium-carbon (3.0 g) was added to an ethanol solution (200 ml) of the residue, which was thus catalytically reduced under a hydrogen pressure of one atmosphere at room temperature for 12 hours. The catalyst was removed from the reaction mixture through filtration, and the filtrate was concentrated. 6 N hydrochloric acid (100 ml) was added to an acetic acid solution (50 ml) of the residue, and heated under reflux for 4 hours. Water (200 ml) was added to the reaction mixture, which was then extracted with ethyl acetate. The organic layer was washed with water and a saturated aqueous sodium chloride solution, then dried, and concentrated. The resulting crude crystals were recrystallized from ethyl acetate-diisopropyl ether to obtain the entitled compound (14.0 g).

m.p.: 91–92° C.

Reference Example 46

3-(6-Methoxy-2-tetralin)propionic acid

Perchloric acid (0.25 ml) and 10% palladium-carbon (1.0 g) were added to an acetic acid solution (50 ml) of 3-(6-methoxy-1-oxo-2-tetralin)propionic acid (10 g), which was thus catalytically reduced under a hydrogen pressure of one atmosphere at room temperature for 24 hours. The catalyst was removed from the reaction mixture through filtration, and the filtrate was concentrated. Water was added to the residue, which was then extracted with ethyl acetate. The organic layer was washed with water and a saturated aqueous sodium chloride solution, then dried, and concentrated. The resulting crude crystals were recrystallized from toluene-diisopropyl ether to obtain the entitled compound (6.6 g).

m.p.: 114–115° C.

Reference Example 47

4-(6-Methoxy-2-tetralin)butyric acid

The entitled compound was obtained in the same manner as in Reference Example 46.

m.p.: 100–101° C.

Solvent for recrystallization: toluene-diisopropyl ether

Reference Example 48

[6-(4-Bromobenzyl)oxy-2-tetralin]-N,N-dimethylacetamide

[6-(4-Bromobenzyl)oxy-2-tetralin]acetic acid (15.0 g), dimethylamine hydrochloride (4.24 g), WSC (12.0 g), 1-hydroxybenzotriazole (6.13 g) and triethylamine (16.7 ml) were added to a mixed solvent of acetonitrile (200 ml) and THF (200 ml). The reaction mixture was stirred at room temperature for 12 hours, and 1 N hydrochloric acid was added thereto, which was then extracted with ethyl acetate. The organic layer was washed with water, a saturated aqueous sodium bicarbonate solution and a saturated aqueous sodium chloride solution, then dried, and concentrated. The resulting crude crystals were recrystallized from ethyl acetate-hexane to obtain the entitled compound (14.3 g).

m.p.: 86–87° C.

Compounds of the following Reference Examples 49 and 50 were obtained in the same manner as in Reference Example 48.

Reference Example 49

N,N-Dimethyl-3-(6-methoxy-2-tetralin)propionamide

This was oily.

$^1$H NMR δ: 1.32–1.54(1H,m), 1.60–1.84(3H,m), 1.84–2.02(1H,m),2.26–2.50(3H,m), 2.70–2.90(3H,m), 2.95 (3H,s),3.03(3H,s), 3.76(3H,s), 6.56–6.72(2H,m), 6.97(1H,d, J=8 Hz).

Reference Example 50

N,N-Dimethyl-4-(6-methoxy-2-tetralin)butanamide

This was oily.

$^1$H NMR δ: 1.30–1.50(3H,m), 1.60–1.84(3H,m), 1.84–2.00(1H,m), 2.24–2.44(3H,m), 2.70–2.90(3H,m), 2.95 (3H,s), 3.01(3H,s), 3.76(3H,s), 6.56–6.72(2H,m), 6.97(1H, d,J=8 Hz).

Reference Example 51

6-(4-Bromobenzyl)oxy-2-[2-(N,N-dimethylamino) ethyl]tetralin hydrochloride

Lithium aluminum hydride (1.95 g) was added to a THF solution (300 ml) of [6-(4-bromobenzyl)oxy-2-tetralin]-N, N-dimethylacetamide (13.8 g). The reaction mixture was stirred at room temperature for 2 hours, and then an aqueous solution of 1 N sodium hydroxide was added thereto. Insoluble substances were removed from the reaction mixture through filtration, and the filtrate was concentrated. The residue was purified by silica gel column chromatography (eluent: ethyl acetate to methanol), and then processed with a solution of 4 N hydrochloric acid-ethyl acetate to form a hydrochloride. The thus-formed salt was recrystallized from methanol-ethyl acetate to obtain the entitled compound (10.5 g).

m.p.: 200–202° C.

Compounds of the following Reference Examples 52 and 53 were obtained in the same manner as in Reference Example 51.

Reference Example 52

2-[3-(N,N-Dimethylamino)propyl]-6-methoxytetralin hydrochloride m.p.: 163–164° C.

Solvent for recrystallization: methanol-diisopropyl ether

Reference Example 53

2-[4-(N,N-Dimethylamino)butyl]-6-methoxytetralin hydrochloride m.p.: 144–145° C.

Solvent for recrystallization: methanol-diisopropyl ether

Reference Example 54

2-[3-(N,N-Dimethylamino)propyl]-6-hydroxytetralin hydrochloride

2-[3-(N,N-Dimethylamino)propyl]-6-methoxytetralin hydrochloride (3.6 g) was added to 48% hydrobromic acid (20 ml), and the reaction mixture was heated under reflux for 3 hours, and then left cooled. This was neutralized with an aqueous solution of 1 N sodium hydroxide, and an aqueous solution of 10% potassium carbonate was added thereto, which was then extracted with ethyl acetate. The organic layer was washed with a saturated aqueous sodium chloride solution, then dried, and concentrated. The residue was recrystallized from methanol-diisopropyl ether to obtain the entitled compound (2.0 g).

m.p.: 110–111° C.

Reference Example 55

2-[4-(N,N-Dimethylamino)butyl]-6-hydroxytetralin hydrochloride

The entitled compound was obtained in the same manner as in Reference Example 54.

m.p.: 123–124° C.

Solvent for recrystallization: methanol-diisopropyl ether

Reference Example 56

N,N-Dimethyl-(6-methoxy-1-oxo-2-tetralin)acetamide

Dimethylamine hydrochloride (24.3 g, 298 mmols), WSC (66.0 g, 344 mmols) and 1-hydroxybenzotriazole hydrate (35.1 g, 230 mmols) were added to an acetonitrile solution (1 liter) of (6-methoxy-1-oxo-2-tetralin) acetic acid (53.8 g, 230 mmols; described in Eur. J. Med. Chem., Vol. 25, p. 765, 1990). Triethylamine (96 ml, 689 mmols) was added to the reaction mixture with cooling with ice, and stirred at room temperature for 48 hours. The reaction mixture was concentrated under reduced pressure, and water was added to the residue, which was then extracted with ethyl acetate. The organic layer was washed with water and a saturated aqueous sodium chloride solution, then dried, and concentrated under reduced pressure. The residue was recrystallized from ethyl acetate-toluene to obtain the entitled compound (34 g).

m.p.: 102–104° C.

Reference Example 57

N,N-Dimethyl[6-methoxy-2-(3,4-dihydronaphthalene)]acetamide

Sodium borohydride (15 g, 397 mmols) was divided into 3 portions, which were separately added to a methanol solution (1 liter) of N,N-dimethyl-(6-methoxy-1-oxo-2-tetralin) acetamide (44.7 g, 180 mmols) with cooling with ice. The reaction mixture was stirred at room temperature for 2 hours, then neutralized with 1 N hydrochloric acid, and concentrated under reduced pressure to about ⅓. Water was added to the concentrate, which was then extracted with ethyl acetate. The organic layer was washed with water and a saturated aqueous sodium chloride solution, then dried, and concentrated under reduced pressure. P-toluenesulfonic acid hydrate (700 mg, 4.06 mmols) was added to a toluene solution (700 ml) of the resulting residue, and heated under reflux for 30 minutes. The reaction mixture was washed with a saturated aqueous sodium bicarbonate solution and a saturated aqueous sodium chloride solution, then dried, and concentrated under reduced pressure. The residue was purified by silica gel column chromatography (eluent: hexane/ethyl acetate=1/1 to ethyl acetate alone) to obtain the entitled compound (37.5 g).

$^1$H NMR δ: 2.30(2H,t,J=8.0 Hz), 2.83(2H,t,J=8.0 Hz), 2.99(3H,s), 3.04(3H,s), 3.26(2H,s), 3.79(3H,s), 6.21(1H,s), 6.62–6.72(2H,m),6.86–6.96(1H,m).

Reference Example 58

(−)-N,N-Dimethyl-(6-methoxy-2-tetralin)acetamide

Degassed ethanol (160 ml) was added to N,N-dimethyl-[6-methoxy-2-(3,4-dihydronaphthalene)]acetamide (18.03 g, 73.50 mmols) and [RuCl$_2$[(R)-(BINAP)]]$_2$NEt$_3$ (1.24 g, 0.734 mmols), and the resulting solution was transferred into an autoclave, in which the solution was stirred under a hydrogen pressure of 100 kg/cm$^2$, at 70° C. for 6 hours. This was concentrated to dryness under reduced pressure, and the residue was subjected to silica gel column chromatography (eluent: hexane/ethyl acetate=1/2) to obtain the entitled compound (15.5 g, 98.3% e.e.).

m.p.: 70–71° C.

Solvent for recrystallization: ethyl acetate-hexane $[α]_D^{25}$=−61.3° (c=1.00, chloroform)

Elemental Analysis: for C$_{15}$H$_{21}$NO$_2$

| Calc.: | C | 72.84, | H | 8.56, | N | 5.66 |
|---|---|---|---|---|---|---|
| Found: | C | 72.76, | H | 8.49, | N | 5.79 |

Reference Example 59

(+)-N,N-Dimethyl-(6-methoxy-2-tetralin)acetamide

Degassed ethanol (160 ml) was added to N,N-dimethyl-[6-methoxy-2-(3,4-dihydronaphthalene)]acetamide (18.06 g, 73.50 mmols) and [RuCl$_2$[(S)-(BINAP)]]$_2$NEt$_3$ (1.24 g, 0.734 mmols), and the resulting solution was transferred into an autoclave, in which the solution was stirred under a hydrogen pressure of 100 kg/cm$^2$, at 70° C. for 6 hours. This was concentrated to dryness under reduced pressure, and the residue was subjected to silica gel column chromatography (eluent: hexane/ethyl acetate=1/2) to obtain the entitled compound (15.8 g, 98.7% e.e.).

m.p.: 71–72° C.

Solvent for recrystallization: ethyl acetate-hexane $[α]_D^{25}$=+63.70 (c=1.00, chloroform)

Elemental Analysis: for C$_{15}$H$_{21}$NO$_2$

| Calc.: | C | 72.84, | H | 8.56, | N | 5.66 |
|---|---|---|---|---|---|---|
| Found: | C | 72.68, | H | 8.42, | N | 5.65 |

Reference Example 60

(+)-2-[2-(N,N-Dimethylamino)ethyl]-6-methoxytetralin hydrochloride

Lithium aluminum hydride (0.203 g) was added to a THF solution (15 ml) of (+)-N,N-dimethyl-(6-methoxy-2-tetralin) acetamide (0.870 g). The reaction mixture was stirred at room temperature for 50 minutes, then heated under reflux for 30 minutes, and thereafter left cooled. Water was added to this, from which were removed insoluble substances through filtration, and the filtrate was then concentrated. The residue was purified by alumina column chromatography (eluent:hexane alone to ethyl acetate/hexane=1/10 to 1/4), and then processed with a solution of 4 N hydrochloric acid-ethyl acetate solution to form a hydrochloride. The thus-formed salt was recrystallized from methanol-diisopropyl ether to obtain the entitled compound (0.749 g).

m.p.: 195–197° C.

$[α]_D^{20}$=+68.2° (c=0.55, methanol)

Reference Example 61

(+)-2-[2-(N,N-Dimethylamino)ethyl]-6-hydroxytetralin hydrochloride (+)-2-[2-(N,N-Dimethylamino)ethyl]-6-methoxytetralin hydrochloride (0.602 g) was added to 48% hydrobromic acid (10 ml), and the reaction mixture was heated under reflux for 3.5 hours, and then left cooled. This was neutralized with an aqueous solution of 1 N sodium hydroxide, and a solution of 10% potassium carbonate was added thereto, which was then extracted with ethyl acetate. The organic layer was washed with a saturated aqueous sodium chloride solution, then dried, and concentrated. The residue was processed with a solution of 4 N hydrochloric acid-ethyl acetate to form a hydrochloride. The thus-formed salt was recrystallized from methanol-diisopropyl ether to obtain the entitled compound (0.490 g).

m.p.: 213–215° C.

$[\alpha]_D^{20}$=+69.1° (c=0.52, methanol)

Reference Example 62

(−)-2-[2-(N,N-dimethylamino)ethyl]-6-methoxytetralin hydrochloride

Lithium aluminum hydride (0.130 g) was added to a THF solution (15 ml) of (−)-N,N-dimethyl-(6-methoxy-2-tetralin) acetamide (0.807 g). The reaction mixture was stirred at room temperature for 15 minutes, then heated under reflux for 15 minutes, and thereafter left cooled. Water was added to this, from which were removed insoluble substances, and the filtrate was concentrated. The residue was purified by alumina column chromatography (eluent: hexane alone to ethyl acetate/hexane=1/4), and then processed with a solution of 4 N hydrochloric acid-ethyl acetate to form a hydrochloride. The thus-formed salt was recrystallized from methanol-diisopropyl ether to obtain the entitled compound (0.683 g).

m.p.: 193–195° C.

$[\alpha]_D^{20}$=−68.0° (c=0.49, methanol)

Reference Example 63

(−)-2-[2-(N,N-Dimethylamino)ethyl]-6-hydroxytetralin hydrochloride (−)-2-[2-(N,N-Dimethylamino)ethyl]-6-methoxytetralin hydrochloride (0.563 g) was added to 48% hydrobromic acid (10 ml), and the reaction mixture was heated under reflux for 4 hours, and then left cooled. This was neutralized with an aqueous solution of 1 N sodium hydroxide, and a solution of 10% potassium carbonate was added thereto, which was then extracted with ethyl acetate. The organic layer was washed with a saturated aqueous sodium chloride solution, then dried, and concentrated. The residue was processed with a solution of 4 N hydrochloric acid-ethyl acetate to form a hydrochloride. The thus-formed salt was recrystallized from methanol-diisopropyl ether to obtain the entitled compound (0.480 g).

m.p.: 213–215° C.

$[\alpha]_D^{20}$=−69.9° (c=0.55, methanol)

Reference Example 64

6-(4-Biphenylyl)methoxy-2-(2-hydroxyethyl)tetralin

To a suspension of lithium aluminum hydride (4.71 g) in THF (200 ml) was added a solution of methyl 6-(4-biphenylyl) methoxy-2-tetralinacetate (24.0 g) in THF (50 ml) under ice-cooling. The reaction mixture was stirred at room temperature for 2 hr and diluted with saturated aqueous Rochelle salt. The precipitate was filtered off and the filtrate was concentrated. The residue was recrystallized from ethyl acetate-hexane to obtain the titled compound (22.1 g).

m.p.: 101–102° C.

Reference Example 65

6-(4-Biphenylyl)methoxy-2-(2-iodoethyl)tetralin

To a solution of triphenylphosphine (12.5 g) in THF (200 ml) were successively added imidazole (3.25 g) and iodine (12.1 g). A solution of 6-(4-biphenylyl) methoxy-2-(2-hydroxyethyl)tetralin (13.15 g) in THF (100 ml) was added to the reaction mixture at room temperature. The reaction mixture was stirred at room temperature for 5 min, diluted with water, and extracted with ethyl acetate. The organic layer was washed with aqueous sodium thiosulfate and saturated aqueous sodium chloride, dried, and concentrated. The residue was purified by silica gel column chromatography (eluent; toluene) to obtain the titled compound (13.2 g).

$^1$H NMR δ: 1.30–1.60 (1H, m), 1.75–2.00 (4H, m), 2.20–2.46 (1H, m), 2.72–2.92 (3H, m), 3.30 (2H, t, J=7 Hz), 5.07 (2H, s), 6.70–6.84 (2H, m), 6.99 (1H, d, J=8 Hz), 7.14–7.66 (9H, m).

Reference Example 66

(+)-6-(4-Bromobenzyl)oxy-2-[2-(N,N-dimethylamino) ethyl]tetralin hydrochloride

To a suspension of (+)-2-[2-(N,N-dimethylamino) ethyl]-6-hydroxytetralin (9.2 g) in toluene (180 ml) was added sodium hydride (60% in oil, 2.0 g). After stirring at 50° C. for 30 min, a solution of 4-bromobenzyl chloride (9.7 g) in toluene (45 ml) was added to the reaction mixture, which was heated under reflux for one hr. The reaction mixture was diluted with water and concentrated. The residue was diluted with water and extracted with ethyl acetate. The organic layer was washed with saturated aqueous sodium chloride, dried, and concentrated. The residue was dissolved in solvent mixture of ethyl acetate/hexane (1:4) and the precipitate was filtered off. The filtrate was concentrated and the residue was purified by alumina column chromatography (eluent: ethyl acetate: hexane=1:50 to 1:4) and converted into its hydrochloride. The crystals were washed with diisopropyl ether to obtain the titled compound (17.0 g).

m.p.: 191–193° C.

$[\alpha]_D^{20}$=+44.1° (c=0.99 in methanol).

Reference Example 67

N,N-Diethyl-(6-methoxy-1-oxo-2-tetralin)acetamide

To a solution of (6-methoxy-1-oxo-2-tetralin) acetic acid (30 g) in acetonitrile (500 ml) were added diethylamine (18.7 g), WSC (36.8 g), and 1-hydroxybenzotriazole (19.6 g). The reaction mixture was stirred at room temperature for 2 days and concentrated. The residue was diluted with ethyl acetate and washed with 0.5 N aqueous hydrochloric acid, and saturated aqueous sodium bicarbonate. The organic layer was dried and concentrated. The residue was purified by silica gel column chromatography (eluent; hexane: ethyl acetate=1:1) and further recrystallized from ethyl acetate-diisopropyl ether to obtain the titled compound (26.8 g).

m.p.: 88–89° C.

Reference Example 68

N,N-Diethyl-[6-methoxy-2-(3,4-dihydronaphthalene)]acetamide

To a solution of N,N-diethyl-(6-methoxy-1-oxo-2-tetralin) acetamide (25 g) in methanol (400 ml) was added sodium borohydride (6.54 g) in an ice bath. After stirring at room temperature for 30 min, the reaction mixture was neutralized by adding 1 N aqueous hydrochloric acid. The reaction mixture was concentrated and extracted with ethyl acetate. The organic layer was washed with water, saturated aqueous sodium bicarbonate, and saturated aqueous sodium chloride, dried, and concentrated. The residue was dissolved in degassed toluene (300 ml) followed by addition of p-toluenesulfonic acid monohydrate (20 mg). The reaction mixture was heated under reflux for 1 hr and cooled to room temperature. The reaction mixture was diluted with ethyl acetate and washed with saturated aqueous sodium bicarbonate, dried and concentrated. The residue was purified by silica gel column chromatography (eluent; hexane: ethyl acetate=1:1) to obtain the titled compound (23.1 g).

$^1$H NMR δ: 1.10–1.25 (6H, m), 2.31 (2H, t, J=7.6 Hz), 2.82 (2H, t, J=7.6 Hz), 3.23 (2H, s), 3.26–3.48 (4H, m), 3.78(3H, s), 6.22 (1H, s), 6.62–6.72 (2H, m), 6.84–6.96 (1H, m).

Reference Example 69

(+)-N,N-Diethyl-(6-methoxy-2-tetralin)acetamide

N,N-Diethyl-[6-methoxy-2-(3,4-dihydronaphthalene)] acetamide (10.0 g) and Ru$_2$Cl$_4$[(S)-BINAP]$_2$NEt$_3$ (618 mg) were added to degassed ethanol (170 ml). The reaction mixture was stirred under hydrogen (100 kg/cm$^2$) at 70° C. for 6 hr in an autoclave. The reaction mixture was concentrated and the residue was purified by silica gel column chromatography (eluent; hexane: ethyl acetate=2:1) and alumina column chromatography (eluent; hexane: ethyl acetate=4:1) to obtain the titled compound (8.8 g).

[α]$_D^{20}$=+54.0° (c=1.000 in methanol).

$^1$H NMR δ: 1.00–1.22 (6H, m), 1.30–1.56 (1H, m), 1.88–2.08 (1H, m), 2.20–2.50 (4H, m), 2.70–3.00 (3H, m), 3.26–3.46 (4H, m), 3.77 (3H, s), 6.60–6.75 (2H, m), 6.96 (1H, d, J=8.0 Hz). Optical purity: 94% e.e. (by HPLC analysis).

Reference Example 70

(−)-N,N-Diethyl-(6-methoxy-2-tetralin)acetamide

N,N-Diethyl-[6-methoxy-2-(3,4-dihydronaphthalene)] acetamide (10.0 g) and Ru$_2$Cl$_4$[(R)-BINAP]$_2$NEt$_3$ (618 mg) were added to degassed ethanol(170 ml). The reaction mixture was stirred under hydrogen (100 kg/cm$^2$) at 70° C. for 6 hr in an autoclave. The reaction mixture was concentrated and the residue was purified by silica gel column chromatography (eluent; hexane: ethyl acetate=2:1) and further purified by alumina column chromatography (eluent; hexane: ethyl acetate=4:1) to obtain the titled compound (8.88 g).

[α]$_D^{20}$=−53.0° (c=0.799 in methanol).

$^1$H NMR δ: 1.00–1.22 (6H, m), 1.30–1.56 (1H, m), 1.88–2.08 (1H, m), 2.20–2.50 (4H, m), 2.70–3.00 (3H, m), 3.26–3.46 (4H, m), 3.77 (3H, s), 6.60–6.75 (2H, m), 6.96 (1H, d, J=8.0 Hz). Optical purity: 93.7% e.e. (by HPLC analysis).

Reference Example 71

(+)-2-[2-(N,N-Diethylamino)ethyl]-6-methoxy-2-tetralin hydrochloride

To a solution of (+)-N,N-diethyl-(6-methoxy-2-tetralin) acetamide (8.8 g) in THF (150 ml) was added lithium aluminum hydride (1.45 g). The reaction mixture was stirred at room temperature and diluted with 1 N aqueous sodium hydroxide. The precipitate was removed by filtration and the filtrate was concentrated. The residue was purified by alumina column chromatography (eluent; hexane: ethyl acetate=10:1) and converted into its hydrochloride, which was recrystallized from methanol-diisopropyl ether to obtain the titled compound (5.4 g).

m.p.: 144–145° C.

[α]$_D^{20}$=+61.5° (c=1.000 in methanol)

Reference Example 72

(−)-2-[2-(N,N-Diethylamino)ethyl]-6-methoxytetralin hydrochloride

The titled compound was obtained by the similar procedure as in Reference Example 71.

m.p.: 144–145° C. (recrystallizing solvent: methanol-diisopropyl ether).

[α]$_D^{20}$=−60.8° (c=0.055 in methanol).

Reference Example 73

(+)-2-[2-(N,N-Diethylamino)ethyl]-6-hydroxytetralin (+)-2-[2-(N,N-Diethylamino)ethyl]-6-methoxytetralin hydrochloride (5.2 g) was added to 48% hydrobromic acid (10 ml) and the reaction mixture was heated under reflux for 4 hr and cooled. The reaction mixture was neutralized with 1 N aqueous sodium hydroxide followed by addition of 10% aqueous potassium carbonate and extracted with the combined solvent of ethyl acetate and THF (1:1). The organic layer was washed with saturated aqueous sodium chloride, dried, and concentrated. The residue was recrystallized from methanol-diisopropyl ether to obtain the titled compound (4.5 g).

m.p.: 102–104° C.

[α]$_D^{20}$=+73.8° (c=0.226 in methanol).

Reference Example 74

(−)-2-[2-(N,N-Diethylamino)ethyl]-6-hydroxytetralin

The titled compound was synthesized from Reference Example 72, using similar method as in Reference Example 73.

m.p.: 103–104° C. (recrystallizing solvent; methanol-diisopropyl ether).

[α]$_D^{20}$=−73.4° (c=1.001 in methanol).

Reference Example 75

[6-(4-Biphenylyl)methoxy-2-tetralin]-N-[2-(N,N-dimethylamino) ethyl]-N-methylacetamide hydrochloride To a solution of [6-(4-biphenylyl)methoxy-2-tetralin] acetic acid (999 mg, Reference Example 29) in THF (15 ml) was added oxalyl chloride (0.28 ml) at 0° C. Two drops of DMF was added and the reaction mixture was stirred at room temperature for 2 hr. The reaction mixture was concentrated and the residue was dissolved in acetonitrile (30 ml) and THF (10 ml) and a solution of N,N,N'-trimethylethylenediamine (309mg) and triethylamine (0.56 ml) in acetonitrile (5 ml) were added to the reaction mixture at 0° C. The reaction mixture was stirred at room temperature for one hr, diluted with water, and extracted with ethyl acetate. The organic layer was washed with water and saturated aqueous sodium chloride, dried, and concentrated. The residue was purified by alumina column chromatography (eluent: ethyl acetate: hexane=1:2) and converted into its hydrochloride, which was then recrystallized from methanol-diisopropyl ether to obtain the titled compound (1.159 g).

m.p.: 190–194° C.

Reference Example 76

[6-(4-Biphenylyl)methoxy-2-tetralin]-N-[2-(N,N-diethylamino) ethyl]-N-methylacetamide hydrochloride To a solution of [6-(4-biphenylyl)methoxy-2-tetralin] acetic acid (501 mg, Reference Example 29) in THF (15 ml) was added oxalyl chloride (0.13 ml) at 0° C. Two drops of DMF was added and the reaction mixture was stirred at room temperature for 40 min. The reaction mixture was concentrated and the residue was dissolved in acetonitrile (20 ml) and a solution of N,N-diethyl-N'-methylethylenediamine (216 mg) and triethylamine (0.28 ml) in acetonitrile (10 ml) was added at 0° C. The reaction mixture was stirred at room temperature for 45 min, diluted with water, and extracted with ethyl acetate. The organic layer was washed with water and saturated aqueous sodium chloride, dried, and concentrated. The residue was purified by alumina column chromatography (eluent: ethyl acetate: hexane=1:2) and converted into its hydrochloride, which was then recrystallized from ethanol-diisopropyl ether to obtain the titled compound (603 mg).

m.p.: 148–151° C.

Reference Example 77

[6-(4-Biphenylyl)methoxy-2-tetralin]-N-methylacetamide

A mixture of [6-(4-biphenylyl)methoxy-2-tetralin]acetic acid (1.180 g, Reference Example 29), methylamine hydrochloride (0.496 g), 1-hydroxybenzotriazole (0.509 g), WSC (0.719 g), and triethylamine (1.4 ml) in THF (30 ml) and acetonitrile (30 ml) was stirred at room temperature for 10 days. The reaction mixture was diluted with 10% aqueous citric acid and extracted with ethyl acetate. The organic layer was washed with water, saturated aqueous sodium bicarbonate, and saturated aqueous sodium chloride, dried and concentrated. The crude crystals were washed with diisopropyl ether to obtain the titled compound (0.947 g).

m.p.: 156–159° C.

Reference Example 78

[6-(4-Biphenylyl)methoxy-2-tetralin]-N-ethylacetamide

A mixture of [6-(4-biphenylyl)methoxy-2-tetralin]acetic acid (4.051 g, Reference Example 29), ethylamine hydrochloride (1.143 g), 1-hydroxybenzotriazole (1.647 g), WSC (2.536 g), and triethylamine (4.5 ml) in THF (80 ml) and acetonitrile (80 ml) was stirred at room temperature for one day. The reaction mixture was diluted with 10% aqueous citric acid and extracted with ethyl acetate. The organic layer was washed with water, saturated aqueous sodium bicarbonate, and saturated aqueous sodium chloride, dried and concentrated. The crude crystals were washed with diisopropyl ether to obtain the titled compound (4.216 g).

m.p.: 168–172° C.

Reference Example 79

2-(4-Benzylpiperazin-1-yl)methyl-6-methoxytetralin dihydrochloride

2-Iodomethyl-6-methoxytetralin (1.209 g, Reference Example 8), 1-benzylpiperazine (0.852 g), and potassium carbonate (0.853 g) were added to DMF (15 ml). The reaction mixture was stirred at room temperature for 18 hr, diluted with water, and extracted with ethyl acetate. The organic layer was washed with water and saturated aqueous sodium chloride, dried, and concentrated. The residue was purified by silica gel column chromatography (eluent: ethyl acetate) and converted into its dihydrochloride, which was further washed with diethyl ether to obtain the titled compound (1.217 g).

m.p.: 227–230° C. (decomposed).

Reference Example 80

2-(4-Benzylpiperazin-1-yl)methyl-6-hydroxytetralin dihydrochloride 2-(4-Benzylpiperazin-1-yl)methyl-6-methoxytetralin dihydrochloride (0.849 g) was added to conc. hydrochloric acid (20 ml) and the reaction mixture was heated under reflux for 6 hr and cooled. The resulting precipitate was collected and washed with ethanol, methanol, and diethyl ether to obtain the titled compound (0.523 g).

m.p.: 230–236° C. (decomposed).

Reference Example 81

Dimethyl (4-methoxy-2-nitrophenyl) methylidenemalonate

A mixture of 4-methoxy-2-nitrobenzaldehyde (21.3 g, Org. Synth., Vol. V, p-139, 1973), dimethyl malonate (16.5 g), piperidine (2.5 ml), and acetic acid (0.25 ml) in methanol (125 ml) was heated under reflux for 24 hr. The reaction mixture was concentrated, diluted with 1 N aqueous hydrochloric acid, and extracted with ethyl acetate. The organic layer was washed with 10% aqueous potassium carbonate and saturated aqueous sodium chloride, dried, and concentrated. The residue was purified by silica gel column chromatography (eluent: ethyl acetate: hexane=1:2) to obtain the titled compound (25 g).

$^1$H NMR δ: 3.67 (3H, s), 3.88 (3H, s), 3.92 (3H, s), 7.16 (1H, dd, J=8.8, 2.6 Hz), 7.36 (1H, d, J=8.8 Hz), 7.70 (1H, d, J=2.6 Hz), 8.14 (1H, s).

Reference Example 82

Dimethyl (4-methoxy-2-nitrobenzyl)malonate

To a solution of dimethyl (4-methoxy-2-nitrophenyl) methylidenemalonate (25 g) in methanol (200 ml) was added sodium borohydride (3.36 g) in an ice bath. After stirring at room temperature for 1 hr, the reaction mixture was neutralized by adding 1 N aqueous hydrochloric acid. The reaction mixture was concentrated and extracted with ethyl acetate. The organic layer was washed with water, saturated aqueous sodium bicarbonate, and saturated aqueous sodium chloride, dried and concentrated. The residue was purified by silica gel column chromatography (eluent:ethyl acetate: hexane=1:4) to obtain the titled compound (19 g).

$^1$H NMR δ: 3.44 (2H, d, J=7.2 Hz), 3.71 (6H, s), 3.86 (3H, s), 3.80–4.00 (1H, m), 7.08 (1H, dd, J=10.8, 2.4 Hz), 7.28 (1H, d, J=10.8 Hz), 7.52 (1H, d, J=2.4 Hz).

Reference Example 83

1,2,3,4-Tetrahydro-7-methoxy-2-oxo-3-quinolinecarboxylic acid

A solution of dimethyl (4-methoxy-2-nitrobenzyl) malonate (19 g) in ethanol (200 ml) was hydrogenated in the presence of 10% palladium-C (2.0 g) at room temperature under one atmosphere of hydrogen for 24 hr. The reaction mixture was further stirred at 80° C. for 24 hr and the catalyst was removed by filtration. The filtrate was concentrated. The residue was dissolved in the combined solvent of THF (250 ml) and methanol (250 ml) and 1 N aqueous sodium hydroxide (126 ml) was added in an ice bath. The reaction mixture was stirred at room temperature for 72 hr and concentrated. The residue was made acidic by adding 1 N aqueous hydrochloric acid and the precipitate was collected by filtration. The crude crystals were washed with acetone to obtain the titled compound (11.7 g).

m.p.: 145–146° C. (decomposed).

Reference Example 84

1,2,3,4-Tetrahydro-7-methoxy-N,N-dimethyl-2-oxo-3-quinolinecarboxamide

To a solution of 1,2,3,4-tetrahydro-7-methoxy-2-oxo-3-quinolinecarboxylic acid (3.74 g), dimethylamine hydrochloride (3.44 g), 1-hydroxybenzotriazole (2.85 g), and triethylamine (8.5 g) in acetonitrile (400 ml) was added WSC (6.5 g). The reaction mixture was stirred at room temperature for 24 hr and concentrated. The residue was diluted with ethyl acetate and the organic layer was washed with 1 N aqueous hydrochloric acid, 10% aqueous potassium carbonate, and saturated aqueous sodium chloride, dried, and concentrated. The resulting crude crystals were recrystallized from ethyl acetate-hexane to obtain the titled compound (1.63 g).

m.p.: 209–210° C.

Reference Example 85

3-(N,N-Dimethylamino)methyl-1,2,3,4-tetrahydro-7-methoxyquinoline dihydrochloride To a solution of 1,2,3,4-tetrahydro-7-methoxy-N,N-dimethyl-2-oxo-3-quinolinecarboxamide (1.63 g) in THF (100 ml) was added 1M borane-THF complex (60 ml). The reaction mixture was heated under reflux for 24 hr. The reaction mixture was concentrated and the residue was heated under reflux with 6 N aqueous hydrochloric acid (30 ml) for 4 hr. The reaction mixture was made basic by adding 6 N aqueous sodium hydroxide and extracted with ethyl acetate. The organic layer was washed with 10% aqueous potassium carbonate, saturated aqueous sodium chloride, dried, and concentrated. The residue was converted into its dihydrochloride, which was then recrystallized from methanol-diisopropyl ether to obtain the titled compound (1.27 g).

m.p.: 150–151° C.

Reference Example 86

3-(N,N-Dimethylamino)methyl-1,2,3,4-tetrahydro-7-quinolinol

A solution of 3-(N,N-dimethylamino)methyl-1,2,3,4-tetrahydro-7-methoxyquinoline dihydrochloride (1.0 g) 48% hydrobromic acid (10 ml) was heated under reflux for 4 hr. The reaction mixture was poured into 10% aqueous potassium carbonate and extracted with ethyl acetate. The organic layer was dried and concentrated. The resulting crude crystals were recrystallized from ethyl acetate-hexane to obtain the titled compound (0.81 g). The melting point of its dihydrochloride was 151–152° C. (recrystallizing solvent; methanol-diisopropyl ether).

Reference Example 87

Methyl 2,3,4,5-tetrahydro-8-methoxy-2-oxo-1H-1-benzazepine-4-carboxylate

Methyl 4-hydroxyimino-6-methoxytetralin-2-carboxylate (2.909 g, Journal of Medicinal Chemistry, 21, 1105–1110, 1978) was heated with polyphosphoric acid (30.22 g) at 100° C. for 1.5 hr and cooled. Ice-water was added to the reaction mixture, which was extracted with ethyl acetate. The organic layer was washed with water and saturated aqueous sodium chloride, dried, and concentrated. The resulting crude crystals were recrystallized from ethyl acetate-hexane to obtain the titled compound (2.125 g).

m.p.: 114–116° C.

Reference Example 88

2,3,4,5-Tetrahydro-8-methoxy-2-oxo-1H-1-benzazepine-4-carboxylic acid

To a solution of methyl 2,3,4,5-tetrahydro-8-methoxy-2-oxo-1H-1-benzazepine-4-carboxylate (5.035 g) in methanol (60 ml) was added 1 N aqueous sodium hydroxide (40 ml). The reaction mixture was stirred at room temperature for 6.5 hr, made acidic by adding 1 N aqueous hydrochloric acid, and extracted with ethyl acetate. The organic layer was washed with water and saturated aqueous sodium chloride, dried, and concentrated. The resulting crude crystals were washed with diethyl ether to obtain the titled compound (4.253 g).

m.p.: 202–204° C.

Reference Example 89

Methyl (1,2,3,4-tetrahydro-7-hydroxy-2-oxo-3-quinoline) acetate 2,3,4,5-Tetrahydro-8-methoxy-2-oxo-1H-1-benzazepine-4-carboxylic acid (4.013 g) was heated with 48% hydrobromic acid (40 ml) for 14 hr and cooled. The reaction mixture was diluted with water and extracted with ethyl acetate. The organic layer was washed with water and saturated aqueous sodium chloride, dried, and concentrated. The residue was dissolved in methanol (100 ml) and thionyl chloride (1.3 ml) was added to the solution at 0° C. After stirring for 3 hr, the reaction mixture was diluted with water and extracted with ethyl acetate. The organic layer was washed with water and saturated aqueous sodium chloride, dried, and concentrated. The crude crystals were washed with diethyl ether to obtain the titled compound (3.239 g).

m.p.: 174–177° C.

Reference Example 90

Methyl [7-(4-biphenylyl)methoxy-1,2,3,4-tetrahydro-2-oxo-3-quinoline]acetate

A mixture of methyl [1,2,3,4-tetrahydro-7-hydroxy-2-oxo-3-quinoline]acetate (3.025 g), 4-chloromethylbiphenyl (2.864 g), and potassium carbonate (2.137 g) in DMF (80 ml) was stirred at room temperature for 5 days. The reaction mixture was diluted with water and extracted with a combined solvent of ethyl acetate and THF. The organic layer was washed with water and saturated aqueous sodium chloride, dried, and concentrated. The resulting crude crystals were washed with ethyl acetate-hexane to obtain the titled compound (4.540 g).

m.p.: 174–178° C.

Reference Example 91

[7-(4-Biphenylyl)methoxy-1,2,3,4-tetrahydro-2-oxo-3-quinoline]acetic acid

To a solution of methyl [7-(4-biphenylyl)methoxy-1,2,3,4-tetrahydro-2-oxo-3-quinoline]acetate (2.475 g) in THF (60 ml) were added methanol (30 ml) and 1 N aqueous sodium hydroxide (12 ml). After stirring at room temperature for 2 days, the reaction mixture was made acidic by adding 1 N aqueous hydrochloric acid and extracted with combined solvent of ethyl acetate and THF. The organic layer was washed with water and saturated aqueous sodium chloride, dried, and concentrated. The resulting crystals were washed with diisopropyl ether to obtain the titled compound (1.895 g).

m.p.: 193–206° C. (decomposed).

Reference Example 92

[7-(4-Biphenylyl)methoxy-1,2,3,4-tetrahydro-2-oxo-3-quinoline]-N,N-dimethylacetamide A mixture of [7-(4-biphenylyl)methoxy-1,2,3,4-tetrahydro-2-oxo-3-quinoline]acetic acid (1.616 g), dimethylamine hydrochloride (0.674 g), 1-hydroxybenzotriazole (0.648 g), WSC (0.980 g), and N-methylmorpholine (2.0 ml) in THF (50 ml) and acetonitrile (50 ml) was stirred at room temperature for 2 days. The reaction mixture was diluted with 10% aqueous citric acid and extracted with ethyl acetate. The organic layer was washed with water, saturated aqueous sodium bicarbonate, and saturated aqueous sodium chloride and dried, and concentrated. The crude crystals were washed with diisopropyl ether to obtain the titled compound (1.557 g).

m.p.: 199–202° C.

Reference Example 93

N,N-Dimethyl-(6-hydroxy-1-oxo-2-tetralin) acetamide

A mixture of (6-hydroxy-1-oxo-2-tetralin)acetic acid (1.672 g, EP140684), dimethylamine hydrochloride (0.754 g), 1-hydroxybenzotriazole (1.468 g), and WSC (2.255 g), and triethylamine (3.1 ml) in THF (30 ml) and acetonitrile (30 ml) was stirred at room temperature for 36 hr. The reaction mixture was diluted with 10% aqueous citric acid and extracted with ethyl acetate. The organic layer was washed with water, saturated aqueous sodium bicarbonate, and saturated aqueous sodium chloride, dried, and concentrated. The crude crystals were recrystallized from methanol-diisopropyl ether to obtain the titled compound (0.744 g).

m.p.: 181–186° C.

Reference Example 94

[6-(4-Biphenylyl)methoxy-1-oxo-2-tetralin]-N,N-dimethylacetamide

To a solution of N,N-dimethyl-(6-hydroxy-1-oxo-2-tetralin) acetamide (0.313 g), 4-chloromethylbiphenyl (0.300g) in DMF (5 ml) was added sodium hydride (60% in oil, 80 mg) and the reaction mixture was stirred at room temperature for 15 hr. The reaction mixture was diluted with water and extracted with ethyl acetate. The organic layer was washed with water and saturated aqueous sodium chloride, dried, and concentrated. The residue was purified by silica gel column chromatography (eluent; hexane: ethyl acetate= 2:1). The resulting crystals were washed with diisopropyl ether to obtain the titled compound (0.200 g).

m.p.: 131–135° C.

Reference Example 95

[6-(4-Biphenylyl)methoxy-2-(3,4-dihydronaphthalene) ]-N,N-dimethylacetamide

To a solution of [6-(4-biphenylyl)methoxy-1-oxo-2-tetralin]-N,N-dimethylacetamide (0.954 g) in ethyl acetate (20 ml) and methanol (20 ml) was added sodium borohydride (0.175 g) at room temperature. After stirring at room temperature for 30 min, the reaction mixture was diluted with water and extracted with ethyl acetate. The organic layer was washed with water and saturated aqueous sodium chloride, dried, and concentrated. The residue was dissolved in toluene (30 ml) and heated under reflux in the presence of pyridinium p-toluenesulfonate (0.030 g) for 1.5 hr. After cooling, the reaction mixture was diluted with water and extracted with ethyl acetate. The organic layer was washed with water, saturated aqueous sodium bicarbonate, and saturated aqueous sodium chloride, dried, and concentrated. The resulting crystals were recrystallized from ethyl acetate-hexane to obtain the titled compound (0.779 g).

m.p.: 125–130° C.

Reference Example 96

6-(4-Biphenylyl)methoxy-2-[2-(imidazol-1-yl) ethyl]tetralin

The titled compound was synthesized using similar method as in Example 38.

m.p.: 145–146° C. (recrystallizing solvent; ethyl acetate-hexane).

Reference Example 97

2-[6-(4-Biphenylyl)methoxy-2-tetralin]ethyl-N,N-dimethylamine oxide m-chlorobenzoate 6-(4-Biphenylyl)methoxy-2-[2-(N,N-dimethylamino) ethyl]tetralin hydrochloride (1.269 g) was converted into its free form and dissolved in acetone (15 ml). 70% m-Chloroperbenzoic acid (0.777 g) was added to the solution at 0° C. The reaction mixture was stirred at 0° C. for 25 min and precipitated crystals were collected by filtration. The crystals were washed with ethyl acetate and diethyl ether successively and recrystallized from THF-ethyl acetate to obtain the titled compound (0.811 g).

m.p.: 125–128° C.

Reference Example 98

2-[6-(4-Biphenylyl)methoxy-2-tetralin]ethyl-N,N-diethylamine oxide 6-(4-Biphenylyl)methoxy-2-[2-(N,N-diethylamino) ethyl]tetralin hydrochloride (134 mg) was converted into its free form and dissolved in acetone (5 ml). 70% m-Chloroperbenzoic acid (83 mg) was added to the solution at 0° C. The reaction mixture was stirred at 0° C. for one hr and diluted with 1 N aqueous sodium hydroxide and extracted with ethyl acetate. The organic layer was washed with water and saturated aqueous sodium chloride, dried, and concentrated. The crude product was recrystallized from ethyl acetate-hexane to obtain the titled compound (120 mg).

m.p.: 99–104° C.

Reference Example 99

(+)-6-(2-Bromopyridin-5-yl)methoxy-2-[2-(N,N-dimethylamino) ethyl]tetralin dihydrochloride To a solution of (+)-2-[2-(N,N-dimethylamino) ethyl]-6-hydroxytetralin (0.220 g) in DMF (5 ml) was added sodium hydride (60% in oil, 0.049 g) at room temperature. The reaction mixture was stirred at 50° C. for 30 min. To the reaction mixture, cooled at 0° C., was added a solution of 2-bromo-5-pyridylmethylbromide (0.462g) in THF (5 ml). After stirring at 0° C. for 2 hr, the reaction mixture was diluted with water and extracted with ethyl acetate. The organic layer was washed with water and saturated aqueous sodium chloride, dried, and concentrated. The residue was purified by alumina column chromatography (eluent: ethyl acetate: hexane=1:4) and converted into its dihydrochloride, which was recrystallized from ethanol-ethyl acetate to obtain the titled compound (295 mg).

m.p.: 171–181° C. (decomposed).

$[\alpha]_D^{20}$=+41.2° (c=0.500 in methanol).

Reference Example 100

N-[2-(N,N-Dimethylamino)methyl-6-tetralinyl]-4-biphenylcarboxamide hydrochloride 6-Amino-2-(N,N-dimethylamino)methyltetralin (0.216 g; obtained in Reference Example 32) was dissolved in pyridine (10 ml), to which was added 4-biphenylcarbonyl chloride (0.311 g). The reaction mixture was stirred at room temperature for 12 hours, pyridine was evaporated out under reduced pressure, and water was added to the resulting residue, which was then extracted with ethyl acetate. The organic layer was washed with water and a saturated aqueous sodium chloride solution, then dried, and concentrated. The residue was purified by alumina column chromatography (eluent: ethyl acetate/hexane=1/1), and then processed with 4 N hydrochloric acid-ethyl acetate to form a hydrochloride. The thus-formed salt was recrystallized from methanol-ethyl acetate to obtain the entitled compound (0.224 g).

m.p.: >250° C.

$^1$H NMR δ: 1.24–1.54(1H,m), 1.84–2.10(2H,m), 2.20–2.50(3H,m), 2.26(6H,s), 2.79–3.01(3H,m), 7.10(1H,d, J=8 Hz), 7.28–7.54(5H,m), 7.60–7.82(5H,m), 7.94(2H,d, J=8 Hz).

IR (KBr): 3028, 2910, 2640, 1658, 1538, 1417, 746, 701 cm$^{-1}$.

EXAMPLE 1

6-(4-Biphenylyl)methoxy-2-(N,N-dimethylamino) methyltetralin hydrochloride

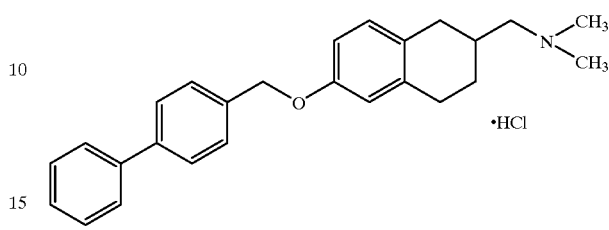

2-(N,N-Dimethylamino)methyl-6-hydroxytetralin (0.151 g, free base of the compound obtained in Reference Example 16) was dissolved in DMF (5 ml), to which was added 60% oily sodium hydride (92 mg) at 0° C. The reaction mixture was warmed to room temperature, and then stirred for 30 minutes. This was again cooled to 0° C., to which was added 4-(chloromethyl)biphenyl (0.183 g) and stirred at room temperature for 3 hours. Water was added to the reaction mixture, which was then extracted with ethyl acetate. The organic layer was washed with water and a saturated aqueous sodium chloride solution, then dried, and concentrated. The residue was purified by silica gel column chromatography (eluent: ethyl acetate/hexane=1/1 to ethyl acetate/methanol=10/1), and then processed with 4 N hydrochloric acid-ethyl acetate to form a hydrochloride. The thus-formed salt was recrystallized from methanol-diethyl ether to obtain the entitled compound (0.210 g).

m.p.: 229–233° C.

Compounds of the following Examples 2 to 11 were obtained in the same manner as in Example 1.

EXAMPLE 2

2-(N,N-Dimethylamino)methyl-6-(2-naphthyl) methoxytetralin hydrochloride

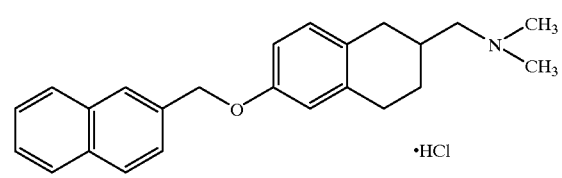

m.p.: 228–229° C.

Solvent for recrystallization: methanol-ethyl acetate

EXAMPLE 3

6-(2'-Cyanobiphenyl-4-yl)methoxy-2-(N,N-dimethylamino) methyltetralin hydrochloride

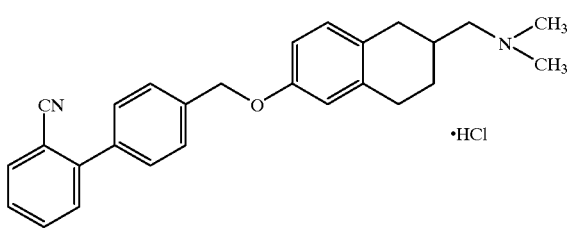

m.p.: 202–203° C.

Solvent for recrystallization: ethanol-ethyl acetate

EXAMPLE 4

7-(4-Biphenylyl)methoxy-2-(N,N-dimethylamino) methyltetralin hydrochloride

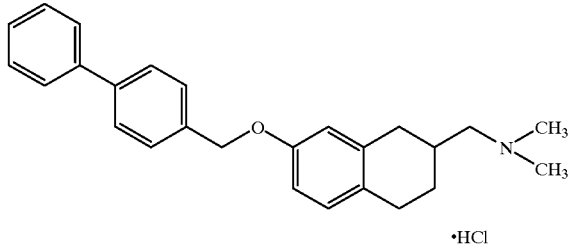

m.p.: 232–233° C.

Solvent for recrystallization: ethanol-ethyl acetate

EXAMPLE 5

2-(N,N-Dimethylamino)methyl-7-(2-naphthyl) methoxytetralin hydrochloride

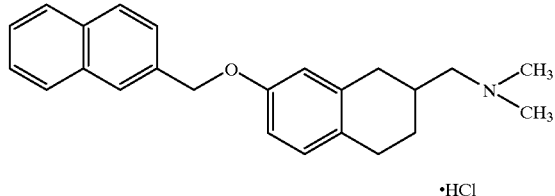

m.p.: 201–202° C.

Solvent for recrystallization: ethanol-ethyl acetate

EXAMPLE 6

6-(4-Biphenylyl)methoxy-2-(N-methylamino) methyltetralin hydrochloride

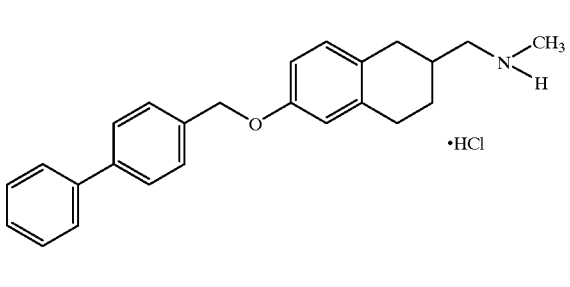

m.p.: 189–190° C.

Solvent for recrystallization: ethanol-ethyl acetate

EXAMPLE 7

6-(2-Naphthyl)methoxy-2-piperidinomethyltetralin hydrochloride

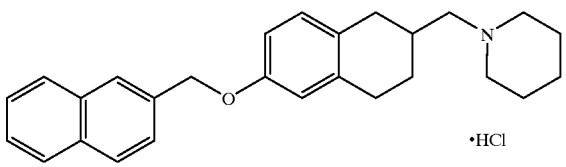

m.p.: 215–218° C. (decomposed).

Solvent for recrystallization: methanol-diethyl ether

EXAMPLE 8

2-[N-Benzyl-N-(3,3-diphenylpropyl)amino]methyl-6-(2-naphthyl) methoxytetralin hydrochloride

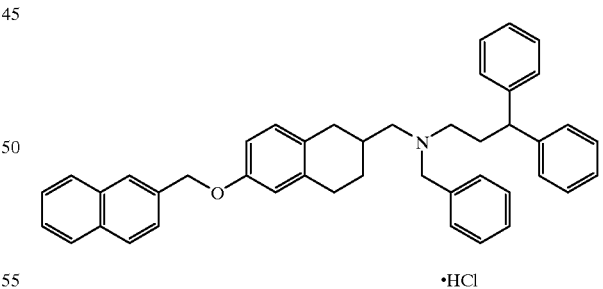

This was amorphous powder.

$^1$H NMR δ: 1.12–1.36(1H,m), 1.70–2.05(2H,m), 2.13–2.48(7H,m), 2.61–2.89(3H,m), 3.55(2H,d,J=2 Hz), 3.98(1H,t,J=8 Hz), 5.18(2H,s), 6.69–6.81(2H,m), 6.96(1H, d,J=8 Hz), 7.04–7.34(15H,m), 7.41–7.56(3H,m), 7.78–7.90 (4H,m).

IR (KBr): 3058, 3028, 2925, 2578, 1602, 1500, 1452, 1270, 1232, 747, 701 cm$^{-1}$.

EXAMPLE 9

6-(4-Biphenylyl)methoxy-2-(N,N-dipropylamino)methyltetralin hydrochloride

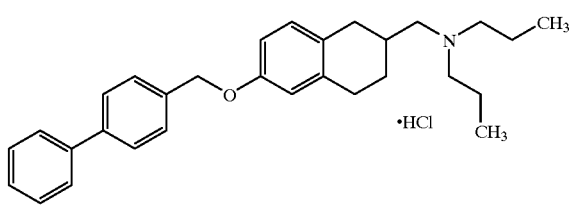

m.p.: 164–166° C.

Solvent for recrystallization: methanol-diisopropyl ether

EXAMPLE 10

6-[N-Acetyl-N-(4-biphenylyl)methyl]amino-2-(N,N-dimethylamino) methyltetralin hydrochloride

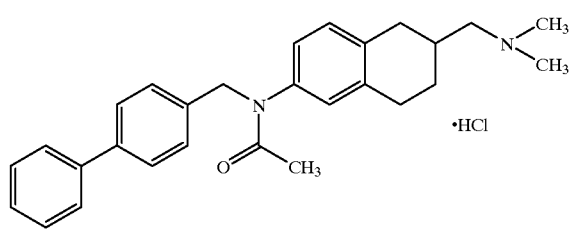

Solvent for recrystallization: methanol-ethyl acetate m.p.: 179–182° C.

EXAMPLE 11

6-[N-Acetyl-N-(2-naphthyl)methyl]amino-2-(N,N-dimethylamino) methyltetralin hydrochloride

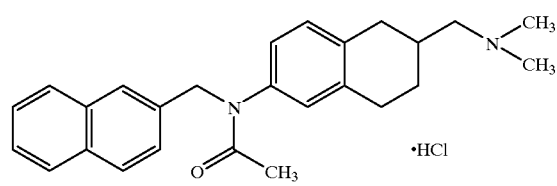

This was amorphous powder.

$^1$H NMR δ: 1,20–1.45(1H,m), 1.76–2.00(2H,m), 1.93 (3H,s), 2.08–2.44(3H,m), 2.24(6H,s), 2.64–2.76(2H,m), 2.82–2.96(1H,m), 5.02(2H,s), 6.64–6.76(2H,m), 6.98(1H,d, J=8 Hz), 7.36–7.50(3H,m), 7.61(1H,br,s), 7.70–7.86(3H,m).

IR (KBr): 3394, 2929, 2669, 1648, 1500, 1401, 1295, 821, 757 cm$^{-1}$.

EXAMPLE 12

6-(4-Biphenylyl)methoxy-2-[2-(N,N-dimethylamino) ethyl]tetralin hydrochloride

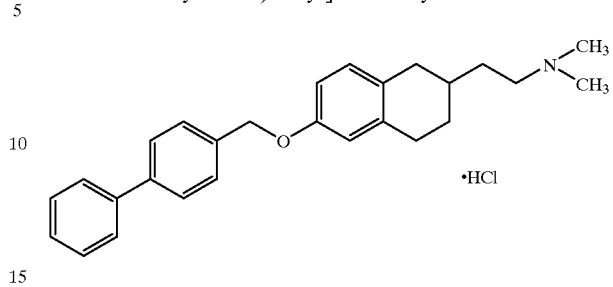

[6-(4-Biphenylyl)methoxy-2-tetralin]-N,N-dimethylacetamide (1.497 g; obtained in Reference Example 30) was dissolved in anhydrous THF (20 ml), to which was added lithium aluminum hydride (0.222 g). The reaction mixture was stirred at room temperature for 40 minutes, and then heated under reflux for 40 minutes. This was left cooled, and water was added thereto, from which were removed insoluble substances through filtration. The filtrate was concentrated. The residue was purified by silica gel column chromatography (eluent: ethyl acetate/hexane=1/1 to ethyl acetate alone to ethyl acetate/methanol=10/1), and then processed with 4 N hydrochloric acid-ethyl acetate to form a hydrochloride. The thus-formed salt was recrystallized from methanol-diisopropyl ether to obtain the entitled compound (1.022 g).

m.p.: 223–226° C. (decomposed).

EXAMPLE 13

2-[2-(N,N-Dipropylamino)ethyl]-6-(2-naphthyl)methoxytetralin hydrochloride

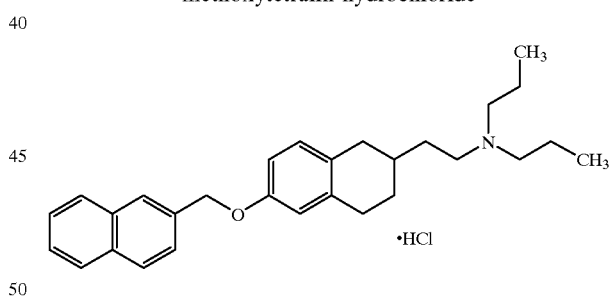

2-(2-Iodoethyl)-6-(2-naphthyl)methoxytetralin (0.193 g; obtained in Reference Example 27) was dissolved in DMF (5 ml), to which were added N,N-dipropylamine (0.09 ml) and anhydrous potassium carbonate (0.135 g). The reaction mixture was stirred at room temperature for 5 hours, and water was added thereto, which was then extracted with ethyl acetate. The organic layer was washed with water and a saturated aqueous sodium chloride solution, then dried, and concentrated. The residue was purified by silica gel column chromatography (eluent: ethyl acetate/hexane=1/1 to ethyl acetate/methanol=10/1), and the processed with 4 N hydrochloric acid-ethyl acetate to form a hydrochloride. The thus-formed salt was recrystallized from ethyl acetate-diisopropyl ether to obtain the entitled compound (0.105 g).

m.p.: 146–148° C.

EXAMPLE 14

6-(2-Naphthyl)methoxy-2-[2-(4-phenylpiperidino)ethyl]tetralin hydrochloride

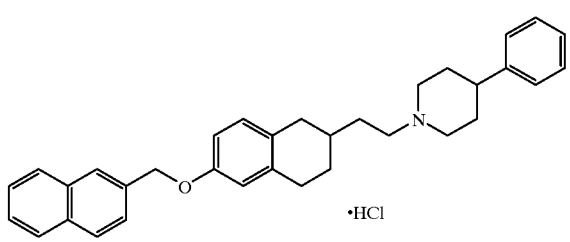

The entitled compound was obtained in the same manner as in Example 13.

m.p.: 229–234° C. (decomposed).
Solvent for recrystallization: methanol-diisopropyl ether

EXAMPLE 15

6-(4-Biphenylyl)methoxy-2-[2-(N,N-dimethylamino) ethyl]-3,4-dihydronaphthalene

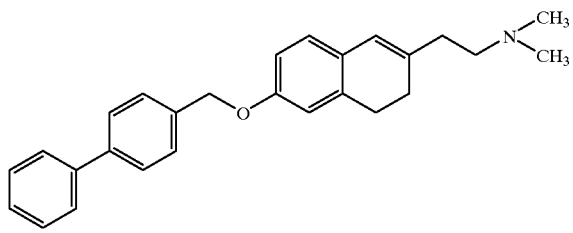

To a solution of [6-(4-biphenylyl)methoxy-2-(3,4-dihydronaphthalene)]-N,N-dimethylacetamide (205 mg) in THF (10 ml) was added lithium aluminum hydride (20 mg) at 0° C. The reaction mixture was diluted with water and the precipitate was removed by filtration. The filtrate was concentrated and the residue was purified by alumina column chromatography (eluent: ethyl acetate: hexane=1:4). The crude crystals were recrystallized from ethyl acetate-hexane to obtain the titled compound (46 mg).

m.p.: 123–126° C.

EXAMPLE 16

N-[2-(N,N-Dimethylamino)methyltetralin-6-yl]-2-naphthalenesulfonamide hydrochloride

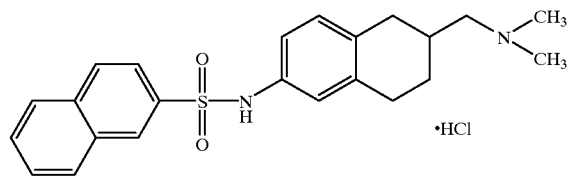

The entitled compound was obtained in the same manner as in Reference Example 100. This was amorphous powder.
$^1$H NMR δ: 1.16–1.40(1H,m), 1.72–1.97(2H,m), 2.08–2.38(3H,m), 2.21(6H,s), 2.60–2.90(3H,m), 6.74–6.84 (2H,m), 6.90(1H,d,J=8 Hz), 7.52–7.68(2H,m), 7.72(1H,dd, J=9 Hz,2 Hz), 7.82–7.94(3H,m), 8.36(1H,br,s). IR (KBr): 3394, 2927, 2698, 1614, 1504, 1320, 1156, 962, 821, 751, 657 cm$^{-1}$.

EXAMPLE 17

6-[N-(4-Biphenylyl)methyl]amino-2-(N,N-dimethylamino) methyltetralin

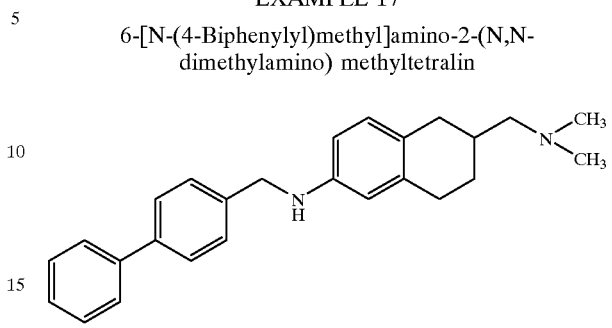

1 M Borane-THF complex (2 ml) was added to a THF solution (3 ml) of N-[2-(N,N-dimethylamino)methyl-6-tetralinyl]-4-biphenylcarboxamide (0.172 g; free base of the compound of Reference Example 100), and the reaction mixture was heated under reflux for 1 hour. Water was added to this, and then 6 N hydrochloric acid was added thereto, and stirred at room temperature for 1 hour. Then, the reaction mixture was made basic with an aqueous solution of 1 N sodium hydroxide added thereto, and thereafter extracted with ethyl acetate. The organic layer was washed with water and a saturated aqueous sodium chloride solution, then dried, and concentrated. The concentrate was purified by alumina column chromatography (eluent: ethyl acetate/hexane=1/4), and then recrystallized from ethyl acetate-hexane to obtain the entitled compound (0.060 g).

m.p.: 106–108° C.

EXAMPLE 18

2-(N,N-Dimethylamino)methyl-6-(4'-methoxybiphenyl-4-yl) methoxytetralin hydrochloride

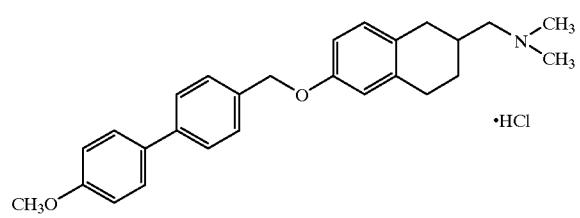

6-(4-Bromobenzyl)oxy-2-(N,N-dimethylamino) methyltetralin (374 mg; obtained in Reference Example 33) and tetrakis-(triphenylphosphine) palladium (35 mg) were dissolved in toluene (8 ml), to which were added an ethanol solution (1 ml) of 4-methoxyphenylboric acid (198 mg) and an aqueous 2 M sodium carbonate solution (1 ml). The reaction mixture was heated under reflux for 6 hours in an argon atmosphere. A saturated aqueous sodium chloride solution was added to this, which was then extracted with ethyl acetate. The organic layer was dried, and then concentrated. The residue was purified by alumina column chromatography (eluent: ethyl acetate/hexane 1/10), and then processed with 4 N hydrochloric acid-ethyl acetate to form a hydrochloride. The thus-formed salt was recrystallized from ethanol-ethyl acetate to obtain the entitled compound (0.290 g).

m.p.: 210–211° C.

Compounds of the following Examples 19 to 35 were obtained in the same manner as in Example 18.

EXAMPLE 19

2-(N,N-Dimethylamino)methyl-6-(4'-methylbiphenyl-4-yl) methoxytetralin hydrochloride

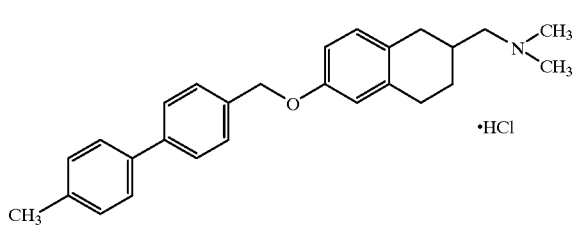

m.p.: 226–228° C.

Solvent for recrystallization: ethanol-ethyl acetate

EXAMPLE 20

2-(N,N-Dimethylamino)methyl-6- (4'-formylbiphenyl-4-yl) methoxytetralin hydrochloride

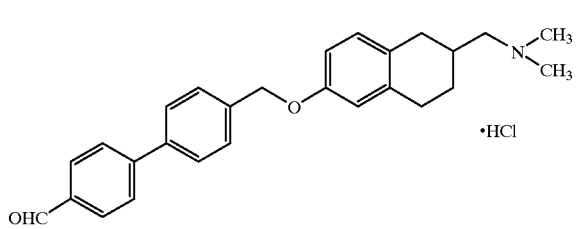

m.p.: 234–235° C.

Solvent for recrystallization: ethanol-ethyl acetate

EXAMPLE 21

2-(N,N-Dimethylamino)methyl-6-(4'-methylthiobiphenyl-4-yl) methoxytetralin hydrochloride

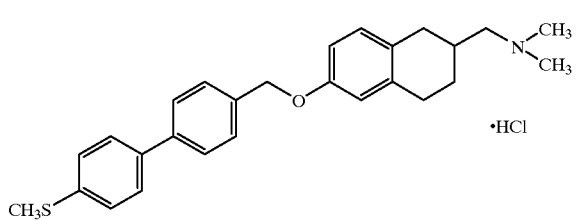

m.p.: 235–237° C.

Solvent for recrystallization: ethanol-ethyl acetate

EXAMPLE 22

2-(N,N-Dimethylamino)methyl-6-(4'-fluorobiphenyl-4 -yl) methoxytetralin hydrochloride

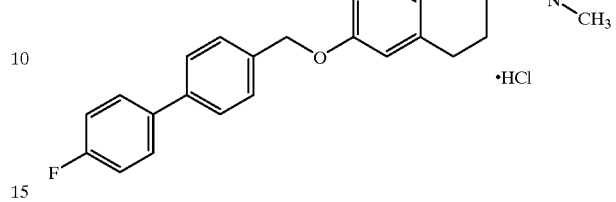

m.p.: 223–234° C.

Solvent for recrystallization: ethanol-ethyl acetate

EXAMPLE 23

2-(N,N-Dimethylamino)methyl-6-(3'-nitrobiphenyl-4-yl) methoxytetralin hydrochloride

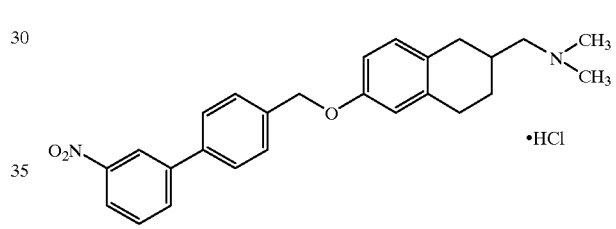

m.p.: 223–234° C.

Solvent for recrystallization: ethanol-ethyl acetate

EXAMPLE 24

2-(N,N-Dimethylamino)methyl-6-(3'-methoxybiphenyl-4-yl) methoxytetralin hydrochloride

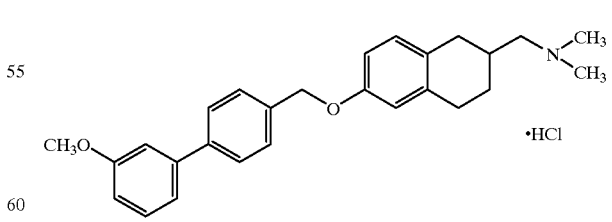

m.p.: 207–208° C.

Solvent for recrystallization: ethanol-ethyl acetate

EXAMPLE 25

2-(N,N-Dimethylamino)methyl-6-(2'-methoxybiphenyl-4-yl) methoxytetralin hydrochloride

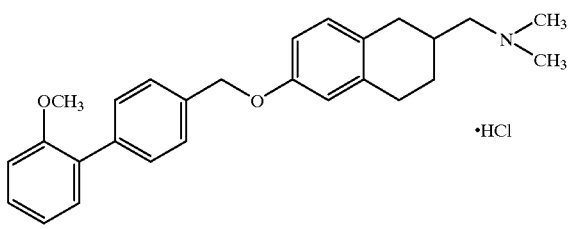

m.p.: 140–141° C.

Solvent for recrystallization: ethanol-ethyl acetate

EXAMPLE 26

2-(N,N-Dimethylamino)methyl-6-[3',5'-bis(trifluoromethyl)biphenyl-4-yl]methoxytetralin hydrochloride

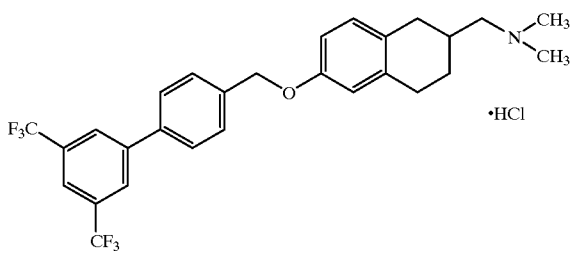

m.p.: 196–197° C.

Solvent for recrystallization: ethanol-ethyl acetate

EXAMPLE 27

2-(N,N-Dimethylamino)methyl-6-[4-(3-thienyl)benzyl]oxytetralin hydrochloride

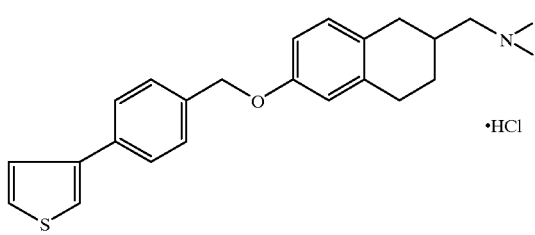

m.p.: 222–223° C.

Solvent for recrystallization: ethanol-ethyl acetate.

EXAMPLE 28

2-(N,N-Dimethylamino)methyl-6-[4-(2-thienyl)benzyl]oxytetralin hydrochloride

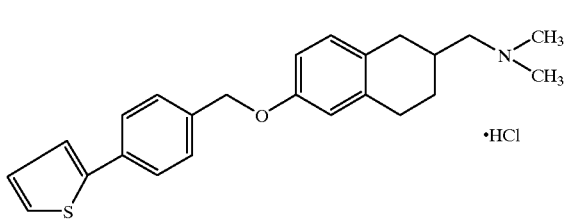

m.p.: 227–228° C.

Solvent for recrystallization: methanol-diisopropyl ether

EXAMPLE 29

2-(N,N-Dimethylamino)methyl-6-[4-(3-pyridyl)benzyl]oxytetralin dihydrochloride

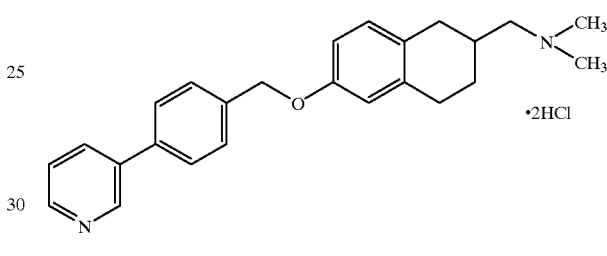

m.p.: 212–213° C.

Solvent for recrystallization: methanol-diisopropyl ether

EXAMPLE 30

6-(3-Biphenylyl)methoxy-2-(N,N-dimethylamino)methyltetralin hydrochloride

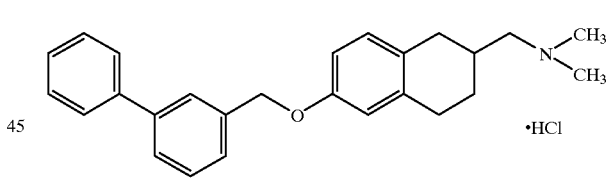

m.p.: 186–190° C.

Solvent for recrystallization: ethanol-ethyl acetate

EXAMPLE 31

2-(N,N-Dimethylamino)methyl-6-(4'-methoxybiphenyl-3-yl) methoxytetralin hydrochloride

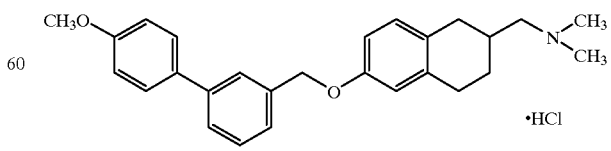

m.p.: 182–183° C.

Solvent for recrystallization: ethanol-ethyl acetate

EXAMPLE 32

2-(N,N-Dimethylamino)methyl-6-(4'-fluorobiphenyl-3-yl) methoxytetralin hydrochloride

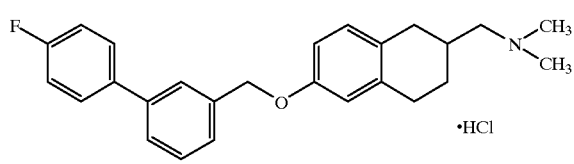

m.p.: 171–172° C.

Solvent for recrystallization: ethanol-ethyl acetate

EXAMPLE 33

6-(2-Biphenylyl)methoxy-2-(N,N-dimethylamino)methyltetralin hydrochloride

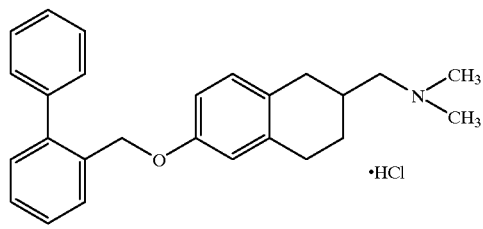

m.p.: 173–174° C.

Solvent for recrystallization: ethanol-ethyl acetate

EXAMPLE 34

2-(N,N-Dimethylamino)methyl-6-(4'-methoxybiphenyl-2-yl) methoxytetralin hydrochloride

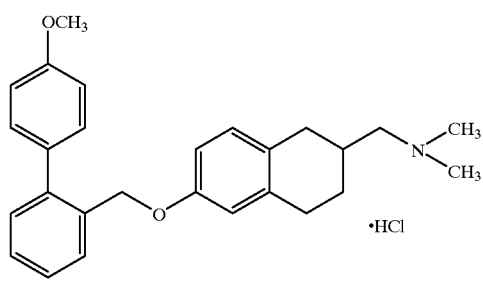

m.p.: 170–171° C.

Solvent for recrystallization: ethanol-ethyl acetate

EXAMPLE 35

2-(N,N-Dimethylamino)methyl-6-(4'-fluorobiphenyl-2-yl) methoxytetralin hydrochloride

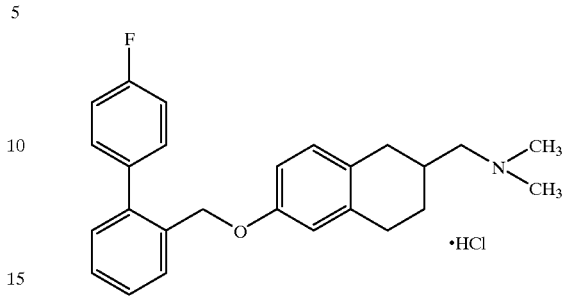

m.p.: 172–174° C.

Solvent for recrystallization: ethanol-ethyl acetate

EXAMPLE 36

6-(4-Biphenylyl)methoxy-2-(N-ethylamino)methyltetralin hydrochloride

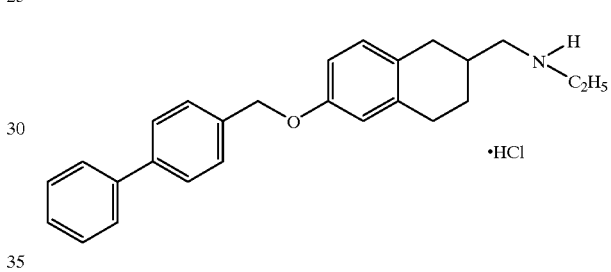

N-[6-(4-Biphenylyl)methoxy-2-tetralinyl)]methylacetamide (500 mg; obtained in Reference Example 23) was dissolved in THF (10 ml), to which was added lithium aluminum hydride (50 mg), and stirred at room temperature for 1 hour. An aqueous solution of sodium potassium tartrate was added to the reaction mixture with cooling with ice, from which were removed insoluble substances through filtration, and the filtrate was concentrated. The residue was processed with 4 N hydrochloric acid-ethyl acetate, and then recrystallized from ethanol-diisopropyl ether to obtain the entitled compound (0.138 g).

m.p.: 229–230° C.

EXAMPLE 37

2-(N,N-Dimethylamino)methyl-6-(4'-ethylbiphenyl-4-yl) methoxytetralin hydrochloride

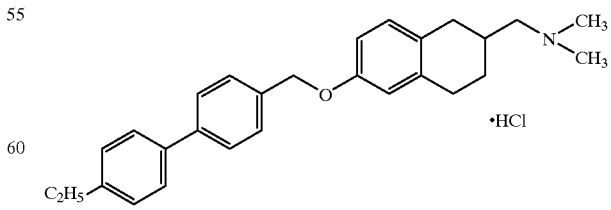

2-(N,N-Dimethylamino)methyl-6-hydroxytetralin (300 mg; obtained in Reference Example 16), (4'-ethylbiphenyl-4-yl) methanol (372 mg) and triphenylphosphine (460 mg)

were dissolved in THF (5 ml), to which was dropwise added diethyl azodicarboxylate (305 mg) with cooling with ice. The reaction mixture was stirred at room temperature for 4 hours, and then the solvent was evaporated out. Water was added to the residue, which was then extracted with ethyl acetate. The organic layer was washed with a saturated aqueous sodium bicarbonate solution and a saturated aqueous sodium chloride solution, then dried, and concentrated. The residue was purified by alumina column chromatography (eluent: ethyl acetate/hexane=1/10), and then processed with a solution of 4 N hydrochloric acid-ethyl acetate to form a hydrochloride. The thus-formed salt was recrystallized from ethanol-diisopropyl ether to obtain the entitled compound (310 mg).

m.p.: 229–230° C.

EXAMPLE 38

6-(4-Biphenylyl)methoxy-2-[2-(N,N-diethylamino) ethyl]tetralin hydrochloride

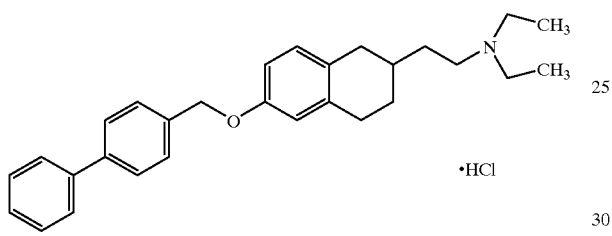

6-(4-Biphenylyl)-2-(2-iodoethyl)methoxytetralin (2.50 g), diethylamine (1.03 g) and potassium carbonate (1.95 g) were added to DMF (20 ml). The reaction mixture was stirred at room temperature for 24 hours, to which water was added. The crystals thus formed were taken out through filtration, then washed with ethyl acetate, and recrystallized from ethanol-diisopropyl ether. The crystals were processed with 4 N hydrochloric acid-ethyl acetate to form a hydrochloride. The thus-formed salt was recrystallized from ethanol-diisopropyl ether to obtain the entitled compound (1.53 g).

m.p.: 141–143° C.

Compounds of the following Examples 39 to 42 were obtained in the same manner as in Example 38.

EXAMPLE 39

6-(4-Biphenylyl)methoxy-2-[2-(pyrrolidin-1-yl) ethyl]tetralin hydrochloride

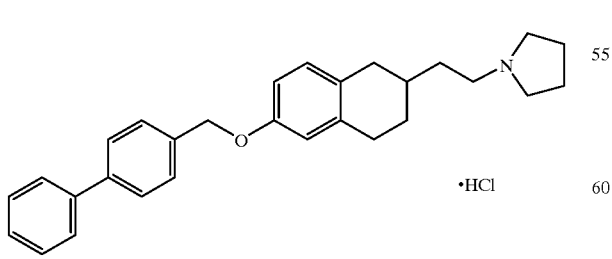

m.p.: 197–199° C.

Solvent for recrystallization: methanol-diisopropyl ether

EXAMPLE 40

6-(4-Biphenylyl)methoxy-2-(2-piperidinoethyl) tetralin hydrochloride

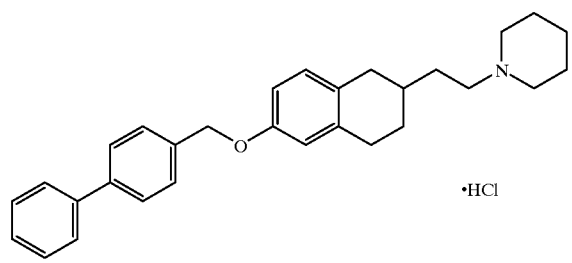

m.p.: 196–198° C.

Solvent for recrystallization: methanol-diisopropyl ether

EXAMPLE 41

6-(4-Biphenylyl)methoxy-2-[2-(4-piperidinopiperidino) ethyl]tetralin dihydrochloride

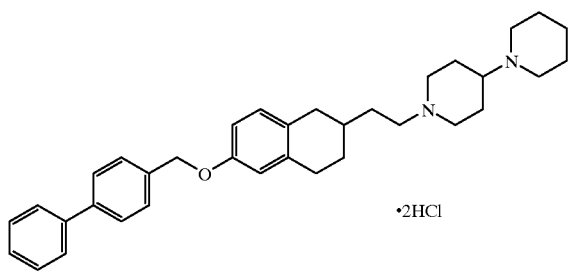

m.p.: 288–291° C.

Solvent for recrystallization: methanol-diisopropyl ether

EXAMPLE 42

6-(4-Biphenylyl)methoxy-2-[2-(4,4-dihydroxypiperidino) ethyl]tetralin hydrochloride

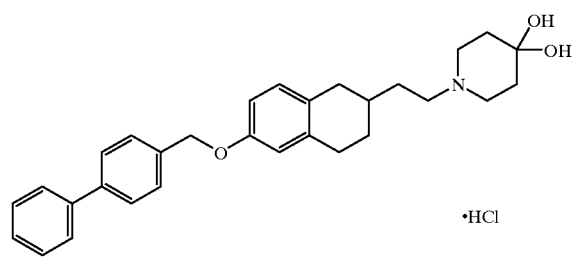

m.p.: 155–156° C.

Solvent for recrystallization: methanol-diisopropyl ether

EXAMPLE 43

6-(3'-Aminobiphenyl-4-yl)methoxy-2-[2-(N,N-dimethylamino) ethyl]tetralin hydrochloride

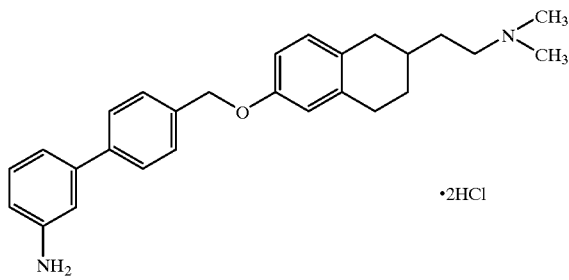

An ethanol solution (10 ml) of 3-aminophenylboric acid (1.3 g) and an aqueous 2M sodium carbonate solution (10 ml) were added to a toluene solution (80 ml) of 6-(4-bromobenzyl)oxy-2-[2-(N,N-dimethylamino) ethyl]tetralin (3.00 g) and tetrakis-(triphenylphosphine) palladium (0.45 g). The reaction mixture was heated under reflux for 12 hours in an argon atmosphere. A saturated aqueous sodium chloride solution was added to this, which was then extracted with ethyl acetate. The organic layer was dried, and then concentrated. The residue was purified by alumina column chromatography (eluent: ethyl acetate/hexane=1/2), and then processed with 4 N hydrochloric acid-ethyl acetate to form a hydrochloride. The thus-formed salt was recrystallized from methanol-diisopropyl ether to obtain the entitled compound (0.78 g).

m.p.: 205–206° C.

EXAMPLE 44

2-[2-(N,N-Dimethylamino)ethyl]-6-[(4'-methoxybiphenyl-4-yl) methoxy]tetralin hydrochloride

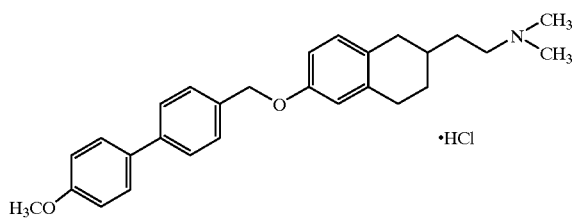

The entitled compound was obtained in the same manner as in Example 43.

m.p.: 182–185° C.

Solvent for recrystallization: methanol-diisopropyl ether

EXAMPLE 45

6-(4-Biphenylyl)methoxy-2-[3-(N,N-dimethylamino) propyl]tetralin hydrochloride

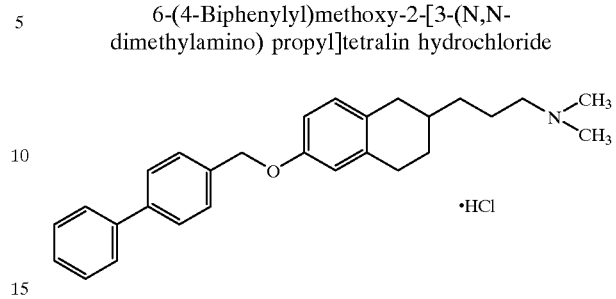

60% Oily sodium hydride (0.258 g) was added to a DMF solution (20 ml) of 2-[3-(N,N-dimethylamino) propyl]-6-hydroxytetralin (1.00 g) at 0° C. The reaction mixture was warmed to room temperature, and stirred for 30 minutes. This was again cooled to 0° C., and 4-(chloromethyl) biphenyl (1.04 g) as added thereto, and then stirred at room temperature for 4 hours. Water was added to the reaction mixture, which was then extracted with ethyl acetate. The organic layer was washed with water and a saturated aqueous sodium chloride solution, then dried, and concentrated. The residue was purified by alumina column chromatography (eluent: toluene alone to toluene/ethyl acetate=1/1), and then processed with 4 N hydrochloric acid-ethyl acetate to form a hydrochloride. The thus-formed salt was recrystallized from methanol-diisopropyl ether to obtain the entitled compound (1.30 g).

m.p.: 161–163° C.

EXAMPLE 46

6-(4-Biphenylyl)methoxy-2-[4-(N,N-dimethylamino) butyl]tetralin hydrochloride

The entitled compound was obtained in the same manner as in Example 45.

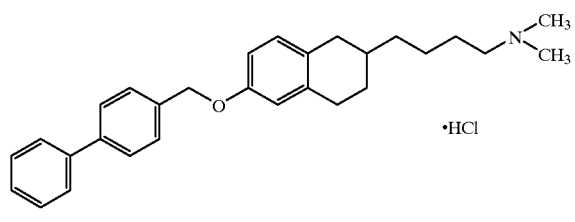

m.p.: 175–177° C.

Solvent for recrystallization: methanol-diisopropyl ether

EXAMPLE 47

(+)-6-(4-Biphenylyl)methoxy-2-[2-(N,N-dimethylamino) ethyl]tetralin hydrochloride (+)

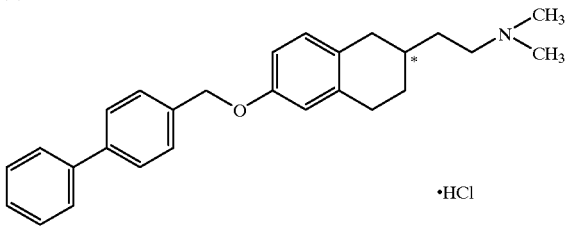

·HCl (+)-2-[2-(N,N-dimethylamino)ethyl]-6-hydroxytetralin hydrochloride (0.424 g) was converted into its free form, and then dissolved in DMF (10 ml), to which was added 60% oily sodium hydroxide (0.106 mg) at room temperature, and stirred for 45 minutes. The reaction mixture was heated up to 50° C., and stirred for 45 minutes. This was then cooled to 0° C., to which was added a DMF solution (5 ml) of 4-(chloromethyl)biphenyl (0.367 g), and stirred at room temperature for 2 hours. Water was added to the reaction mixture, which was then extracted with ethyl acetate. The organic layer was washed with water and a saturated aqueous sodium chloride solution, then dried, and concentrated. The residue was purified by alumina column chromatography (eluent: ethyl acetate/hexane=1/10 to 1/4), and then processed with 4 N hydrochloric acid-ethyl acetate to form a hydrochloride. The thus-formed salt was recrystallized from methanol-diisopropyl ether to obtain the entitled compound (0.484 g).

m.p.: 220–226° C. (decomposed).

$[\alpha]_D^{20}$=+46.0° (c=0.54, methanol) Optical purity: not lower than 99% e.e.

EXAMPLE 48

(−)-6-(4-Biphenylyl)methoxy-2-[2-(N,N-dimethylamino) ethyl]tetralin hydrochloride (−)

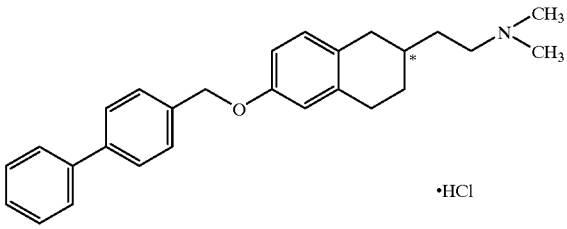

·HCl (−)-2-(N,N-dimethylamino)ethyl-6-hydroxytetralin hydrochloride (0.437 g) was converted into its free form, and then dissolved in DMF (10 ml), to which was added 60% oily sodium hydroxide (0.122 mg) at room temperature. The reaction mixture was heated up to 50° C., and stirred for 1 hour. This was then cooled to 0° C., to which was added a DMF solution (5 ml) of 4-(chloromethyl) biphenyl (0.344 g), and stirred at room temperature for 2 hours. Water was added to the reaction mixture, which was then extracted with ethyl acetate. The organic layer was washed with water and a saturated aqueous sodium chloride solution, then dried, and concentrated. The residue was purified by alumina column chromatography (eluent: ethyl acetate/hexane=1/10 to 1/4), and then processed with 4 N hydrochloric acid-ethyl acetate to form a hydrochloride. The thus-formed salt was recrystallized from methanol-diisopropyl ether to obtain the entitled compound (0.471 g).

m.p.: 219–225° C. (decomposed).

$[\alpha]_D^{20}$=−45.2° (c=0.52, methanol) Optical purity: not lower than 99% e.e.

EXAMPLE 49

(+)-6-(4-Biphenylyl)methoxy-2-[2-(N,N-dimethylamino) ethyl]tetralin hydrochloride monohydrate (+)

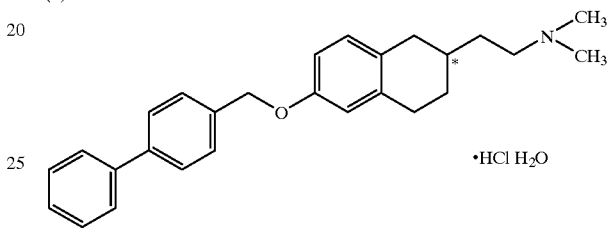

·HCl H₂O (+)-6-(4-Biphenylyl)methoxy-2-[2-(N,N-dimethylamino) ethyl]tetralin hydrochloride (150 g) was recrystallized from ethanol (2000 ml)-water (60 ml) to obtain the titled compound (127 g).

m.p.: 215–217° C. (decomposed).

$[\alpha]_D^{20}$=+42.4° (c=1.00 in methanol).

EXAMPLE 50

(+)-6-(4-Biphenylyl)methoxy-2-[2-(N,N-dimethylamino) ethyl]tetralin (+)

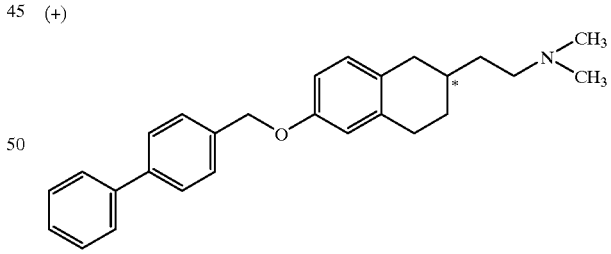

(+)-6-(4-Biphenylyl)methoxy-2-[2-(N,N-dimethylamino) ethyl]tetralin hydrochloride (4.50 g) was partitioned between ethyl acetate and 10% aqueous potassium carbonate and extracted. The organic layer was washed with saturated aqueous sodium chloride, dried, and concentrated. The residue was recrystallized from ethanol to obtain the titled compound (3.60 g).

m.p.: 83.5–84.5° C.

$[\alpha]_D^{20}$=+51.7° (c=1.00 in methanol).

EXAMPLE 51

(−)-6-(4-Biphenylyl)methoxy-2-[2-(N,N-dimethylamino) ethyl]tetralin

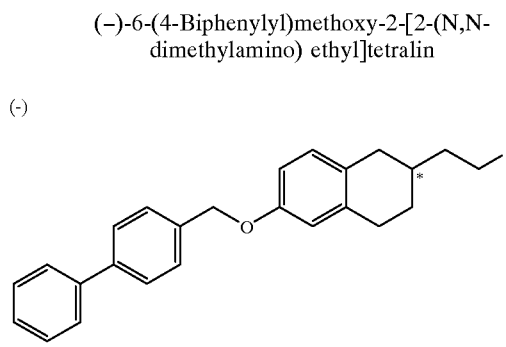

(−)-6-(4-Biphenylyl)methoxy-2-[2-(N,N-dimethylamino) ethyl]tetralin hydrochloride (3.00 g) was partitioned between ethyl acetate and 10% aqueous potassium carbonate and extracted. The organic layer was washed with saturated aqueous sodium chloride, dried, and concentrated. The residue was recrystallized from ethanol to obtain the titled compound (2.20 g).

m.p.: 84.2–85.2° C.

$[\alpha]_D^{20}$=−50.1° (c=0.50 in methanol).

EXAMPLE 52

(−)-6-(4-Biphenylyl)methoxy-2-[2-(N,N-dimethylamino) ethyl]tetralin fumarate

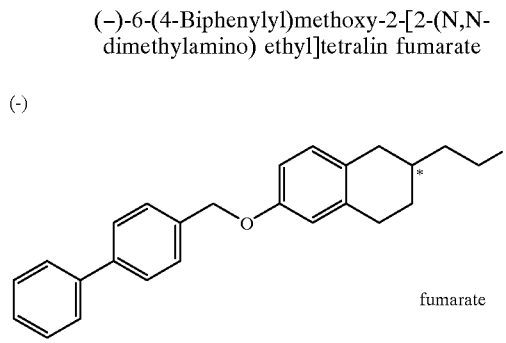

To a solution of (−)-6-(4-biphenylyl)methoxy-2-[2-(N,N-dimethylamino) ethyl]tetralin (1.3 g) in methanol (10 ml) was added a solution of fumaric acid (0.39 g) in methanol (10 ml) and concentrated. The resulting salt was recrystallized from methanol to obtain the titled compound (0.7 g).

m.p.: 212–213° C. (decomposed).

$[\alpha]_D^{20}$=−40.4° (c=0.5 in methanol).

EXAMPLE 53

(−)-6-(4-Biphenylyl)methoxy-2-[2-(N,N-dimethylamino) ethyl]tetralin citrate

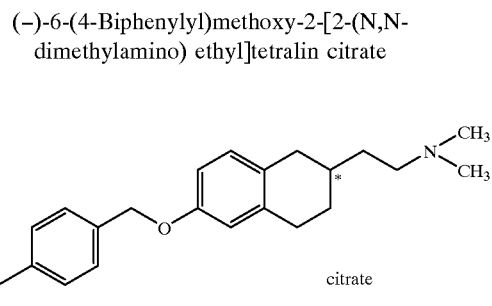

To a solution of (−)-6-(4-biphenylyl)methoxy-2-[2-(N,N-dimethylamino) ethyl]tetralin (1.3 g) in methanol (10 ml) was added a solution of citric acid (0.65 g) in methanol (10 ml) and the resulting precipitated salt was collected by filtration and washed with methanol, ethyl acetate, and diethyl ether to obtain the titled compound (1.9 g).

m.p.: 185–186° C. (decomposed).

EXAMPLE 54

(+)-2-[2-(N,N-Dimethylamino)ethyl]-6-(4'-methoxybiphenyl-4-yl) methoxytetralin hydrochloride

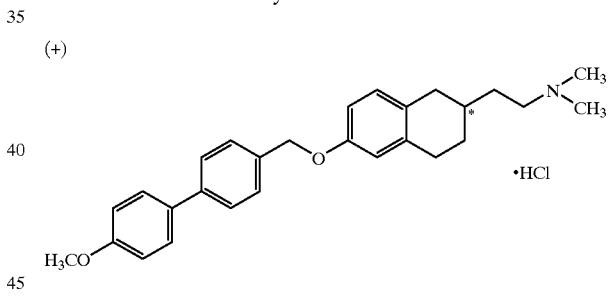

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 4-Methoxybenzeneboric acid (465 mg) and tetrakis (triphenylphosphine) palladium (82 mg) were added and the reaction mixture was heated under reflux for 14 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate: hexane=1:50 to 1:4) and converted into its hydrochloride, which was then recrystallized from methanol-diisopropyl ether to obtain the titled compound (870 mg).

m.p.: 230–232° C. (decomposed).

$[\alpha]_D^{20}$=+39.2° (c=1.00 in methanol).

EXAMPLE 55

(+)-2-[2-(N,N-Dimethylamino)ethyl]-6-(4'-methylbiphenyl-4-yl) methoxytetralin hydrochloride

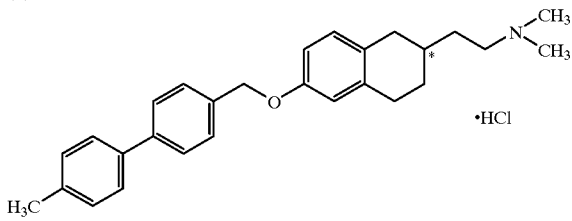

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 4-Methylbenzeneboric acid (416 mg) and tetrakis (triphenylphosphine) palladium (82 mg) were added and the reaction mixture was heated under reflux for 5 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate:hexane=1:40 to 1:4) and converted into its hydrochloride, which was then recrystallized from methanol-diisopropyl ether to obtain the titled compound (660 mg).

m.p.: 225–227° C. (decomposed).

$[\alpha]_D^{20}=+44.0°$ (c=1.00 in methanol).

EXAMPLE 56

(+)-6-(3'-Aminobiphenyl-4-yl)methoxy-2-[2-(N,N-dimethylamino) ethyl]tetralin dihydrochloride

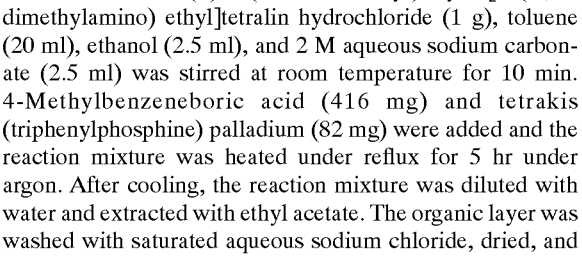

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 3-Aminobenzeneboric acid (474 mg) and tetrakis (triphenylphosphine) palladium (82 mg) were added and the reaction mixture was heated under reflux for 14 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate hexane=1:20 to 1:2) and converted into its dihydrochloride, which was then recrystallized from methanol-diisopropyl ether to obtain the titled compound (830 mg).

m.p.: 210–211° C. (decomposed).

$[\alpha]_D^{20}=+38.3°$ (c=1.00 in methanol).

EXAMPLE 57

(+)-2-[2-(N,N-Dimethylamino)ethyl]-6-(3'-formylbiphenyl-4-yl) methoxytetralin hydrochloride

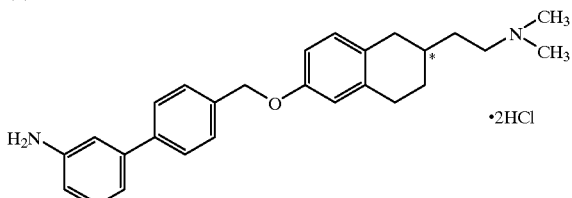

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 3-Formylbenzeneboric acid (460 mg) and tetrakis (triphenylphosphine) palladium (82 mg) were added and the reaction mixture was heated under reflux for 14 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate: hexane=1:20 to 1:2) and converted into its hydrochloride, which was then recrystallized from methanol-diisopropyl ether to obtain the titled compound (590 mg).

m.p.: 194–196° C. (decomposed).

$[\alpha]_D^{20}=+44.0°$ (c=1.00 in methanol).

EXAMPLE 58

(+)-6-(3'-Acetamidobiphenyl-4-yl)methoxy-2-[2-(N,N-dimethylamino) ethyl]tetralin hydrochloride

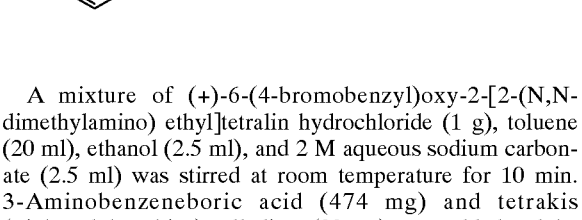

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 3-Acetamidobenzeneboric acid (559 mg) and tetrakis (triphenylphosphine) palladium (82 mg) were added and the reaction mixture was heated under reflux for 6 hr under argon. After cooling, the reaction mixture was diluted with water and extracted with ethyl acetate. The organic layer was washed with saturated aqueous sodium chloride, dried, and concentrated. The resultant crude crystals were washed with ethyl acetate and diisopropyl ether, purified by alumina column chromatography (eluent: ethyl acetate) and converted into its hydrochloride, which was then recrystallized from methanol-diisopropyl ether to obtain the titled compound (610 mg).

m.p.: 198–200° C. (decomposed).
$[\alpha]_D^{20}$=+41.0° (c=0.50 in methanol).

EXAMPLE 59

(+)-6-(2',4'-Dimethoxybiphenyl-4-yl)methoxy-2-[2-(N,N-dimethylamino) ethyl]tetralin hydrochloride (+)

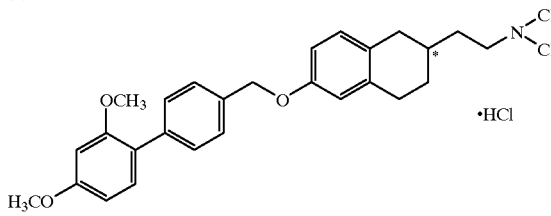

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 2.4-Dimethoxybenzeneboric acid (557 mg) and tetrakis (triphenylphosphine) palladium (82 mg) were added and the reaction mixture was heated under reflux for 14 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate: hexane=1:20 to 1:5) and converted into its hydrochloride, which was then recrystallized from methanol-diisopropyl ether to obtain the titled compound (740 mg).

m.p.: 159–161° C.
$[\alpha]_D^{20}$=+42.2° (c=0.50 in methanol).

EXAMPLE 60

(+)-6-(3',4'-Dimethoxybiphenyl-4-yl)methoxy-2-[2-(N,N-dimethylamino) ethyl]tetralin hydrochloride (+)

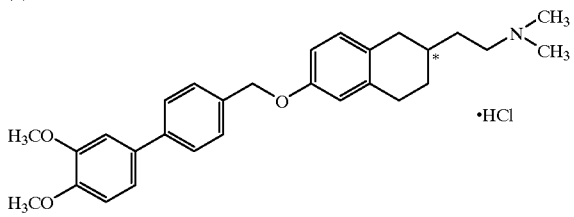

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 3.4-Dimethoxybenzeneboric acid (557 mg) and tetrakis (triphenylphosphine) palladium (82 mg) were added and the reaction mixture was heated under reflux for 5 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate: hexane=1:20 to 1:5) and converted into its hydrochloride, which was then recrystallized from methanol-diisopropyl ether to obtain the titled compound (840 mg).

m.p.: 228–230° C. (decomposed).
$[\alpha]_D^{20}$=+42.2° (c=0.50 in methanol).

EXAMPLE 61

(+)-6-[4-(1,3-Benzodioxol-5-yl)phenyl]methoxy-2-[2-(N,N-dimethylamino) ethyl]tetralin hydrochloride (+)

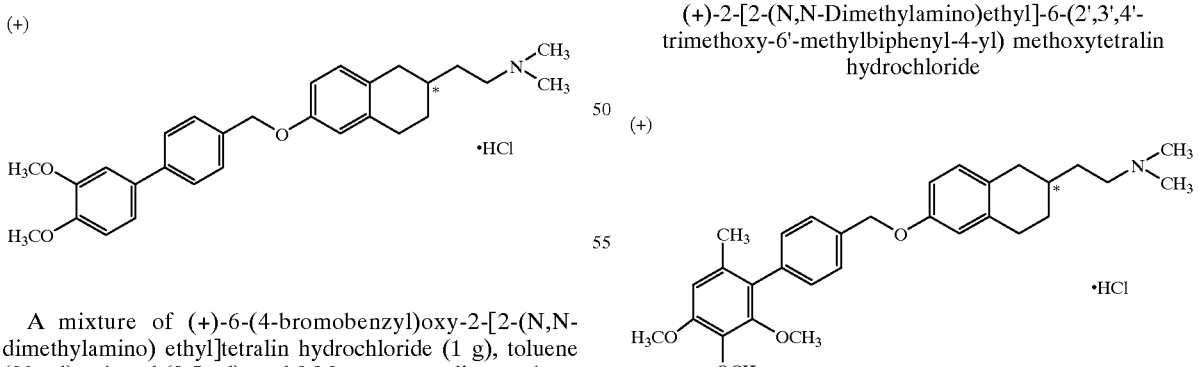

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 3,4-Methylenedioxybenzeneboric acid (469 mg) and tetrakis(triphenylphosphine) palladium (82 mg) were added and the reaction mixture was heated under reflux for 14 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate hexane= 1:20 to 1:5) and converted into its hydrochloride, which was then recrystallized from methanol-diisopropyl ether to obtain the titled compound (830 mg).

m.p.: 222–224° C. (decomposed).
$[\alpha]_D^{20}$=+39.9° (c=0.40 in methanol).

EXAMPLE 62

(+)-2-[2-(N,N-Dimethylamino)ethyl]-6-(2',3',4'-trimethoxy-6'-methylbiphenyl-4-yl) methoxytetralin hydrochloride (+)

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. To the reaction mixture were added 2,3,4-trimethoxy-6- methylbenzeneboric acid (692 mg) and tetrakis(triphenylphosphine) palladium (82 mg) and the reaction mixture was heated under reflux for 14 hr under argon. After cooling, the reaction mixture was diluted with water and extracted with ethyl acetate. The organic layer was washed with saturated aqueous sodium chloride, dried, and concentrated. The residue was purified by alumina column chromatography (eluent:ethyl acetate: hexane=1:20 to 1:6) and converted into its hydrochloride, which was recrystallized from methanol-diisopropyl ether to obtain the titled compound (950 mg).

m.p.: 222–224° C. (decomposed).

$[\alpha]_D^{20}$=+37.7° (c=0.50 in methanol).

EXAMPLE 63

(+)-6-[4-(2-Benzofuranyl)phenyl]methoxy-2-[2-(N,N-dimethylamino) ethyl]tetralin hydrochloride

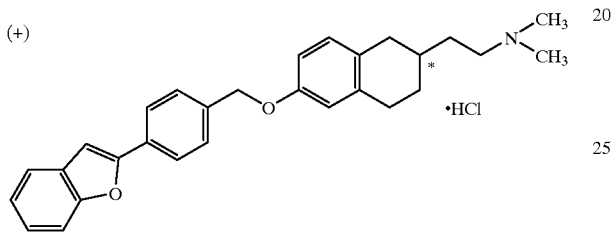

A mixture of (+)-6-(4-bromobenzyl)oxy-2-[2-(N,N-dimethylamino) ethyl]tetralin hydrochloride (1 g), toluene (20 ml), ethanol (2.5 ml) and 2 M aqueous sodium carbonate (2.5 ml) was stirred at room temperature for 10 mi. 2-Benzofuranboric acid (496 mg) and tetrakis(triphenylphosphine) palladium (82 mg) were added and the reaction mixture was heated under reflux for 6 hr under argon. After cooling, the reaction mixture was diluted with water and extracted with ethyl acetate. The organic layer was washed with saturated aqueous sodium chloride, dried, and concentrated. The crude crystals were washed with diisopropyl ether and further purified by alumina column chromatography (eluent: ethyl acetate) and converted into its hydrochloride, which was then recrystallized from methanol-diisopropyl ether to obtain the titled compound (730 mg).

m.p.: 235–237° C. (decomposed).

$[\alpha]_D^{20}$=+42.2° (c=0.40 in methanol).

EXAMPLE 64

(+)-2-[2-(N,N-Dimethylamino)ethyl]-6-[4-(2-naphthyl) phenyl]methoxytetralin hydrochloride

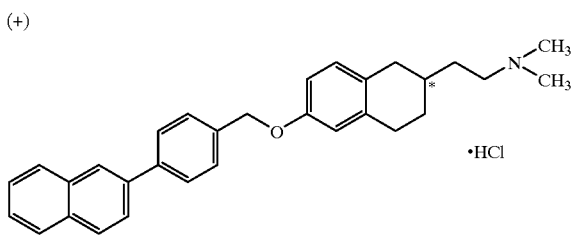

A mixture of (+)-6-(4-bromobenzyl)oxy-2-[2-(N,N-dimethylamino) ethyl]tetralin hydrochloride (1 g), toluene (20 ml), ethanol (2.5 ml), and 2 M aqueous sodium carbonate (2.5 ml) was stirred at room temperature for 10 min. 2-Naphthaleneboric acid (526 mg) and tetrakis(triphenylphosphine) palladium (82 mg) were added and the reaction mixture was heated under reflux for 14 hr under argon. After cooling, the reaction mixture was diluted with water and extracted with ethyl acetate. The organic layer was washed with saturated aqueous sodium chloride, dried, and concentrated. The residue was purified by alumina column chromatography (eluent: ethyl acetate: hexane=1:20 to 1:7) and converted into its hydrochloride, which was then recrystallized from methanol-diisopropyl ether to obtain the titled compound (850 mg).

m.p.: 233–235° C. (decomposed).

$[\alpha]_D^{20}$=+40.6° (c=0.40 in methanol).

EXAMPLE 65

2-[2-(N,N-Dimethylamino)ethyl]-6-[(4'-methylbiphenyl-4-yl) methoxy]tetralin hydrochloride

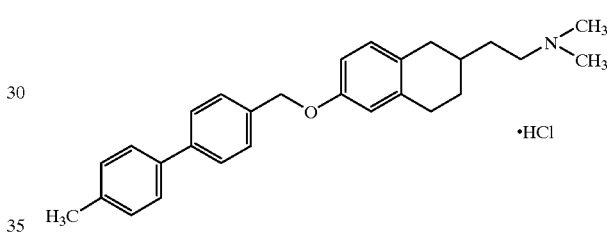

The titled compound was synthesized by the similar manner as in Example 43.

m.p.: 208–209° C. Recrystallizing solvent: ethanol.

EXAMPLE 66

6-(4-Biphenylyl)methoxy-2-[2-(3-ethoxycarbonylpiperidino) ethyl]tetralin

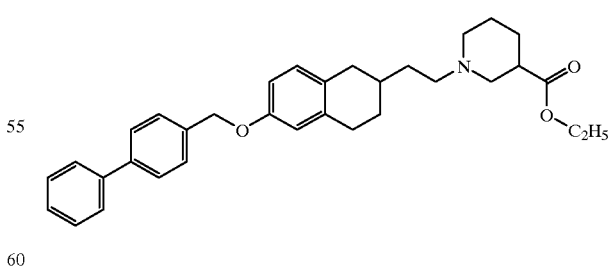

The titled compound was synthesized by the similar manner as in Example 38.

m.p.: 97–98° C. Recrystallizing solvent: ethyl acetate-hexane.

EXAMPLE 67

6-(4-Biphenylyl)methoxy-2-[(3-aza-4-ethoxycarbonyl-3-methyl) butyl]tetralin hydrochloride

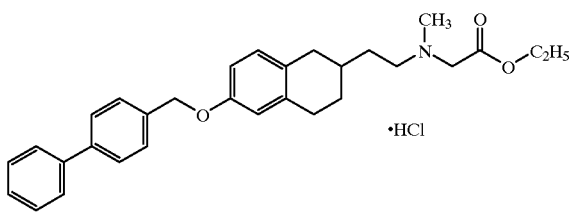

The titled compound was synthesized by the similar manner as in Example 38.

m.p.: 126–128° C. Recrystallizing solvent: ethanol.

EXAMPLE 68

6-(4-Biphenylyl)-2-(2-aminoethyl)tetralin hydrochloride

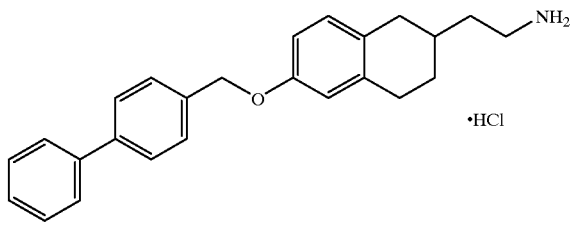

To a solution of 6-(4-biphenylyl)methoxy-2-(2-iodoethyl)tetralin (0.4 g) in DMF (10 ml) was added potasium phthalimide (0.4 g) and stirring was continued at room temperature for 2 days. The reaction mixture was diluted with water and the precipitate was collected by filtration. The precipitate was dissolved in ethanol (40 ml) and hydrazine monohydrate (5 ml) was added to the solution. After stirring at 50° C. for 3 hr, the reaction mixture was concentrated. The residue was dissolved in ethyl acetate, which was washed with water, dried, and concentrated. The residue was dissolved in ethanol (20 ml) and 4 N hydrochloric acid/ethyl acetate (2 ml) was added and the solvent was removed by concentration. The residue was recrystallized from methanol-ethyl acetate to obtain the titled compound (0.37 g).

m.p.: 262–265° C.

EXAMPLE 69

2-(N,N-Dimethylamino)methyl-6-(2-quinolyl) methoxytetralin dihydrochloride

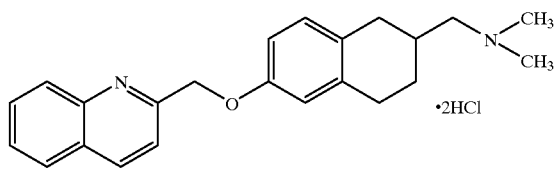

To a solution of 2-(N,N-dimethylamino)methyl-6-hydroxytetralin (153 mg, a free form of Reference Example 16) and 2-chloromethylquinoline hydrochloride (189 mg) in DMF (5 ml) was added potassium carbonate (260 mg) and the reaction mixture was stirred at room temperature for 26 hr. The reaction mixture was diluted with water and extracted with ethyl acetate. The organic layer was washed with water and saturated aqueous sodium chloride, dried, and concentrated. The residue was purified by alumina column chromatography (eluent: ethyl acetate: hexane=1:2) and then converted into its dihydrochloride, which was further recrystallized from methanol-ethyl acetate to obtain the titled compound (191 mg).

m.p.: 187–190° C. (decomposed).

EXAMPLE 70

2-(N,N-Dimethylamino)methyl-6-(5-phenyl-1,3,4-oxadiazol-2-yl) methoxytetralin

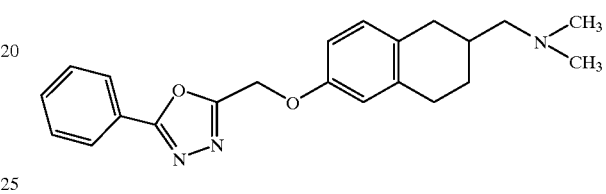

To a solution of 2-(N,N-dimethylamino)methyl-6-hydroxytetralin (206 mg, a free form of Reference Example 16) and 2-chloromethyl-5-phenyl-1,3,4-oxadiazole (231 mg) in DMF (5 ml) was added potassium carbonate (215 mg) and the reaction mixture was stirred at room temperature for 15 hr. The reaction mixture was diluted with water and extracted with ethyl acetate. The organic layer was washed with water and saturated aqueous sodium chloride, dried, and concentrated. The residue was purified by alumina column chromatography (eluent: ethyl acetate: hexane=1:2) to obtain the titled compound (307 mg).

$^1$H NMR δ: 1.22–1.49(1H,m), 1.84–2.03(2H,m), 2.07–2.44(3H,m), 2.24(6H,s), 2.74–2.96(3H,m), 5.28(2H,s), 6.74–6.95(2H,m), 7.03(1H,d), 7.44–7.60(3H,m), 8.02–8.11 (2H,m).

EXAMPLE 71

6-(5-Phenyl-1,3,4-oxadiazol-2-yl)methoxy-2-piperidinomethyltetralin hydrochloride

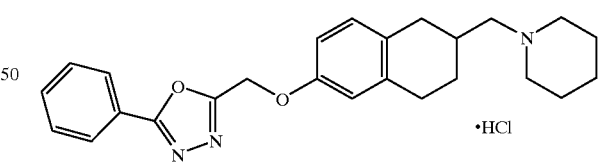

To a solution of 6-hydroxy-2-piperidinomethyltetralin (141 mg, free form of Reference Example 19) and 2-chloromethyl-5-phenyl-1,3,4-oxadiazole (148 mg) in DMF (3 ml) was added potassium carbonate (143 mg) and the reaction mixture was stirred at room temperature for 24 hr. The reaction mixture was diluted with water and extracted with ethyl acetate. The organic layer was washed with water and saturated aqueous sodium chloride, dried, and concentrated. The residue was purified by silica gel column chromatography (eluent: ethyl acetate: methanol= 10:1) and alumina column chromatography (eluent:ethyl acetate: hexane=1:4), and then converted into its hydrochloride, which was further recrystallized from methanol-diethyl ether to obtain the titled compound (175 mg).

m.p.: 217–219° C. (decomposed).

EXAMPLE 72

6-(2-Benzothiazolyl)methoxy-2-piperidinomethyltetralin hydrochloride

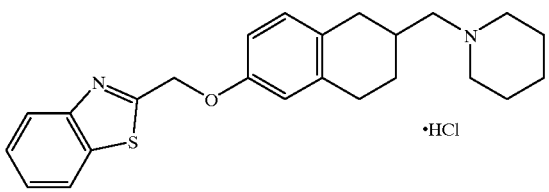

To a solution of 6-hydroxy-2-piperidinomethyltetralin hydrochloride (205 mg, Reference Example 19) and 2-chloromethylbenzothiazole (183 mg) in DMF (10 ml) was added potassium carbonate (327 mg) and the reaction mixture was stirred at room temperature for 4 days and further at 60° C. for 7 hr. The reaction mixture was diluted with water and extracted with ethyl acetate. The organic layer was washed with water and saturated aqueous sodium chloride, dried, and concentrated. The residue was purified by silica gel column chromatography (eluent: ethyl acetate: methanol=10:1), alumina column chromatography (eluent: ethyl acetate: hexane=1:4) and converted into its hydrochloride, which was recrystallized from methanol-ethyl acetate to obtain the titled compound (158 mg).

m.p.: 229–232° C.

EXAMPLE 73

6-(2'-Cyanobiphenyl-4-yl)methoxy-2-[2-(N,N-dimethylamino) ethyl]tetralin hydrochloride

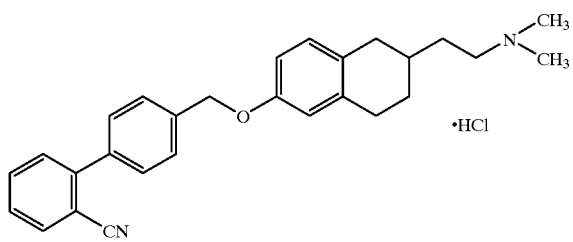

To a solution of 2-[2-(N,N-dimethylamino)ethyl]-6-hydroxytetralin (72 mg, Reference Example 20) and 4-bromomethyl-2'-cyanobiphenyl (106 mg) in DMF (3 ml) was added sodium hydride (60% in oil, 36 mg) at 0° C. and the reaction mixture was stirred at 0° C. for 40 min. The reaction mixture was diluted with water and extracted with ethyl acetate. The organic layer was washed with water and saturated aqueous sodium chloride, dried, and concentrated. The residue was purified by alumina column chromatography (eluent: ethyl acetate: hexane=1:4) and converted into its hydrochloride, which was further recrystallized from methanol-diisopropyl ether to obtain the titled compound (75 mg).

m.p.: 201–206° C.

EXAMPLE 74

6-(4-Biphenylyl)methoxy-2-[[[N-[2-(N,N-dimethylamino) ethyl]-N-methyl]amino]ethyl] tetralin dihydrochloride

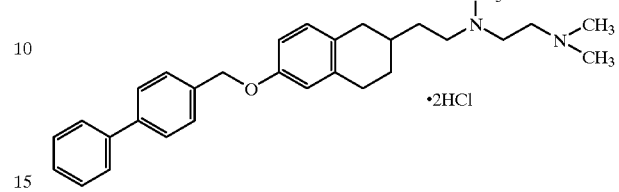

To a solution of [6-(4-biphenylyl)methoxy-2-tetralin]-N-[2-(N,N-dimethylamino) ethyl]-N-methylacetamide (495 mg) in THF (20 ml) was added lithium aluminum hydride (94 mg) at 0° C. The reaction mixture was stirred at room temperature for 50 min and heated under reflux for 2 hr. After cooling, the reaction mixture was poured into water and the precipitate was removed by filtration. The filtrate was concentrated and the residue was converted into its dihydrochloride, which was then recrystallized from methanol-ethyl acetate to obtain the titled compound (346 mg).

m.p.: 248–258° C. (decomposed).

EXAMPLE 75

6-(4-Biphenylyl)methoxy-2-[[[N-[2-(N,N-diethylamino) ethyl]-N-methyl]amino]ethyl]tetralin dihydrochloride

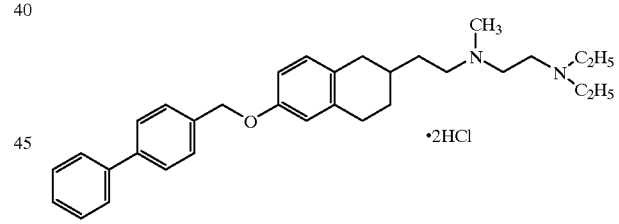

[6-(4-Biphenylyl)methoxy-2-tetralin]-N-[2-(N,N-diethylamino) ethyl]-N-methylacetamide hydrochloride (320 mg) was converted into its free form and dissolved in THF (20 ml). Lithium aluminum hydride (68 mg) was added to the solution at 0° C. After stirring at room temperature for 4.5 hr, the reaction mixture was heated under reflux for 30 min. After cooling, the reaction mixture was diluted with water and the precipitate was removed by filtration. The filtrate was concentrated. The residue was converted into its dihydrochloride, which was washed with ethyl acetate and diisopropyl ether and settled out from methanol-diisopropyl ether to obtain the titled compound (281 mg) as an amorphous powder.

IR(KBr): 3314, 2926, 2635, 1611, 1505, 1267, 1235, 1163, 1011, 774 cm$^{-1}$.

EXAMPLE 76

6-(4-Biphenylyl)methoxy-2-[2-(N-methylamino) ethyl]tetralin

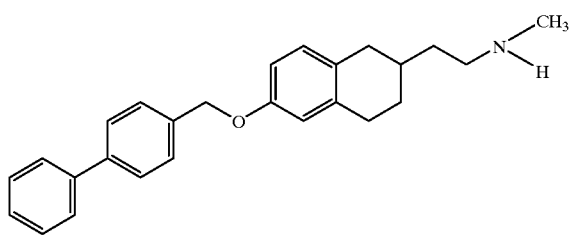

To a solution of [6-(4-biphenylyl)methoxy-2-tetralin]-N-methylacetamide (3.958 g) in THF (50 ml) was added 1M borane-THF complex (35 ml) at room temperature. The reaction mixture was heated under reflux for one hr. After cooling, the reaction mixture was diluted with water and 6 N aqueous hydrochloric acid (20 ml) at 0° C. and stirred at room temperature for 3 hr. The reaction mixture was made basic by adding 1 N aqueous sodium hydroxide and extracted with ethyl acetate. The organic layer was washed with water and saturated aqueous sodium chloride, dried, and concentrated. The residue was purified by alumina column chromatography (eluent: ethyl acetate: hexane=1:1) and then by recrystallization from ethyl acetate-hexane to obtain the titled compound (343 mg).

m.p.: 75–76° C.

EXAMPLE 77

6-(4-Biphenylyl)methoxy-2-[2-(N-methylamino) ethyl]tetralin hydrochloride

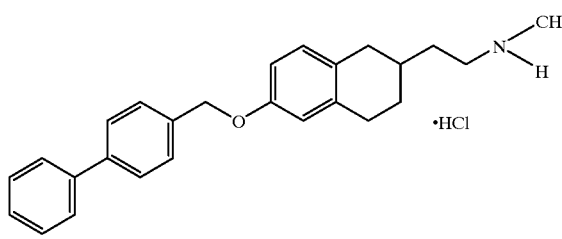

To a solution of [6-(4-biphenylyl)methoxy-2-tetralin]-N-methylacetamide (580 mg) in THF (15 ml) was added 1M borane-THF complex (5 ml) at room temperature. After stirring at room temperature for 2.5 hr, the reaction mixture was heated under ref lux for 2.5 hr and cooled. The reaction mixture was diluted with water and 6 N aqueous hydrochloric acid (10 ml) at 0° C. and stirred at room temperature for 8 hr. The reaction mixture was made basic by adding 1 N aqueous sodium hydroxide and extracted with ethyl acetate. The organic layer was washed with water and saturated aqueous sodium chloride, dried, and concentrated. The residue was purified by alumina column chromatography (eluent: ethyl acetate: hexane=1:1) and then converted into its hydrochloride, which was washed with ethyl acetate to obtain the titled compound (167 mg).

m.p.: 233–237° C. (decomposed).

EXAMPLE 78

6-(4-Biphenylyl)methoxy-2-[2-(N-ethylamino) ethyl]tetralin

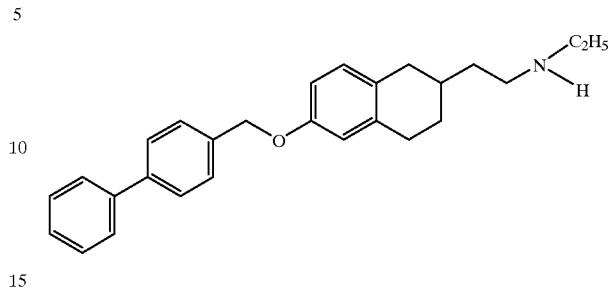

[6-(4-Biphenylyl)methoxy-2-tetralin]-N-ethylacetamide (4.009 g) was added to 1M borane-THF complex (20 ml) at room temperature. The reaction mixture was heated under reflux for 5 hr and cooled. Water and 6 N aqueous hydrochloric acid (10 ml) were added at 0° C. and the reaction mixture was stirred at room temperature for 63 hr. The reaction mixture was made basic by adding 1 N aqueous sodium hydroxide and extracted with ethyl acetate. The organic layer was washed with water and saturated aqueous sodium chloride, dried, and concentrated. The crude product was recrystallized from ethyl acetate-hexane to obtain the titled compound (2.851 g).

m.p.: 83–85° C.

EXAMPLE 79

6-(4-Biphenylyl)methoxy-2-[2-(N-ethylamino) ethyl]tetralin hydrochloride

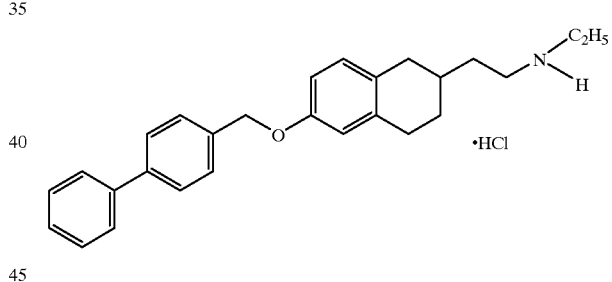

6-(4-Biphenylyl)methoxy-2-[2-(N-ethylamino) ethyl]tetralin (1.009 g) was converted into its hydrochloride. The hydrochloride was washed with methanol, ethyl acetate, and diethyl ether to obtain the titled compound (810 mg).

m.p.: 244–249° C. (decomposed).

EXAMPLE 80

2-(4-Benzylpiperazin-1-yl)methyl-6-(2-naphthyl) methoxytetralin dihydrochloride

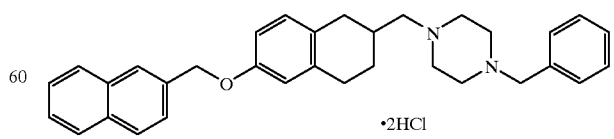

To a solution of 2-(4-benzylpiperazin-1-yl)methyl-6-hydroxytetralin (250 mg) in DMF (20 ml) was added sodium hydride (60% in oil, 30 mg) and the solution was stirred at room temperature for 30 min. A solution of 2-naphthylmethylbromide (162 mg) in DMF (10 ml) was added and the reaction mixture was stirred at room temperature for one hr, diluted with water, and extracted with ethyl acetate. The organic layer was washed with saturated aqueous sodium chloride, dried, and concentrated. The residue was purified by silica gel column chromatography (eluent: ethyl acetate:hexane=1:1) and converted into its dihydrochloride, which was then recrystallized from methanol-ethyl acetate to obtain the titled compound (240 mg).

m.p.: 210–212° C.

EXAMPLE 81

7-(4-Biphenylyl)methoxy-3-(N,N-dimethylamino) methyl-1,2,3,4-tetrahydroquinoline hydrochloride

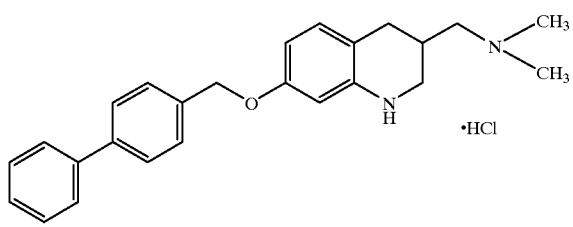

To a solution of 3-(dimethylamino)methyl-1,2,3,4-tetrahydro-7-quinolinol (344 mg), 4-biphenylylmethanol (368 mg), and triphenylphosphine (525 mg) in THF (20 ml) was added diethyl azodicarboxylate (348 mg). After stirring at room temperature for one hr, the reaction mixture was poured into 1 N aqueous hydrochloric acid and washed with ethyl acetate. The water layer was neutralized by 1 N aqueous sodium hydroxide, diluted with saturated aqueous sodium bicarbonate, and extracted with ethyl acetate. The organic layer was washed with saturated aqueous sodium chloride, dried, and concentrated. The residue was purified by alumina column chromatography (eluent: ethyl acetate: hexane=1:4) and converted into its hydrochloride, which was further recrystallized from ethanol-diisopropyl ether to obtain the titled compound (214 mg).

m.p.: 183–184° C.

EXAMPLE 82

(+)-6-(4-Biphenylyl)methoxy-2-[2-(N,N-diethylamino) ethyl]tetralin hydrochloride

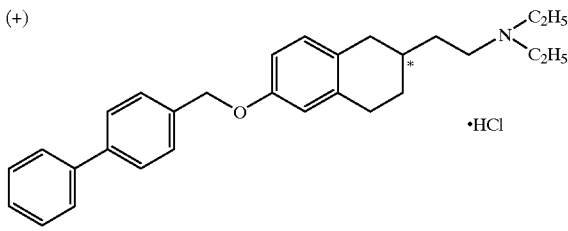

To a solution of (+)-2-[2-(N,N-diethylamino) ethyl]-6-hydroxytetralin (4.5 g) in DMF (60 ml) was added sodium hydride (60% in oil, 1.46 g) at 0° C. The reaction mixture was stirred at room temperature for 30 min and a solution of 4-chloromethylbiphenyl (4.08 g) in DMF (40 ml) was added. After stirring at room temperature for 2 hr, the reaction mixture was poured into water, neutralized with 1 N aqueous hydrochloric acid. Saturated aqueous sodium bicarbonate (50 ml) was added and the reaction mixture was extracted with combined solvent of ethyl acetate and THF (1:1). The organic layer was dried and concentrated. The residue was purified by silica gel column chromatography (eluent: ethyl acetate to ethyl acetate: triethylamine=4:1) and converted into its hydrochloride, which was recrystallized from ethanol-diisopropyl ether to obtain the titled compound (6 g).

m.p.: 151–153° C.

$[\alpha]_D^{20}$=+42.1° (c=0.504 in methanol). Optical purity: 97.6% e.e. (by HPLC analysis).

EXAMPLE 83

(−)-6-(4-Biphenylyl)methoxy-2-[2-(N,N-diethylamino) ethyl]tetralin hydrochloride

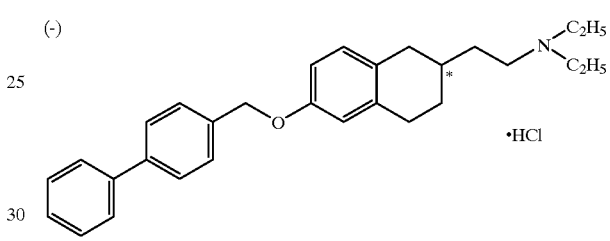

The titled compound was synthesized by the similar manner as in Example 82.

Recrystallizing solvent; ethanol-diisopropyl ether m.p.: 151–153° C.

$[\alpha]_D^{20}$=−40.6° (c=0.500 in methanol). Optical purity: 98.9% e.e. (by HPLC analysis)

EXAMPLE 84

6-(4-Biphenylyl)methoxy-2-[2-(N,N-dimethylamino) ethyl]-3,4-dihydronaphthalene hydrochloride

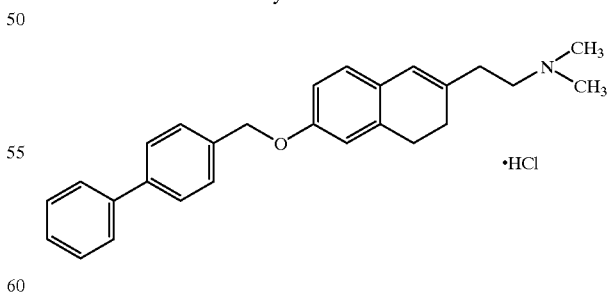

6-(4-Biphenylyl)methoxy-2-[2-(N-dimethylamino) ethyl]-3,4-dihydronaphthalene (44 mg) was converted into its hydrochloride, which was crystallized from methanol-diisopropyl ether to obtain the titled compound (43 mg).

m.p.: 233–243° C. (decomposed).

EXAMPLE 85

7-(4-Biphenylyl)methoxy-3-[2-(N,N-dimethylamino) ethyl]-1,2,3,4-tetrahydroquinoline dihydrochloride

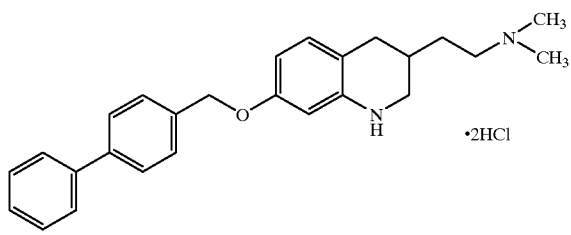

[7-(4-Biphenylyl)methoxy-1,2,3,4-tetrahydro-2-oxo-3-quinoline]-N,N-dimethylacetamide (1.407 g) was added to 1M borane-THF complex (15 ml) at room temperature. After stirring at room temperature for 15 hr and cooled. The reaction mixture was diluted with water and extracted with ethyl acetate. The organic layer was washed with saturated aqueous sodium chloride, dried, and concentrated. The residue was dissolved in THF (50 ml) and methanol (20 ml) and 1 N aqueous sodium hydroxide (20 ml) was added to the solution. The reaction mixture was heated under reflux for 5 days and cooled. The reaction mixture was diluted with water and extracted with ethyl acetate. The organic layer was washed with water and saturated aqueous sodium chloride, dried, and concentrated. The residue was purified by alumina column chromatography (eluent:ethyl acetate:hexane=1:4) and converted into its dihydrochloride, which was recrystallized from ethanol to obtain the titled compound (647 mg).

m.p.: 185–192° C. (decomposed).

EXAMPLE 86

1-Acetyl-7-(4-biphenylyl)methoxy-3-[2-(N,N-dimethylamino) ethyl]-1,2,3,4-tetrahydroquinoline

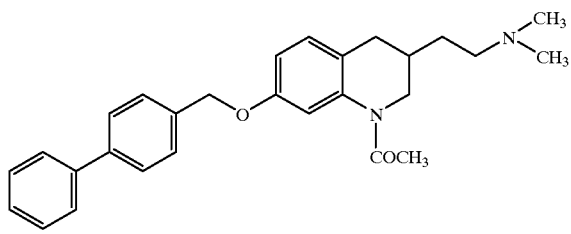

To a solution of 7-(4-biphenylyl)methoxy-3-[2-(N,N-dimethylamino) ethyl]-1,2,3,4-tetrahydroquinoline (250 mg) in THF (17 ml) was added triethylamine (0.33 ml) followed by addition of acetyl chloride (0.09 ml) at 0° C. After stirring in an ice bath for one hr, the reaction mixture was further stirred at room temperature for one hr. The reaction mixture was diluted with water and extracted with ethyl acetate. oil The organic layer was washed with saturated aqueous sodium chloride, dried, and concentrated. The residue was purified by alumina column chromatography (eluent:ethyl acetate: hexane=1:20 to 1:6) and the resulting precipitated crystals were washed with diisopropyl ether to obtain the titled compound (210 mg).

m.p.: 62.0–63.5° C.

EXAMPLE 87

7-(4-Biphenylyl)methoxy-3-[2-(N,N-dimethylamino) ethyl]-1-ethyl-1,2,3,4-tetrahydroquinoline dihydrochloride

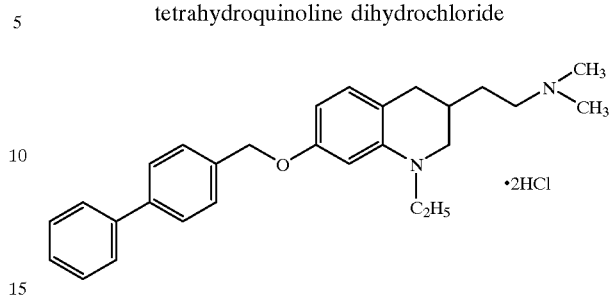

To a solution of 1-acetyl-7-(4-biphenylyl)methoxy-3-[2-(N,N-dimethylamino)ethyl]-1,2,3,4-tetrahydroquinoline (120 mg) in THF (1.5 ml) was added 1M borane-THF complex (0.9 ml) in an ice bath. After stirring at room temperature for 15 min, The reaction mixture was heated under reflux for 15 min and cooled. A small portion of water was added, followed by addition of 12 N aqueous sodium hydroxide (1.5 ml) and the reaction mixture was heated under reflux for 16 hr and cooled. The reaction mixture was diluted with water and extracted with diethyl ether. The organic layer was washed with saturated aqueous sodium chloride, dried, and concentrated. The residue was purified by alumina column chromatography (eluent: ethyl acetate:hexane=1:20 to 1:7) and converted into its dihydrochloride, which was recrystallized from methanol-diisopropyl ether to obtain the titled compound (101 mg).

m.p.: 173–175° C. (decomposed).

EXAMPLE 88

(+)-2-[2-(N,N-Dimethylamino)ethyl]-6-(6-phenyl-3-pyridyl) methoxytetralin dihydrochloride (+)

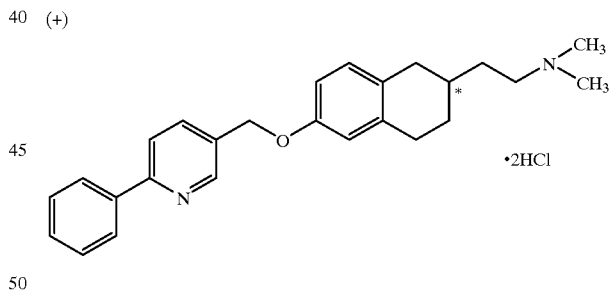

To a solution of (+)-2-[2-(N,N-dimethylamino) ethyl]-6-hydroxytetralin (0.221 g) in DMF (5 ml) was added sodium hydride (60% in oil, 0.053 g) at room temperature. After stirring at 50° C. for one hr, the reaction mixture was cooled to 0° C. and a solution of 6-phenyl-3-pyridylmethyl bromide (76%, 0.366 g) in THF (5 ml) was added. The reaction mixture was stirred at 0° C. for one hr, diluted with water, and extracted with ethyl acetate. The organic layer was washed with water and saturated aqueous sodium chloride, dried, and concentrated. The residue was purified by alumina column chromatography (eluent: ethyl acetate: hexane=1:4) and converted into its dihydrochloride, which was recrystallized from ethanol-ethyl acetate to obtain the titled compound (265 mg).

m.p.: 218–220° C.

$[\alpha]_D^{20}$=+43.5° (c=0.504 in methanol).

EXAMPLE 89

(+)-2-[2-(N,N-Dimethylamino)ethyl]-6-[6-(methoxyphenyl)-3-pyridyl]methoxytetralin dihydrochloride

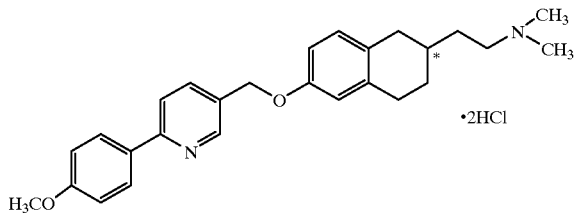

A mixture of (+)-6-(2-bromopyridin-5-yl)methoxy-2-[2-(N,N-dimethylamino)ethyl]tetralin dihydrochloride (0.2 g), toluene (8 ml), ethanol (1 ml), 2M aqueous sodium carbonate (1 ml) was stirred at room temperature for 10 min. 4-methoxyphenylboric acid (89 mg), and tetrakis (triphenylphosphine)palladium (27 mg) was added and the reaction mixture was heated under reflux under argon for 15 hr and cooled. The reaction mixture was diluted with water and extracted with ethyl acetate. The organic layer was washed with water and saturated aqueous sodium chloride, dried, and concentrated. The residue was purified by alumina column chromatography (eluent: ethyl acetate:hexane=1:4) and then converted into its dihydrochloride, which was recrystallized from ethanol-ethyl acetate to obtain the titled compound (176 mg).

m.p.: 223–231° C. (decomposed).

$[\alpha]_D^{20}$=+41.1° (c=0.494 in methanol).

EXAMPLE 90

7-(4-Biphenylyl)methoxy-3-[2-(N,N-dimethylamino) ethyl]-1,2,3,4-tetrahydro-1-methylsulfonylquinoline hydrochloride

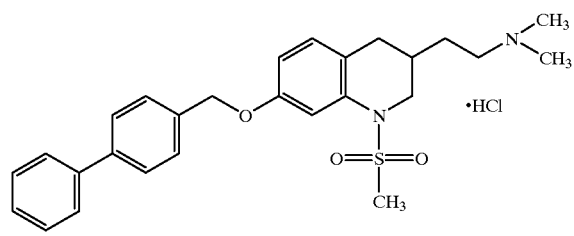

To a solution of 7-(4-biphenylyl)methoxy-3-[2-(N,N-dimethylamino) ethyl]-1,2,3,4-tetrahydroquinoline (110 mg) in pyridine (5 ml) was added methanesulfonyl chloride (0.03 ml) in an ice bath. The reaction mixture was stirred at room temperature for 3 hr. The reaction mixture was diluted with water and extracted with ethyl acetate. The organic layer was washed with saturated aqueous sodium chloride, dried, and concentrated. The residue was purified by alumina column chromatography (eluent: ethyl acetate:hexane=1:2) and converted into its hydrochloride, which was then recrystallized from ethanol-ethyl acetate to obtain the titled compound (88 mg).

m.p.: 236–240° C. (decomposed).

EXAMPLE 91

(+)-6-(2-Benzofuranyl)methoxy-2-[2-(N,N-dimethylamino) ethyl]tetralin

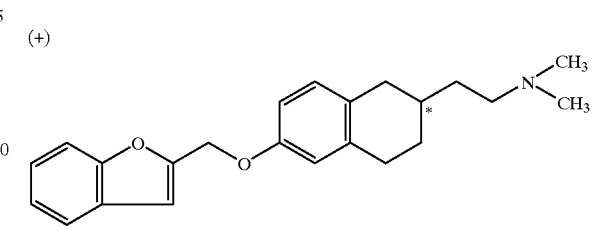

To a solution of (+)-2-[2-(N,N-dimethylamino) ethyl]-6-hydroxytetralin (0.217 g) in DMF (5 ml) was added sodium hydride (60% in oil, 0.052 g) at room temperature. The reaction mixture was stirred at 50° C. for one hr and cooled to 0° C. A solution of 2-chloromethylbenzofuran (0.187 g) in THF (5 ml) was added to the solution. The reaction mixture was stirred at 0° C. for one hr, diluted with water, and extracted with ethyl acetate. The organic layer was washed with water and saturated aqueous sodium chloride, dried, and concentrated. The residue was purified by alumina column chromatography (eluent: ethyl acetate:hexane=1:4) and recrystallized from ethyl acetate-hexane to obtain the titled compound (17 mg).

m.p.: 75–77° C.

$[\alpha]_D^{20}$=+56.8° (c=0.523 in methanol).

FORMULATION EXAMPLE 1

| | | |
|---|---|---|
| (1) | Compound of Example 12 | 50 mg |
| (2) | Lactose | 34 mg |
| (3) | Corn Starch | 10.6 mg |
| (4) | Corn Starch (pasty) | 5 mg |
| (5) | Magnesium Stearate | 0.4 mg |
| (6) | Carboxymethyl Cellulose Calcium | 20 mg |
| | Total | 120 mg |

These components (1) to (6) were mixed in an ordinary manner, and tabletted, using a tabletting machine, to obtain tablets.

EXPERIMENTAL EXAMPLE 1

Compounds of the present invention were tested for effect of inhibiting amyloid-β protein production in human neuroblastoma IMR-32 cells. Herein referred to were references, Science, 264, 1336 (1994) and Biochemistry, 34, 10272 (1995), etc.

Methods a) Materials Used

Human neuroblastoma IMR-32 cells: purchased from American Type Culture Center

Dulbecco's modified Eagle's medium (hereinafter referred to as DMEM): purchased from Nippon Pharmaceutical Co.

Fetal calf serum (hereinafter referred to as FCS), and a mixture of penicillin (5000 U/ml)/streptomycin (5 mg/ml): both purchased from Bio Whittaker Co.

Phosphate buffered saline (hereinafter referred to as PBS): purchased from Flow Laboratories Co.

Block Ace (trade name): purchased from Dai-Nippon Pharmaceutical Co.

Bovine serum albumin (hereinafter referred to as BSA): purchased from Sigma Co.

Cultivation flask: manufactured by Falcon Co. 48-well Plate: manufactured by Coaster Co.

Standard $A\beta_{1-40}$ and $A\beta_{1-42}$: purchased from Bachem Co.

The other reagents used were commercially-available ones of special grade.

b) Test Method (1) Cultivation of IMR-32 Cells

IMR-32 cells were cultivated in a flask (Falcon, 750 ml) containing 10% FCS/DMEM medium, in an atmosphere of 10% $CO_2$/90% air, at 37° C. to be in confluence. The cultivated cells were seeded into a 48-well plate in a density of $2.5\times10^5$ cells/well, and incubated therein for 3 days under the same condition as above. Then, the culture medium was removed through suction.

A dimethylformamide (DMF) solution containing a test compound was dissolved in 0.5 ml of 0.5% BSA/DMEM, and added to the plate, and the cells were incubated for further 24 hours. As the control, the same volume of DMF but not containing the test compound was dissolved in 0.5 ml of 0.5% BSA/DMEM, and added to the plate.

The supernatant was collected from the plate, and stored at $-20°$ C. or lower until the measurement of its $A\beta$ content.

(2) Enzyme Immunoassay (EIA) for $A\beta$

BAN-50 antibody or BNT-77 antibody was used as the primary antibody. To determine the $A\beta_{1-40}$ of each sample, used was BA-27 antibody as the secondary antibody. To determine the $A\beta_{1-42}$ of each sample, used was BC-05 antibody as the secondary antibody.

BAN-50 antibody or BNT-77 antibody as dissolved in 0.1 M carbonic acid buffer (pH 9.6) in a concentration of 15 μg/ml was added to a polyethylene microtiter plate in an amount of 100 μl/well, and kept at 4° C. overnight. The surface of the plate was washed three times with PBS, and 200 μl of a blocking solution (25% Block Ace/0.1% sodium azide/PBS) was added to the plate. Under this condition, the plate was kept at 4° C. before the addition thereto of the supernatant prepared in (1).

Just before the addition of the supernatant, the surface of the plate was washed three times with PBS, and 50 μl of a buffer for primary reaction (20 mM phosphate buffer, pH 7.0; 400 mM NaCl; 2 mM EDTA; 10% Block Ace; 0.2% BSA; 0.05% sodium azide) was added to the plate. Next, 100 μl of the supernatant and 100 μl of standard $A\beta_{1-40}$ or $A\beta_{1-42}$ as diluted in the buffer for primary reaction (to have a varying concentration of 1000, 200, 40 or 8 μg/ml) were added to the plate, and then kept overnight at 4° C.

The plate was washed three times with PBS, and 100 μl of an HRP-labeled secondary antibody (BA-27 antibody or BC-05 antibody labeled with HRP, horseradish peroxidase) as dissolved in a buffer for secondary reaction (20 mM phosphate buffer, pH 7.0; 400 mM NaCl; 2 mM EDTA; 1% BSA) was added thereto. After having been left at room temperature for 6 hours, the plate was washed seven times with PBS, and 100 μl of a coloring reagent (TMB Peroxidase Substrate, trade name, manufactured by Kirkegaard & Perry Lab.) was added thereto. This was left at room temperature for 8 to 10 minutes, and 100 μl of 1 M phosphoric acid solution was added to the plate to stop the reaction. Then, using a plate reader (MTP-32 Microplate Reader, by Corona Co.), the sample on the plate was subjected to colorimetric determination (at 450 nm).

Results

Four wells were used for one dose of the test compound. The effect of the test compound (10 μM) to inhibit the production and/or secretion of $A\beta_{1-40}$ and $A\beta_{1-42}$ was obtained in terms of the percentage (%) relative to the control. The data obtained are shown in Table 1.

TABLE 1

| Test Compound (Ex. No.) | $A\beta_{1-40}$ (%) | $A\beta_{1-42}$ (%) |
|---|---|---|
| Example 12 | 74 | 75 |

The above data verify that compound (I) of the present invention and compound (I') have the effect of inhibiting amyloid-β protein production and/or secretion.

INDUSTRIAL APPLICABILITY

Compound (I) of the present invention has both an excellent inhibitory effect on amyloid-β protein production and/or secretion and an excellent stimulating effect on secreted form of amyloid precursor protein (sAPP) secretion, while having low toxicity, and has excellent mobility into the brain.

Compound (I') also has the inhibitory effect on amyloid-β protein production and/or secretion and stimulating effect on sAPP secretion.

Therefor, compounds (I) and (I') are useful as safe medicines for preventing and/or treating neurodegenerative disorders (e.g., Alzheimer's disease, Down's syndrome, senile dementia, Parkinson's disease, Creutzfeldt-Jacob disease, amyotrophic sclerosis on lateral fasciculus of spinal, diabetic neuropathy, Huntington's disease, multiple sclerosis, etc.), amyloid angiopathy, neurological disorders caused by cerebrovascular disorders (e.g., cerebral infarction, encephalorrhagia, etc.), a head injury or an injury of spinal cord, as well as ameliorating derangements (for example, depression, anxiety, compulsive neurosis, sleep disorders, etc.) caused by neurodegenerative disorders or neurological disorders, especially for neurodegenerative disorders caused by amyloid-β protein (e.g., Alzheimer's disease, Down's syndrome, etc.).

What is claimed is:

1. A compound of the formula:

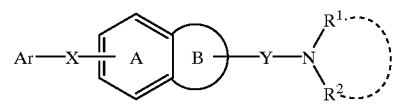

wherein Ar represents an aromatic ring assembly group which may be substituted or a fused aromatic group which may be substituted;

X represents a group of the formula:

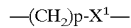

—(CH$_2$)p-X$^1$— wherein $X^1$ represents O or $NR^8$, $R^8$ represents a hydrogen atom, a hydrocarbon group which may be substituted or an acyl, p represents an integer of 0 to 5, Y represents a divalent $C_{1-6}$ aliphatic hydrocarbon group which may contain an oxygen atom or a sulfur atom and may be substituted;

$R^1$ and $R^2$ each represents a hydrogen atom or a lower alkyl which may be substituted, or $R^1$ and $R^2$ form, taken together with the adjacent nitrogen atom, a nitrogen-containing heterocyclic ring which may be substituted;

Ring A represents a benzene ring which may be further substituted apart from the group of the formula:

—X—Ar wherein each symbol is as defined above; and
Ring B represents a 4- to 8-membered carbocyclic ring which may be further substituted by $C_{1-6}$ alkyl apart from the group of the formula:

—Y—$NR^1R^2$ wherein each symbol is as defined above;
or a salt thereof.

2. A compound of claim 1, wherein
Ar is
(i) an aromatic ring assembly group which is composed of two or three rings selected from the group consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, which rings are directly bonded to each other via a single bond, and which assembly group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or (ii) a fused bi- or tri-cyclic $C_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy;

$R^8$ is (a) a hydrogen atom,
(b) a $C_{1-6}$ alkyl, $C_{2-6}$ alkenyl, $C_{2-6}$ alkynyl, $C_{3-6}$ cycloalkyl being optionally condensed with one benzene ring, $C_{6-14}$ aryl or $C_{7-19}$ aralkyl group which may be substituted by 1 to 5 substituents selected from the group consisting of (1) halogen atoms, (2) $C_{1-3}$ alkylenedioxy, (3) nitro, (4) cyano, (5) optionally halogenated $C_{1-6}$ alkyl, (6) optionally halogenated $C_{3-6}$ cycloalkyl, (7) optionally halogenated $C_{1-6}$ alkoxy, (8) optionally halogenated $C_{1-6}$ alkylthio, (9) hydroxy, (10) amino, (11) mono-$C_{1-6}$ alkylamino, (12) di-$C_{1-6}$ alkylamino, (13) formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl or $C_{6-10}$ arylsulfonyl, (14) formylamino, $C_{1-6}$ alkyl-carboxamido, $C_{6-10}$ aryl-carboxamido, $C_{1-6}$ alkoxy-carboxamido or $C_{1-6}$ alkylsulfonylamino, (15) $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy or nicotinoyloxy, (16) 5- to 7-membered saturated cyclic amino, (17) sulfo, (18) a phenyl or 5- or 6-membered aromatic heterocyclic group containing 1 to 4 hetero atoms selected from the group consisting of nitrogen, oxygen and sulfur atoms in addition to carbon atoms, each of which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (19) an aromatic ring assembly group which is composed of two or three rings selected from the group consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, are directly bonded to each other via a single bond, and which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated C$_{3-6}$ cycloalkyl, optionally halogenated C$_{1-6}$ alkoxy, optionally halogenated C$_{1-6}$ alkylthio, hydroxy, amino, mono-C$_{1-6}$ alkylamino, di-C$_{1-6}$ alkylamino, 5- to 7-membered saturated cyclic amino, formyl, carboxy, carbamoyl, C$_{1-6}$ alkyl-carbonyl, C$_{1-6}$ alkoxy-carbonyl, C$_{6-10}$ aryl-carbonyl, C$_{6-10}$ aryloxy-carbonyl, C$_{7-16}$ aralkyloxy-carbonyl, 5- or 6-membered heterocycle carbonyl, mono-C$_{1-6}$ alkyl-carbamoyl, di-C$_{1-6}$ alkyl-carbamoyl, C$_{6-10}$ aryl-carbamoyl, 5- or 6-membered heterocycle carbamoyl, C$_{1-6}$ alkylsulfonyl, C$_{6-10}$ arylsulfonyl, formylamino, C$_{1-6}$ alkyl-carboxamido, C$_{6-10}$ aryl-carboxamido, C$_{1-6}$ alkoxy-carboxamido, C$_{1-6}$ alkylsulfonylamino, C$_{1-6}$ alkyl-carbonyloxy, C$_{6-10}$ aryl-carbonyloxy, C$_{1-6}$ alkoxy-carbonyloxy, mono-C$_{1-6}$ alkyl-carbamoyloxy, di-C$_{1-6}$ alkyl-carbamoyloxy, C$_{6-10}$ aryl-carbamoyloxy, nicotinoyloxy and C$_{6-10}$ aryloxy, and (20) a fused bi- or tn-cyclic C$_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxy, amino, mono-C$_{1-6}$ alkylamino, di-C$_{1-6}$ alkylamino, 5- to 7-membered saturated cyclic amino, formyl, carboxy, carbamoyl, C$_{1-6}$ alkyl-carbonyl, C$_{1-6}$ alkoxy-carbonyl, C$_{6-10}$ aryl-carbonyl, C$_{6-10}$ aryloxy-carbonyl, C$_{7-16}$ aralkyloxy-carbonyl, 5- or 6-membered heterocycle carbonyl, mono-C$_{1-6}$ alkyl-carbamoyl, di-C$_{1-6}$ alkyl-carbamoyl, C$_{6-10}$ aryl-carbamoyl, 5- or 6-membered heterocycle carbamoyl, C$_{1-6}$ alkylsulfonyl, C$_{6-10}$ arylsulfonyl, formylamino, C$_{1-6}$ alkyl-carboxamido, C$_{6-10}$ aryl-carboxamido, C$_{1-6}$ alkoxy-carboxamido, C$_{1-6}$ alkylsulfonylamino, C$_{1-6}$ alkyl-carbonyloxy, C$_{6-10}$ aryl-carbonyloxy, C$_{1-6}$ alkoxy-carbonyloxy, mono-C$_{1-6}$ alkyl-carbamoyloxy, di-C$_{1-6}$ alkyl-carbamoyloxy, C$_{6-10}$ aryl-carbamoyloxy, nicotinoyloxy and C$_{6-10}$ aryloxy, or (c) formyl, carboxy, carbamoyl, C$_{1-6}$ alkyl-carbonyl, C$_{1-6}$ alkoxy-carbonyl, C$_{6-10}$ aryl-carbonyl, C$_{6-10}$ aryloxy-carbonyl, C$_{7-16}$ aralkyloxy-carbonyl, 5- or 6-membered heterocycle carbonyl, mono-C$_{1-6}$ alkyl-carbamoyl, di-C$_{1-6}$ alkyl-carbamoyl, C$_{6-10}$ aryl-carbamoyl, 5- or 6-membered heterocycle carbamoyl, C$_{1-6}$ alkylsulfonyl or C$_{6-10}$ arylsulfonyl;

Y is a C$_{1-6}$ alkylene, a C$_{2-6}$ alkenylene, a C$_{2-6}$ alkynylene or a group of the formula:

—(CH$_2$)m-Y$^1$—(CH$_2$)n- wherein —Y$^1$— is —O—, —S—, —SO— or —SO$_2$—,
m is an integer of 0 to 4,
n is an integer of 1 to 5, and
m+n is an integer of 1 to 5;

R$^1$ and R$^2$ each is a hydrogen atom or a C$_{1-6}$ alkyl which may be substituted by 1 to 5 substituents selected from the group consisting of halogen atoms, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxy, amino, mono-C$_{1-6}$ alkylamino, di-C$_{1-6}$ alkylamino, 5- to 7-membered saturated cyclic amino, formyl, carboxy, carbamoyl, C$_{1-6}$ alkyl-carbonyl, C$_{1-6}$ alkoxy-carbonyl, C$_{6-10}$ aryl-carbonyl, C$_{6-10}$ aryloxy-carbonyl, C$_{7-16}$ aralkyloxy-carbonyl, 5- or 6-membered heterocycle carbonyl, mono-C$_{1-6}$ alkyl-carbamoyl, di-C$_{1-6}$ alkyl-carbamoyl, C$_{6-10}$ aryl-carbamoyl, 5- or 6-membered heterocycle carbamoyl, C$_{1-6}$ alkylsulfonyl, C$_{6-10}$ arylsulfonyl, formylamino, C$_{1-6}$ alkyl-carboxamido, C$_{6-10}$ aryl-carboxamido, C$_{1-6}$ alkoxy-carboxamido, C$_{1-6}$ alkylsulfonylamino, C$_{1-6}$ alkyl-carbonyloxy, C$_{6-10}$ aryl-carbonyloxy, C$_{1-6}$ alkoxy-carbonyloxy, mono-C$_{1-6}$ alkyl-carbamoyloxy, di-C$_{1-6}$ alkyl-carbamoyloxy, C$_{6-10}$ aryl-carbamoyloxy, nicotinoyloxy and C$_{6-10}$ aryloxy or C$_{6-10}$ aryl or R$^1$ and R$^2$ form, taken together with the adjacent nitrogen atom, a 3- to 8-membered nitrogen-containing heterocyclic ring having one nitrogen atom and optionally having 1 to 3 hetero atoms selected from the group consisting of nitrogen, oxygen and sulfur atoms in addition to carbon atoms, which ring may be substituted by 1 to 5 substituents selected from the group consisting of (1) halogen atoms, (2) C$_{1-3}$ alkylenedioxy, (3) nitro, (4) cyano, (5) optionally halogenated C$_{1-6}$ alkyl, (6) optionally halogenated C$_{3-6}$ cycloalkyl, (7) optionally halogenated C$_{1-6}$ alkoxy, (8) optionally halogenated C$_{1-6}$ alkylthio, (9) hydroxy, (10) amino, (11) mono-C$_{1-6}$alkylamino, (12) di-C$_{1-6}$ alkylamino, (13) formyl, carboxy, carbamoyl, C$_{1-6}$ alkyl-carbonyl, C$_{1-6}$ alkoxy-carbonyl, C$_{6-10}$ aryl-carbonyl, C$_{6-10}$ aryloxy-carbonyl, C$_{7-16}$ aralkyloxy carbonyl, 5- or 6-membered heterocycle carbonyl, mono-C$_{1-6}$ alkyl-carbamoyl, di-C$_{1-6}$ alkyl-carbamoyl, C$_{6-10}$ aryl-carbamoyl, 5- or 6-membered heterocycle carbamoyl, C$_{1-6}$ alkylsulfonyl or C$_{6-10}$ arylsulfonyl, (14) formylamino, C$_{1-6}$ alkyl-carboxamido, C$_{6-10}$ aryl-carboxamido, C$_{1-6}$ alkoxy-carboxamido or C$_{1-6}$ alkylsulfonylamino, (15) C$_{1-6}$ alkyl-carbonyloxy, C$_{6-10}$ aryl-carbonyloxy, C$_{1-6}$ alkoxy-carbonyloxy, mono-C$_{1-6}$ alkyl-carbamoyloxy, di-C$_{1-6}$ alkyl-carbamoyloxy, C$_{6-10}$ aryl-carbamoyloxy or nicotinoyloxy, (16) 5- to 7-membered saturated cyclic amino, (17) sulfo, (18) a phenyl or 5- or 6-membered aromatic heterocyclic group containing 1 to 4 hetero atoms selected from the group consisting of nitrogen, oxygen and sulfur atoms in addition to carbon atoms, each of which may be substituted by 1 to 5 substituents selected from the group consisting of halogen atoms, C$_{1-3}$ alkylenedioxy, nitro, cyano, optionally halogenated C$_{1-6}$ alkyl, optionally halogenated C$_{3-6}$ cycloalkyl, optionally halogenated C$_{1-6}$ alkoxy, optionally halogenated C$_{1-6}$ alkylthio, hydroxy, amino, mono-C$_{1-6}$ alkylamino, di-C$_{1-6}$ alkylamino, 5- to 7-membered saturated cyclic amino, formyl, carboxy, carbamoyl, C$_{1-6}$ alkyl-carbonyl, C$_{1-6}$ alkoxy-carbonyl, C$_{6-10}$ aryl-carbonyl, C$_{6-10}$ aryloxy-carbonyl, C$_{7-16}$ aralkyloxy-carbonyl, 5- or 6-membered heterocycle carbonyl, mono-C$_{1-6}$ alkyl-carbamoyl, di-C$_{1-6}$ alkyl-carbamoyl, C$_{6-10}$ aryl-carbamoyl, 5- or 6-membered heterocycle carbamoyl, C$_{1-6}$ alkylsulfonyl, C$_{6-10}$ arylsulfonyl, formylamino, C$_{1-6}$ alkyl-carboxamido, C$_{6-10}$ aryl-carboxamido, C$_{1-6}$ alkoxy-carboxamido, C$_{1-6}$ alkylsulfonylamino, C$_{1-6}$ alkyl-carbonyloxy, C$_{6-10}$ aryl-carbonyloxy, C$_{1-6}$ alkoxy-carbonyloxy, mono-C$_{1-6}$ alkyl-carbamoyloxy, di-C$_{1-6}$ alkyl-carbamoyloxy, C$_{6-10}$ aryl-carbamoyloxy, nicotinoyloxy and C$_{6-10}$ aryloxy, (19) an aromatic ring assembly group which is composed of two or three rings selected from the group consisting of a $C_{6-14}$ aromatic hydrocarbon, a $C_{6-14}$ quinone and a 5- to 14-membered aromatic heterocyclic ring containing 1 to 4 hetero atoms selected from the group consisting of nitrogen, sulfur and oxygen atoms in addition to carbon atoms, are directly bonded to each other via a single bond, and which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (20) a fused bi- or tn-cyclic $C_{10-14}$ aryl or 9- to 14-membered aromatic heterocyclic group containing 1 to 4 hetero atoms selected from the group consisting of nitrogen, oxygen and sulfur atoms in addition to carbon atoms, which group may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, (21) an oxo and (22) $C_{7-19}$ aralkyl;

Ring A is a benzene ring which may be further substituted by 1 to 3 substituents selected from the group consisting of halogen atoms, optionally halogenated $C_{1-6}$ alkyl, optionally halogenated $C_{1-6}$ alkoxy, hydroxy and amino, apart from the group of the formula:

—X—Ar wherein each symbol is as defined above; and

Ring B is a 4-to 8-membered ring of the formula:

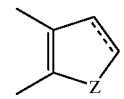

wherein --- is a single bond or a double bond, and
Z is (i) a bond, (ii) a $C_{1-4}$ alkylene, or (iii) a $C_{2-4}$ alkenylene, which ring may be further substituted by 1 to 3 substituents of $C_{1-6}$ alkyl, apart from the group of the formula:

—Y—NR$^1$R$^2$ wherein each symbol is as defined above.

3. A compound of claim 1, wherein Ar is an aromatic ring assembly group which may be substituted.

4. A compound of claim 3, wherein the aromatic rings of the aromatic ring assembly group are two or three aromatic rings selected from the group consisting of benzene, thiophene, pyridine, pyrimidine, 1,2,4-oxadiazole, 1,3,4-oxadiazole, naphthalene and benzofuran.

5. A compound of claim 3, wherein the aromatic ring assembly group is 2-, 3- or 4-biphenylyl.

6. A compound of claim 1, wherein Ar is a 4-biphenylyl which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered saturated cyclic amino, formyl, carboxy, carbamoyl, $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, 5- or 6-membered heterocycle carbonyl, mono-$C_{1-6}$ alkyl-carbamoyl, di-$C_{1-6}$ alkyl-carbamoyl, $C_{6-10}$ aryl-carbamoyl, 5- or 6-membered heterocycle carbamoyl, $C_{1-6}$ alkylsulfonyl, $C_{6-10}$ arylsulfonyl, formylamino, $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy.

7. A compound of claim 1, wherein X is a divalent $C_{1-6}$ aliphatic hydrocarbon group which may contain an oxygen atom.

8. A compound of claim 1, wherein p is 1.

9. A compound of claim 8, wherein $X^1$ is O.

10. A compound of claim 1, wherein Y is a divalent $C_{1-6}$ aliphatic hydrocarbon group.

11. A compound of claim 1, wherein Y is $C_{1-6}$ alkylene.

12. A compound of claim 1, wherein Ring A is a benzene ring substituted by the group of the formula:

—X—Ar wherein each symbol has the same meaning as in claim 1.

13. A compound of claim 1, wherein Ring B is a 4-to 8-membered ring of the formula:

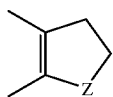

wherein Z is (i) a bond, (ii) a $C_{1-4}$ alkylene, or (iii) a $C_{2-4}$ alkenylene, which ring may be further substituted by 1 to 3 substituents of $C_{1-6}$ alkyl, apart from the group of the formula:

wherein each symbol has the same meaning as in claim 1.

14. A compound of claim 1, wherein Ring B is a 6-membered carbocyclic ring substituted by a group of the formula:

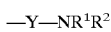

wherein each symbol has the same meaning as in claim 1.

15. A compound of claim 1, wherein Ring B is a ring of the formula:

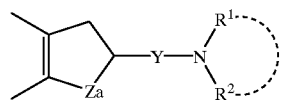

wherein Za is $C_{1-3}$ alkylene.

16. A compound of claim 15, wherein Za is ethylene.

17. A compound of claim 1, wherein the fused ring to be formed by Ring A and Ring B is a ring of the formula:

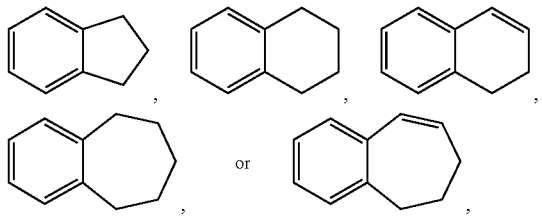

when

X is $CH_2O$.

18. A compound of claim 1, wherein

Ar is 2-, 3- or 4-biphenylyl which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl and $C_{1-6}$ alkyl-carboxamido;

X is $C_{1-3}$ alkylene which may contain an oxygen atom;

Y is $C_{1-6}$ alkylene;

$R^1$ and $R^2$ each is $C_{1-6}$ alkyl;

Ring A is a benzene ring substituted by the group of the formula:

—X—Ar wherein each symbol has the same meaning as in claim 1; and

Ring B is a 6-membered carbocyclic ring substituted by the group of the formula:

wherein each symbol has the same meaning as in claim 1.

19. A compound of the formula:

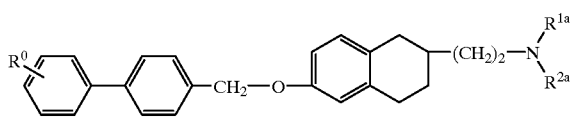

wherein $R^0$ is 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl and $C_{1-6}$ alkyl-carboxamido; and $R^{1a}$ and $R^{2a}$ each is $C_{1-6}$ alkyl, or a salt thereof.

20. A compound of the formula:

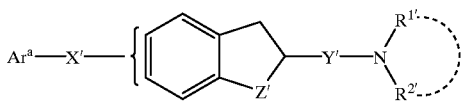

wherein $Ar^a$ is (i) 2, 3- or 4-biphenylyl which may be substituted by 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, amino, formyl and $C_{1-6}$ alkyl-carboxamido, (ii) 4-(2-thienyl)phenyl or 4-(3-thienyl)phenyl, (iii) 4-(3-pyridyl)phenyl, (iv) 6-phenyl-3-pyridyl which may be substituted by a $C_{1-6}$ alkoxy, (v) 5-phenyl-1,3,4-oxadiazol-2-yl, (vi) 4-(2-naphthyl)phenyl, (vii) 4-(2-benzofuranyl)phenyl, (viii) 1- or 2-naphthyl, (ix) 2-quinolyl, (x) 2-benzothiazolyl or (xi) 2-benzofuranyl;

X' is —$CH_2$—O—, or a group of the formula:

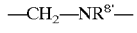

wherein $R^{8'}$ is hydrogen or $C_{1-3}$ alkyl-carbonyl;

Y' is $C_{1-6}$ alkylene;

Z' is —$CH_2$—$CH_2$—; and $R^{1'}$ and $R^{2'}$ each is $C_{1-6}$ alkyl which may be substituted by 1 to 5 substituents selected from the group consisting of di-$C_{1-3}$ alkylamino, $C_{1-3}$ alkoxy-carbonyl and phenyl, or $R^{1'}$ and $R^{2'}$ form, taken together with the adjacent nitrogen atom, a pyrrolidin-1-yl, piperidino or piperazin-1-yl which may be substituted by 1 to 3 substituents selected from the group consisting of hydroxy, $C_{1-3}$ alkoxy-carbonyl, piperidino, phenyl and benzyl, or a salt thereof.

21. An inhibitor for production and/or secretion of amyloid-β protein, which comprises a compound of the formula:

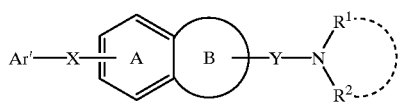

wherein Ar' represents an aromatic group which may be substituted;
X represents a group of the formula:
—(CH₂)p-X¹-, wherein $X^1$ represents O or $NR^8$,
$R^8$ represents a hydrogen atom, a hydrocarbon group which may be substituted or an acyl, p represents an integer of 0 to 5,
Y represents a divalent $C_{1-6}$ aliphatic hydrocarbon group which may contain an oxygen atom or a sulfur atom and may be substituted;
$R^1$ and $R^2$ each represents a hydrogen atom or a lower alkyl which may be substituted, or
$R^1$ and $R^2$ form, taken together with the adjacent nitrogen atom, a nitrogen-containing heterocyclic ring which may be substituted;
Ring A represents a benzene ring which may be further substituted apart from the group of the formula:

—X—Ar wherein each symbol is as defined above; and
Ring B represents a 4- to 8-membered carbocyclic ring which may be further substituted by $C_{1-6}$ alkyl apart from the group of the formula:

—Y—NR¹R² wherein each symbol is as defined above,
or a salt thereof.
22. (+)-6-(4-Biphenylyl)methoxy-2-[2-(N,N-dimethylamino)ethyl]tetralin hydrochloride monohydrate.
23. A compound of claim 1 which is 6-(4-biphenylyl)methoxy-2-(2-piperidinoethyl)tetralin hydrochloride.
24. A process for producing of a compound of claim 1, which comprises;
i) subjecting a compound of the formula:

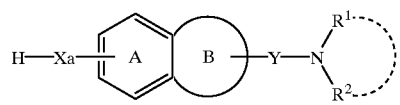

wherein Xa represents an oxygen atom, a sulfur atom which may be oxidized or a group of the formula:

NR⁸ wherein $R^8$ represents a hydrogen atom, a hydrocarbon group which may be substituted or an acyl; and
the other symbols have the same meanings as in claim 1, or a salt thereof, to alkylation or acylation and optionally followed by aryl-coupling of the resultant compound;

ii) subjecting a compound of the formula:

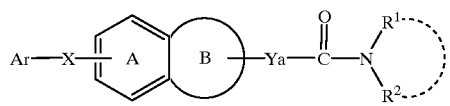

wherein
Ya represents a group to be formed by removing a methylene from Y; and
the other symbols have the same meanings as in claim 1, or a salt thereof, to reduction; or
iii) subjecting a compound of the formula:

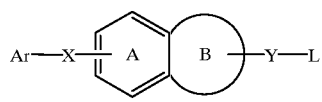

wherein
L represents a leaving group; and
the other symbols have the same meanings as in claim 1, to amination.
25. A pharmaceutical composition which comprises a compound of claim 1 and a pharmaceutically acceptable carrier.
26. A pharmaceutical composition of claim 25 which is an inhibitor for production and/or secretion of amyloid-β protein.
27. A pharmaceutical composition of claim 25 which is for preventing and/or treating neurodegenerative diseases caused by amyloid-β protein.
28. A pharmaceutical composition of claim 26, wherein the neurodegenerative disease caused by amyloid-β protein is Alzheimer's disease.
29. A pharmaceutical composition comprising a therapeutically effective amount of a compound of claim 22, and a pharmaceutically acceptable carrier, diluent or excipient.
30. A method of inhibiting production and/or secretion of amyloid-β protein in mammal, which comprises administering to said mammal an effective amount of a compound of claim 1 or a pharmaceutically acceptable salt thereof with a pharmaceutically acceptable excipient, carrier or diluent.
31. A method of inhibiting production and/or secretion of amyloid-β protein in mammal, which comprises administering to said mammal an effective amount of a compound of the formula:

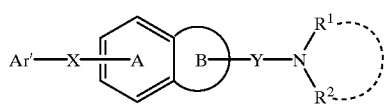

wherein Ar' represents an aromatic group which may be substituted;
X represents a group of the formula:

—(CH₂)p—X¹—, wherein $X^1$ represents O or $NR^8$, $R^8$ represents a hydrogen atom, a hydrocarbon group which may be substituted or an acyl, p represents an integer of 0 to 5, Y represents a divalent $C_{1-6}$ aliphatic hydrocarbon group which may contain an oxygen atom or a sulfur atom and may be substituted;

$R^1$ and $R^2$ each represents a hydrogen atom or a lower alkyl which may be substituted, or $R^1$ and $R^2$ form, taken together with the adjacent nitrogen atom, a nitrogen-containing heterocyclic ring which may be substituted;

Ring A represents a benzene ring which may be further substituted apart from the group of the formula:

—X—Ar wherein each symbol is as defined above; and

Ring B represents a 4- to 8-membered carbocyclic ring which may be further substituted apart from the group of the formula:

—Y—$NR^1R^2$ wherein each symbol is as defined above, or a pharmaceutically acceptable salt thereof with a pharmaceutically acceptable excipient, carrier or diluent.

32. A method of inhibiting production and/or secretion of amyloid-β protein in mammal, which comprises administering to said mammal an effective amount of (+)-6-(4-biphenylyl)methoxy-2-[2-(N,N-dimethylamino)ethyl] tetralin hydrochloride monohydrate.

33. A method of inhibiting production and/or secretion of amyloid-β protein in mammal, which comprises administering to said mammal an effective amount of 6-(4-biphenylyl) methoxy-2-(2-piperidinoethyl)tetralin hydrochloride.

* * * * *